US012589148B2

(12) United States Patent
Mochizuki et al.

(10) Patent No.: US 12,589,148 B2
(45) Date of Patent: *Mar. 31, 2026

(54) IMMUNITY-INDUCING AGENT COMPRISING ANTIGEN PEPTIDE-ADJUVANT NUCLEOTIDE CONJUGATE AND PHARMACEUTICAL COMPOSITION COMPRISING SAME

(71) Applicants: THE UNIVERSITY OF KITAKYUSHU, Fukuoka (JP); DAIICHI SANKYO COMPANY, LIMITED, Tokyo (JP)

(72) Inventors: Shinichi Mochizuki, Fukuoka (JP); Makoto Koizumi, Tokyo (JP); Koji Morita, Tokyo (JP)

(73) Assignees: The University of Kitakyushu, Kitakyushu (JP); Daiichi Sankyo Company, Limited, Tokyo (JP)

( * ) Notice: Subject to any disclaimer, the term of this patent is extended or adjusted under 35 U.S.C. 154(b) by 740 days.

This patent is subject to a terminal disclaimer.

(21) Appl. No.: 17/280,605

(22) PCT Filed: Sep. 27, 2019

(86) PCT No.: PCT/JP2019/038090

§ 371 (c)(1),
(2) Date: Mar. 26, 2021

(87) PCT Pub. No.: WO2020/067400

PCT Pub. Date: Apr. 2, 2020

(65) Prior Publication Data

US 2022/0031839 A1 Feb. 3, 2022

(30) Foreign Application Priority Data

Sep. 28, 2018 (JP) ................................ 2018-186093

(51) Int. Cl.
*A61K 39/39* (2006.01)
*A61K 47/54* (2017.01)
*A61K 39/00* (2006.01)

(52) U.S. Cl.
CPC ............ *A61K 39/39* (2013.01); *A61K 47/548* (2017.08); *A61K 47/549* (2017.08); *A61K 2039/55561* (2013.01)

(58) Field of Classification Search
CPC ...................................................... A61K 39/39
See application file for complete search history.

(56) References Cited

U.S. PATENT DOCUMENTS

| | | | | |
|---|---|---|---|---|
| 10,195,270 | B2 * | 2/2019 | Sakurai | A61K 39/385 |
| 11,793,874 | B2 | 10/2023 | Mochizuki et al. | |
| 12,220,460 | B2 | 2/2025 | Mochizuki et al. | |
| 2006/0084149 | A1 | 4/2006 | Kimura et al. | |
| 2008/0146488 | A1 | 6/2008 | Wettstein | |
| 2014/0051637 | A1 | 2/2014 | Suzumura | |
| 2015/0191730 | A1 | 7/2015 | Levy et al. | |
| 2016/0000906 | A1 | 1/2016 | Diamond | |
| 2016/0186178 | A1 * | 6/2016 | Radovic-Moreno | A61P 31/00 435/375 |
| 2016/0208260 | A1 * | 7/2016 | Ishii | A61P 35/00 |
| 2017/0007695 | A1 * | 1/2017 | Sakurai | A61K 39/015 |
| 2017/0035864 | A1 | 2/2017 | Theriault | |
| 2021/0106678 | A1 | 4/2021 | Mochizuki et al. | |
| 2022/0031839 | A1 | 2/2022 | Mochizuki | |

FOREIGN PATENT DOCUMENTS

| | | | | |
|---|---|---|---|---|
| CN | 101563104 | A | 10/2009 | |
| CN | 107281476 | A | 10/2017 | |
| EP | 1142591 | A1 | 10/2001 | |
| EP | 3 858 383 | A1 | 8/2021 | |
| JP | 2007070307 | A | 3/2007 | |
| JP | 200850907 | | 3/2008 | |
| JP | 2008509072 | | 3/2008 | |
| JP | 2010174107 | A | 8/2010 | |
| JP | 2017500313 | A | 1/2017 | |
| TW | 201639583 | A | 11/2016 | |
| WO | 01/34207 | A1 | 5/2001 | |
| WO | 02/072152 | A1 | 9/2002 | |
| WO | 2012147805 | | 11/2012 | |
| WO | 2015/089114 | A1 | 6/2015 | |
| WO | WO-2015118789 | A1 * | 8/2015 | A61K 31/7088 |
| WO | 2016/152767 | A1 | 9/2016 | |
| WO | 2017/217531 | A1 | 12/2017 | |
| WO | 2020067400 | | 4/2020 | |

OTHER PUBLICATIONS

Kramer et al., 2017, Intracellular Cleavable CpG Oligodeoxynucleotide-Antigen Conjugate Enhances Anti-tumor Immunity, Molecular Therapy, 25(1): 62-70.*
Hayashi et al., 2005, Resistance to influenza A virus infection by antigen-conjugated CpG oligonucleotides, a novel antigen-specific immunomodulator, Biochemical and Biophysical Research Communications, 329: 230-236.*

(Continued)

*Primary Examiner* — Amber D Steele
(74) *Attorney, Agent, or Firm* — Christensen O'Connor Johnson Kindness PLLC

(57) ABSTRACT

The present invention provides an immunity-inducing agent comprising, as an active component, a polynucleotide/peptide conjugate in which a single-chain polynucleotide or polynucleotide derivative comprising a CpG motif, and an antigenic peptide are bound via a spacer, wherein the spacer is covalently bound at one end thereof to the polynucleotide or polynucleotide derivative and covalently bound at the other end thereof to the antigenic peptide, as well as a pharmaceutical composition comprising said immunity-inducing agent.

27 Claims, 5 Drawing Sheets

Specification includes a Sequence Listing.

(56) References Cited

OTHER PUBLICATIONS

Kapadia, C.H., et al. "Extending antigen release from particulate vaccines results in enhanced antitumor immune response," Journal of Controlled Release 2018, vol. 269, pp. 393-404.
Office Action mailed Aug. 23, 2022, issued in corresponding Japanese Application No. 2019-509625, filed Mar. 20, 2018, 7 pages.
Extended European Search Report mailed Aug. 24, 2022, issued in corresponding European Application No. 19865489.9, filed Sep. 27, 2019, 2018, 14 pages.
Maurer, T. et al., "CpG-DNA aided cross-presentation of soluble antigens by dendritic cells", European Journal of Immunology 32(8): 2356-2364, Aug. 2, 2022.
Shirota, H. et al., "Regulation of Murine Airway Eosinophilia and Th2 Cells by Antigen-Conjugated CpG Oligodeoxynucleotides as a Novel Antigen-Specific Immunomodulator", The Journal of Immunology, 164:5575-5582, Jan. 1, 2000.
Wagner, H., "Bacterial CpG DNA Activates Immune Cells to Signal Infectious Danger", Adv. Immunol., 73, 329-368, 1999.
Krieg, A., "CpG Motifs in Bacterial DNA and Their Immune Effects", Annu. Rev. Immunol., 20, 709-760, 2002.
Yamamoto, S., et al., "The discovery of immunostimulatory DNA sequence", Springer Semin Immunopathol, 22, 11-19, 2000.
Taniguchi, M., et al., Standard Immunology, 2nd Edition, 333, 2002.
Sakurai, K., et al., "Molecular Recognition of Adenine, Cytosine, and Uracil in a Single-Stranded RNA by a Natural Polysaccharide: Schizophyllan", J. Am. Chem. Soc., 122, 4520-4521, 2000.
Sakurai, K., et al., "Polysaccharide-Polynucleotide Complexes. 2. Complementary Polynucleotide Mimic Behavior of the Natural Polysaccharide Schizophyllan in the Macromolecular Complex with Single-Stranded RNA and DNA", Biomacromolecules, 2, 641-650, 2001.
Mochizuki, S., et al., "Dectin-1 targeting delivery of TNF-α antisense ODNs complexed with β-1,3-glucan protects mice from LPS-induced hepatitis", J. Control. Release, 151, 155-161, 2001.
Miyoshi, K., et al., "Polysaccharide-Polynucleotide Complexes. Part 32. Structural Analysis of the Curdlan/Poly (cytidylic acid) Complex with Semiempirical Molecular Orbital Calculations", Biomacromolecules, 6, 1540-1546, 2005.
Mizu, M., et al., "A Polysaccharide Carrier for Immunostimulatory CpG DNAs to Enhance Cytokine Secretion", J. Am. Chem. Soc., 126, 8372-8373, 2004.
Mizu, M., et al., "Protection of polynucleotides against nuclease-mediated hydrolysis by complexation with schizophyllan", Biomaterials, 25, 15, 3109-3116, 2004.
Shimada, N., et al., "Synthesis and in Vitro Characterization of Antigen-Conjugated Polysaccharide as a CpG DNA Carrier", Bioconjugate Chem., 17, 1136-1140, 2006.
Khan, S., et al., "Distinct Uptake Mechanisms but Similar Intracellular Processing of Two Different Toll-like Receptor Ligand-Peptide Conjugates in Dendritic Cells", J Biol Chem., 282(29), 21145-21159, Jul. 20, 2007.
Kramer, K., et al., "Intracellular Cleavable CpG Oligodeoxynucleotide-Antigen Conjugate Enhances Anti-tumor Immunity", Mol. Ther., 25(1), 62-70, Jan. 4, 2017.
Shirota, H., et al., "TLR-9 Agonist Immunostimulatory Sequence Adjuvants Linked to Cancer Antigens", Methods in Molecular Biology, vol. 1139, 337-344, 2014.
Kramer, K., et al., "Comparative Study of 5'- and 3'-Linked CpG-Antigen Conjugates for the Induction of Cellular Immune Responses", ACS Omega, vol. 2, 227-235, 2017.
Kupihar, Z., et al., "Synthesis and Application of a Novel, Crystalline Phosphoramidite Monomer with Thiol Terminus, Suitable for the Synthesis of DNA Conjugates", Bioorganic & Medicinal Chemistry, vol. 9, 1241-1247, 2001.
International Search Report mailed Nov. 19, 2019, issued in corresponding International Application No. PCT/JP2019/038090, filed Sep. 27, 2019.
Mochizuki, S., et al., "Immunization with antigenic peptides complexed with β-glucan induces potent cytotoxic T-lymphocyte activity in combination with CpG-ODNs", Journal of Controlled Release, 220, 495-502, 2015.
Tighe, H., et al., "Conjugation of immunostimulatory DNA to the short ragweed allergen Amb a 1 enhances its immunogenicity and reduces its allergenicity", J. Allergy. Clin. Immunol., 106 (1 Pt. 1), 124-134, Jul. 2000.
Mochizuki, S., et al., "Complex Consisting of β-Glucan and Antigenic Peptides with Cleavage Site for Glutathione and Aminopeptidases Induces Potent Cytotoxic T Lymphocytes", Bioconjugate Chem., 28, 2246-2253, Jul. 24, 2017.
International Search Report mailed May 1, 2018, issued in corresponding International Application No. PCT/JP2018/011201, filed Mar. 20, 2018, 2 pages.
Motohiko Suzuki, et al., International Immunopharmacology, vol. 7, Issue 1, Jan. 2007, pp. 46-54.
Mochizuki, S., et al., "Dectin-1 targeting delivery of TNF-α antisense ODNs complexed with β-1,3-glucan protects mice from LPS-induced hepatitis", J. Control. Release, 151, 155-161, 2011.
Irie, et al., Bioconjugate Chem. 2020, 31, 2585-2595.
Rapin, Nicolas et al., Immunogenetics, 2008, vol. 60, No. 12, pp. 759-765.
Search Report mailed Apr. 20, 2021, issued in related International Application No. PCT/JP2021/012787, filed Mar. 26, 2021, 3 pages.
Aurisicchio, L. et al., "A novel minigene scaffold for therapeutic cancer vaccines," OncoImmunology 3, e27529-1-e27529-13; Jan. 2014.
Extended European Search Report mailed Jul. 12, 2024, issued in Application No. EP 21776683.1, filed Mar. 26, 2021, 10 pages.
Daftarian et al., "Novel conjugates of epitope fusion peptides with CpG-ODN display enhanced immunogenicity and HIV recognition," Vaccine (2005), vol. 23, No. 26, pp. 3453-3468.
First Chinese Office Action mailed on Feb. 19, 2025, issued in Chinese App No. 202180024931.3; 18 pages.
Office Action mailed Jun. 5, 2025, issued in U.S. Appl. No. 17/907,531, filed Sep. 27, 2022, 53 pages.
Tung, et al., "Preparation and Applications of Peptide-Oligonucleotide Conjugates;" Bioconjugate Chemistry 11 (5): 605-618 (2000).
Final Office Action mailed Oct. 23, 2025, issued in U.S. Appl. No. 17/907,531, filed Sep. 27, 2022, 33 pages.
Bolcato, V., et al., "Healthcare-acquired Sars-Cov2 infection: A viable legal category?", International Journal of Risk & Safety in Medicine 34: 129-134, 2023.
Palshof, F.K., et al. "Non-preventable cases of breast, prostate, lung and colorectal cancer in 2050 in an elimination scenario of modifiable risk factors," Nature 14:8577, 2024.
Israelsen, A., et al., "Preventing Allergies in Infants: What Foods to Introduce and When," Utah State University Extension, pp. 1-6, 2020.

* cited by examiner

IMMUNITY-INDUCING AGENT COMPRISING ANTIGEN PEPTIDE-ADJUVANT NUCLEOTIDE CONJUGATE AND PHARMACEUTICAL COMPOSITION COMPRISING SAME

CROSS REFERENCES TO RELATED APPLICATIONS

This application is the U.S. national phase of PCT/JP2019/038090 filed on Sep. 27, 2019, which claims priority to Japanese Application No. 2018-186093 filed on Sep. 28, 2018, each expressly incorporated herein by reference in its entirety.

STATEMENT REGARDING SEQUENCE LISTING

The sequence listing associated with this application was provided in the corresponding International Patent Application No. PCT/JP2019/038090, which was filed Sep. 27, 2019, in lieu of a paper copy and is hereby incorporated by reference into the specification. The name of the text file containing the sequence listing is 74166_Seq_List_final_20210324_ST25.txt. The text file is 41,869 bytes; was created on Mar. 24, 2021; and was previously submitted as part of International Patent Application No. PCT/JP2019/038090.

TECHNICAL FIELD

The present invention relates to a novel immunity-inducing agent for inducing antigenic peptide-specific immune responses and comprising an antigenic peptide-adjuvant nucleotide conjugate, and a pharmaceutical composition comprising the same.

BACKGROUND ART

The basic principle for the prevention of infection through vaccination is that pseudo-infection is artificially established to induce acquired immunity and to elicit antibody production and cell-mediated immunity against particular pathogens. It is known that in acquired immunity, T and B cells, which are responsible for "memory" in immunity, play key roles, and the diversity of antibody variable regions caused by DNA recombination enables specific immune responses to numerous numbers of antigens. In contrast, innate immunity, which is mainly mediated by phargocytes such as leukocytes, macrophages and dendritic cells, has been conventionally considered to be a non-specific process of phagocytosis of foreign substances and pathogens, and to merely serve as a "stopgap measure" until acquired immunity is established. However, as a result of advances in studies on the molecular mechanisms of innate immunity, it has been clarified that self/non-self-specific recognition takes place also in innate immunity, and that innate immunity is essential for the establishment of acquired immunity. To be more specific, it has been clarified in recent studies that a family of Toll-like receptors (TLRs), present on antigen-presenting cells such as dendritic cells, macrophages and B cells, can respond to various pathogens, induce cytokine production, and induce acquired immunity through, for example, promotion of differentiation of naïve T cells into Th1 cells, and activation of killer T cells.

Pathogens recognized by the series of TLRs are composed of a wide variety of constituents. One of those constituents is a DNA having a CpG motif (CpG DNA), which acts as a ligand for TLR9. A CpG motif is a nucleotide sequence composed of six nucleotides, in which cytosine (C) and guanine (G) are situated side-by-side at the center and flanked by two purine nucleotides and two pyrimidine nucleotides, and are represented by -PuPu-CG-PyPy-(Pu represents a purine nucleotide, and Py represents a pyrimidine nucleotide) (in humans, GTCGTT is also known to have ligand activity for TLR9). This motif is rarely found in mammals, and is found commonly in bacteria (based on frequency as calculated in terms of probability). In mammals, most of rare CpG motifs are methylated. Unmethylated CpG motifs, which are rarely observed in mammals, have potent immunostimulatory activity (refer to e.g., NPLs 1 to 3). CpG DNA incorporated into cells by endocytosis is recognized by TLR9 present in phagosome-like vesicles, and can induce strong Th1 responses. Th1 responses suppress Th2-dominated allergic responses, and also have potent antitumor activity. Therefore, CpG DNA is expected to be used not only for infection prevention but also as an adjuvant for allergic and neoplastic diseases (refer to e.g., NPL 4).

However, when CpG DNA is used as an adjuvant in immunotherapy, the problem is how to deliver CpG DNA into target cells while protecting DNA against degradation by nucleases in cytoplasm or plasma, or against non-specific binding to proteins.

The present inventors have focused their attention on polysaccharides having a β-1,3-glucan backbone (hereinafter also abbreviated as "β-1,3-glucans") as a novel gene carrier, and found that β-1,3-glucans are capable of forming new types of complexes by binding to various nucleic acids including nucleic acid drugs (e.g., antisense DNA, CpG DNA) (refer to e.g., PTLs 1, 2, and NPLs 5 to 7).

It was found that when β-1,3-glucan naturally existing in a triple helix conformation is dissolved in an aprotic polar organic solvent such as dimethyl sulfoxide (DMSO) or in a 0.1 N or higher alkali solution to allow glucan to be cleaved into single strands, then a single-strand nucleic acid is added, and the solvent is replaced with water or neutralized again, a triple helix complex consisting of one nucleic acid molecule and two β-1,3-glucan molecules is formed. It is considered that in such a triple helix complex, a linkage between the β-1,3-glucan molecules and the nucleic acid molecule is mainly formed by hydrogen bonding and hydrophobic interaction (refer to NPL 8).

The complexation of nucleic acids with β-1,3-glucans, as described above, enabled delivery of nucleic acids into cells while suppressing undesired interactions of nucleic acids with proteins in the body, such as hydrolysis of nucleic acids by nucleases, or non-specific binding of nucleic acids to plasma proteins. The delivery of CpG DNA into cells was succeeded with the use of a complex of β-1,3-glucan and DNA, or a ternary complex containing a protein with antigenicity (refer to e.g., PTLs 3, 4, and NPLs 9 to 11).

However, the aforementioned conventional techniques had some problems as described below. For example, according to the method of producing a β-1,3-glucan/antigenic protein/CpG DNA ternary complex as disclosed in NPL 11, a formyl group is produced on a glucose residue at the side chain of β-1,3-glucan by oxidization with periodic acid, and the formyl group is reacted with an amino group of a peptide with antigenicity (hereinafter also abbreviated as "antigenic peptide") by reductive amination reaction, so that a complex in which β-1,3-glucan and the antigenic peptide are covalently bound together can be formed. However, this method has a problem of very low yield. In view of such circumstances, according to, for example, the method of producing a β-1,3-glucan/antigenic protein (antigenic peptide)/CpG DNA ternary complex as disclosed in PTL 4, β-1,3-glucan having a formyl group at the side chain thereof and an antigenic peptide are reacted with each other in an aqueous alkaline solution at the same time as, or sequentially followed by, neutralization, so that improvement can be achieved in yield and the reactivity between the formyl group at the side chain of β-1,3-glucan and an amino group of the antigenic peptide. However, since a peptide contains a plurality of amino groups, control of a reaction site is difficult to achieve. Therefore, there is concern that there may occur various problems, such as variation in immunogenicity depending on the reaction site of an antigenic peptide, or difficulty in separation and purification due to complexity of reaction mixtures with β-1,3-glucan. Further, the procedure for forming a β-1,3-glucan/antigenic peptide complex based on the formation of covalent bonding is more complicated than that for forming a β-1,3-glucan/DNA complex through hydrogen bonding. From these viewpoints, the method of producing a β-1,3-glucan/antigenic peptide/CpG DNA ternary complex as disclosed in PTL 4 still has problems with ease of production and the like.

In view of such problems, the present inventors have proposed a peptide/β-1,3-glucan complex having excellent ease of production and high immunostimulatory activity, the complex comprising: a polysaccharide having a β-1,3-glucan backbone; and a peptide/polynucleotide conjugate in which an antigenic peptide is covalently bound to a polynucleotide or polynucleotide derivative, wherein the polynucleotide or polynucleotide derivative of the peptide/polynucleotide conjugate is bound via hydrogen bonding to the polysaccharide having a β-1,3-glucan backbone to form a complex having a triple helix structure consisting of one molecular chain of the polynucleotide or polynucleotide derivative and two molecular chains of the polysaccharide having a β-1,3-glucan backbone (refer to PTL 5). However, PTL 5 is silent about whether the peptide/polynucleotide conjugate, which constitutes the peptide/β-1,3-glucan complex, has per se immunity induction activity.

There are some reports suggestive of the immunity induction activity of conjugates of CpG DNA with antigenic peptides or proteins (refer to NPLs 12, 13). NPL 12 discloses that administration of conjugates of CpG DNA with ovalbumin (OVA) antigen-derived 18- to 24-mer peptides improves OVA antigen presentation in $CD8^+$ T lymphocytes (CTLs), but is not explicitly demonstrative of induction of CTL cytotoxic activity. NPL 13 discloses that administration of conjugates of CpG DNA with OVA antigen proteins induces CTL cytotoxic activity, but those conjugates were injected at a high dose of 10 μg per mouse, and also, production of those conjugates required complicated steps of chemical DNA synthesis, production of antigen proteins through culturing/purification, and conjugation of DNA with antigen proteins. Thus, the technique of NPL 13 has problems with activity at low doses and ease of production

CITATION LIST

Patent Literatures

PTL 1: International Patent Publication No. WO 01/34207
PTL 2: International Patent Publication No. WO 02/072152
PTL 3: Japanese Unexamined Patent Application Publication No. JP 2010-174107
PTL 4: Japanese Unexamined Patent Application Publication No. JP 2007-70307
PTL 5: International Patent Publication No. WO 2015/118789

Non Patent Literatures

NPL 1: Bacterial CpG DNA Activates Immune Cells to Signal Infectious Danger. H. Wagner, *Adv. Immunol.,* 73, 329-368 (1999).
NPL 2: CpG Motifs in Bacterial DNA and Their Immune Effects. M. Krieg, *Annu. Rev. Immunol.,* 20, 709-760 (2002).
NPL 3: The Discovery of Immunostimulatory DNA Sequence. S. Yamamoto, T. Yamamoto, and T. Tokunaga, *Springer Seminars in Immunopathology,* 22, 11-19 (2000).
NPL 4: *Standard Immunology,* 2nd Edition, Igaku-Shoin Ltd., 333 (2002)
NPL 5: Molecular Recognition of Adenine, Cytosine, and Uracil in a Single-Stranded RNA by a Natural Polysaccharide: Schizophyllan. K. Sakurai and S. Shinkai, *J. Am. Chem. Soc.,* 122, 4520-4521 (2000).
NPL 6: Polysaccharide-Polynucleotide Complexes. 2. Complementary Polynucleotide Mimic Behavior of the Natural Polysaccharide Schizophyllan in the Macromolecular Complex with Single-Stranded RNA and DNA. K. Sakurai, M. Mizu and S. Shinkai, *Biomacromolecules,* 2, 641-650 (2001).
NPL 7: Dectin-1 Targeting Delivery of TNF-α Antisense ODNs Complexed with B-1,3-glucan Protects Mice from LPS-induced Hepatitis. S. Mochizuki and K. Sakurai, *J. Control. Release,* 151, 155-161 (2011).
NPL 8: Structural Analysis of the Curdlan/Poly (cytidylic acid) Complex with Semiempirical Molecular Orbital Calculations. K. Miyoshi, K. Uezu, K. Sakurai and S. Shinkai, *Biomacromolecules,* 6, 1540-1546 (2005).
NPL 9: A Polysaccharide Carrier for Immunostimulatory CpG DNAs to Enhance Cytokine Secretion. M. Mizu, K. Koumoto, T. Anada, T. Matsumoto, M. Numata, S. Shinkai, T. Nagasaki and K. Sakurai, *J. Am. Chem. Soc.,* 126, 8372-8373 (2004).
NPL 10: Protection of Polynucleotides against Nuclease-mediated Hydrolysis by Complexation with Schizophyllan. M. Mizu, K. Koumoto, T. Kimura, K. Sakurai and S. Shinkai, *Biomaterials,* 25, 15, 3109-3116 (2004).
NPL 11: Synthesis and in Vitro Characterization of Antigen-Conjugated Polysaccharide as a CpG DNA Carrier. N. Shimada, K. J. Ishii, Y. Takeda, C. Coban, Y. Torii, S. Shinkai, S. Akira and K. Sakurai, *Bioconjugate Chem.,* 17 1136-1140 (2006).
NPL 12: Distinct Uptake Mechanisms but Similar Intracellular Processing of Two Different Toll-like Receptor Ligand-Peptide Conjugates in Dendritic Cells, Khan S., et al., *J. Biol. Chem.,* 282, 21145-21159 (2007).
NPL 13: Intracellular Cleavable CpG Oligodeoxynucleotide-Antigen Conjugate Enhances Anti-tumor Immunity, Kramer K, et al., *Mol. Ther.,* 25, 62-70 (2017).

SUMMARY OF INVENTION

Technical Problem

It was not known whether peptide/polynucleotide conjugates have apparent immunity induction activity on their own.

The present inventors found that peptide/polynucleotide conjugates which are not complexed with β-1,3-glucan, especially peptide/polynucleotide conjugates comprising a CpG motif, have high immunity induction activity on their own; and thus, the inventors completed the present invention. Therefore, this invention has as its object to provide an immunity-inducing agent having excellent ease of production and high immunostimulatory activity, and a pharmaceutical composition comprising the same.

Solution to Problem

A first aspect of the present invention in accordance with the aforementioned object solves the problems mentioned hereinabove by providing an immunity-inducing agent comprising, as an active component, a polynucleotide/peptide conjugate in which a single-chain polynucleotide or polynucleotide derivative comprising a CpG motif, and an antigenic peptide are bound via a spacer, wherein the spacer is covalently bound at one end thereof to the polynucleotide or polynucleotide derivative and covalently bound at the other end thereof to the antigenic peptide.

In the immunity-inducing agent according to the first aspect of the present invention, the antigenic peptide may have an amino acid length of not less than 5 but not more than 30.

In the immunity-inducing agent according to the first aspect of the present invention, the antigenic peptide may have an amino acid length of not less than 8 but not more than 11.

In the immunity-inducing agent according to the first aspect of the present invention, the polynucleotide or polynucleotide derivative may be a polydeoxyribonucleotide (DNA) or a DNA derivative comprising two or more CpG motifs.

In the immunity-inducing agent according to the first aspect of the present invention, the polynucleotide or polynucleotide derivative may have a nucleotide length of not less than 15 but not more than 40.

In the immunity-inducing agent according to the first aspect of the present invention, the polynucleotide or polynucleotide derivative may have a nucleotide length of not less than 20 but not more than 30.

In the immunity-inducing agent according to the first aspect of the present invention, the polynucleotide or polynucleotide derivative may be a polynucleotide derivative in which phosphodiester bonds are at least partially substituted with phosphorothioate bonds.

In the immunity-inducing agent according to the first aspect of the present invention, in the polynucleotide derivative in which phosphodiester bonds are at least partially substituted with phosphorothioate bonds, not less than 50% of the phosphodiester bonds may be substituted with phosphorothioate bonds.

In the polynucleotide derivative in which phosphodiester bonds are at least partially substituted with phosphorothioate bonds, not less than 90% of the phosphodiester bonds may be substituted with phosphorothioate bonds.

In the immunity-inducing agent according to the first aspect of the present invention, one or both of the covalent bond between the spacer and the polynucleotide or polynucleotide derivative, and the covalent bond between the spacer and the antigenic peptide are preferably a covalent bond(s) that is (are) cleavable in biological environment.

In the immunity-inducing agent according to the first aspect of the present invention, the antigenic peptide which constitutes the polynucleotide/peptide conjugate, and the spacer bound to the polynucleotide or polynucleotide derivative may be bound together via a covalent bond (disulfide bond) produced by a reaction between a thiol group of a cysteine residue at the N-terminus of the antigenic peptide and a thiol group of the spacer.

In the immunity-inducing agent according to the first aspect of the present invention, the spacer may comprise a repeating unit represented by the following formula.

[Chem. 1]

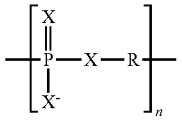

In the above formula,

X represents an oxygen atom or a sulfur atom (wherein each X may be the same or different), R represents any of $(CH_2)_pO$, $(CH_2)_qNH$, and $(CH_2CH_2O)_m$ (wherein m, p and q each independently represent a natural number of not more than 10), and n represents a natural number of not more than 10.

In the immunity-inducing agent according to the first aspect of the present invention, the spacer may have a structure represented by any of the following formulas.

[Chem. 2]

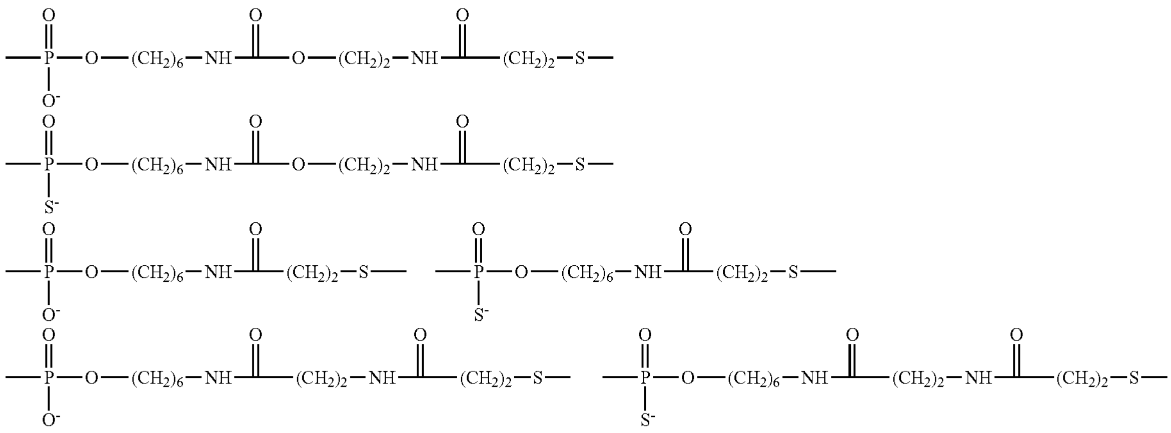

-continued

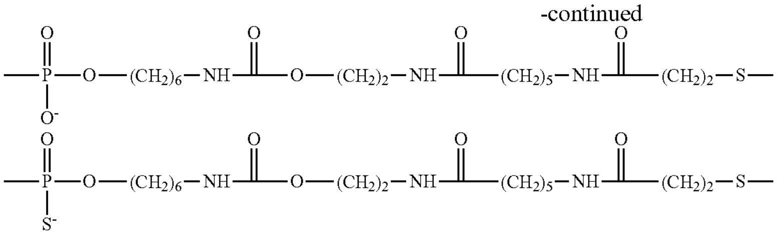

In the immunity-inducing agent according to the first aspect of the present invention, it is preferred that the antigenic peptide should have an amino acid length of not less than 5 but not more than 30, that the polynucleotide or polynucleotide derivative should be a polydeoxyribonucleotide (DNA) or a DNA derivative comprising two or more CpG motifs, that the polynucleotide derivative should be a polynucleotide derivative in which phosphodiester bonds are at least partially substituted with phosphorothioate bonds, and that one or both of the covalent bond between the spacer and the polynucleotide or polynucleotide derivative, and the covalent bond between the spacer and the antigenic peptide have a structure(s) that is (are) a covalent bond(s) that is (are) cleavable in biological environment.

In the immunity-inducing agent according to the first aspect of the present invention, it is more preferred that the antigenic peptide should have an amino acid length of not less than 8 but not more than 11, that the polynucleotide or polynucleotide derivative should be a polydeoxyribonucleotide (DNA) or a DNA derivative comprising two or more CpG motifs and having a nucleotide length of not less than 20 but not more than 30, that the polynucleotide derivative should be a polynucleotide derivative in which not less than 90% of phosphodiester bonds are substituted with phosphorothioate bonds, that the antigenic peptide which constitutes the polynucleotide/peptide conjugate, and the spacer bound to the polynucleotide or polynucleotide derivative should be bound together via a covalent bond (disulfide bond) produced by a reaction between a thiol group of a cysteine residue at the N-terminus of the antigenic peptide and a thiol group of the spacer, and that the spacer should have a structure represented by any of the following formulas.

[Chem. 3]

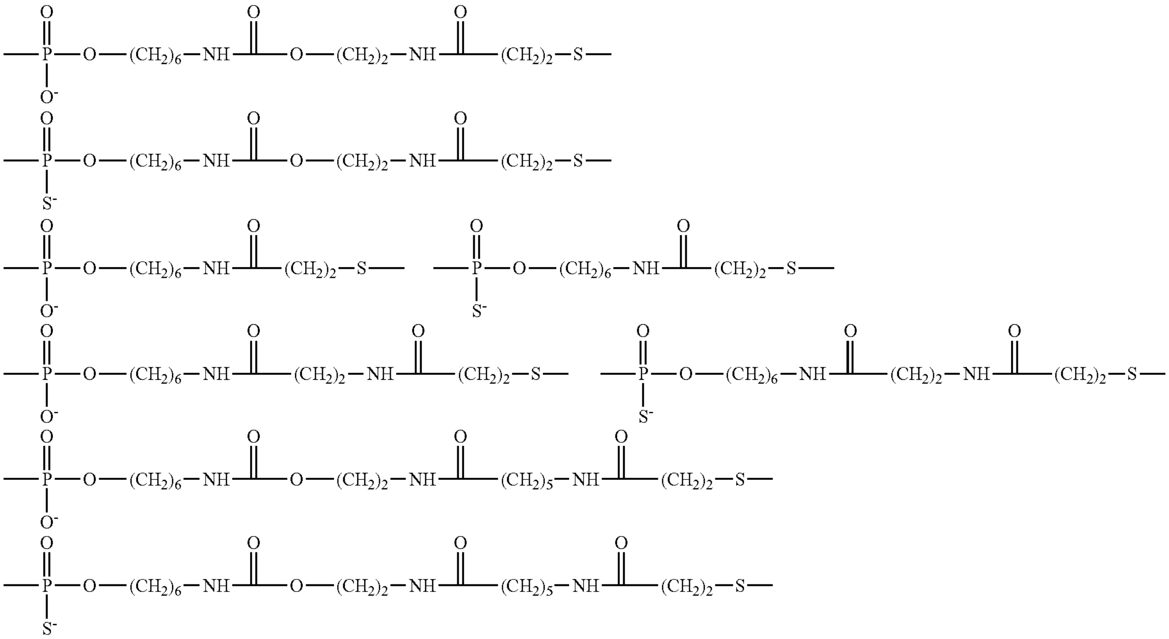

In the immunity-inducing agent according to the first aspect of the present invention, a substance having immunostimulatory activity may be further contained as an adjuvant.

A second aspect of the present invention solves the problems mentioned hereinabove by providing a pharmaceutical composition comprising the immunity-inducing agent according to the first aspect of the present invention.

The second aspect of the present invention may be a pharmaceutical composition for treating tumor.

According to another aspect of the present invention, there is provided a method for treating or preventing a disease, the method comprising administering an effective amount of the immunity-inducing agent according to the first aspect of this invention to a subject in need thereof. In this aspect, the disease may be a tumor.

According to a still another aspect of the present invention, there is provided use of the immunity-inducing agent according to the first aspect of this invention for the production of a medicament for treating or preventing a disease. In this aspect, the disease may be a tumor.

Advantageous Effects of Invention

The peptide/polynucleotide conjugate of the present invention can be used as a highly active immunity-inducing agent having excellent ease of production. Further, immunity-inducing agents having immunity induction activity against a wide variety of antigens can be easily designed by combining an antigenic peptide with a polynucleotide or polynucleotide derivative in an appropriate manner.

DESCRIPTION OF EMBODIMENTS

Figure 1:
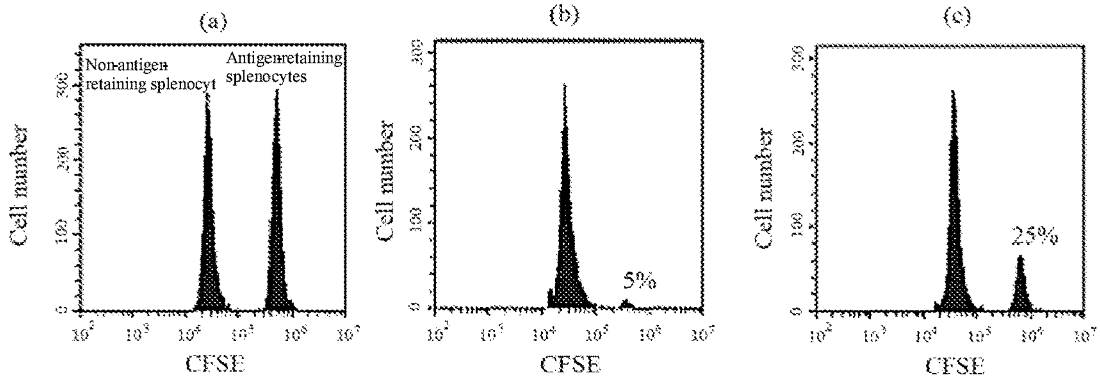
FIG. 1 depicts the results of the flow cytometric analysis performed in Example 2.

The immunity-inducing agent according to the first aspect of the present invention (hereinafter also abbreviated as "immunity-inducing agent") comprises, as an active component, a polynucleotide/peptide conjugate in which a single-chain polynucleotide or polynucleotide derivative comprising a CpG motif, and an antigenic peptide are bound via a spacer, wherein the spacer is covalently bound at one end thereof to the polynucleotide or polynucleotide derivative and covalently bound at the other end thereof to the antigenic peptide.

The peptide/polynucleotide conjugate is a complex in which an antigenic peptide and a polynucleotide or polynucleotide derivative are bound together via covalent bonding. As the "antigenic peptide", any peptide having any amino acid sequence consisting of any numbers of amino acid residues can be used without particular limitation, as long as it has antigenicity—namely as long as it can be recognized as a foreign substance in the immune system of a living body and elicit specific antibody production (induce an immune response). In this aspect of the present invention, if an antigenic peptide has no cysteine (Cys) in its sequence, a peptide modified by artificially adding one cysteine to the N-terminus of an antigenic epitope peptide derived from an antigenic protein can be used as an antigenic peptide. Examples of the antigenic peptide used to produce the peptide/polynucleotide conjugate serving as an active component of the immunity-inducing agent according to this aspect of the invention include proteins responsible for allergies such as food allergy, pathogens such as bacteria and viruses, and proteins originating from tumor cells and the like, as long as they have a partial amino acid sequence that can act as an epitope. The number of amino acid residues constituting the antigenic peptide is not particularly limited as long as they can act as an epitope, but the number of amino acid residues is commonly in the range of from 5 to 30, and most commonly in the range of approximately from 8 to 17.

The antigenic peptide can be obtained using any known method, such as enzymatic degradation of a protein of origin, or peptide synthesis. Further, the amino acid sequence of the antigenic peptide can be determined using any known method such as epitope analysis with peptide arrays.

Examples of peptides that can be used as antigenic peptides include: MHC-1 T cell epitopes registered on the epitope peptide database IEDB (last accessed: Aug. 11, 2014); the peptides disclosed in the paper written by Chowell, et al. (TCR contact residue hydrophobicity is a hallmark of immunogenic CD8+ T cell epitopes, PNAS, Apr. 7, 2015, 112 (14), E1754-E1762, Table. S1); and the peptides listed in Tables 1 to 7 below. In this aspect of the present invention, peptides modified by adding one cysteine residue to the N-terminus of such antigenic peptides (except for those antigenic peptides inherently having a cysteine residue in their sequence) can be used as antigenic peptides.

TABLE 1

Diseases to be treated: Infections

| Antigen | Sequence | MHC subtype | SEQ ID NO. |
|---|---|---|---|
| Human Papilloma virus (HPV) E7 | YMLDLQPETT | HLA-A*0201 | 1 |
| | RAHYNIVTF | H-2 Db | 2 |
| HPV E6 | NTLEQTVKK | HLA-A*1101 | 3 |
| | EVYDFAFRDL | H-2 Kb | 4 |
| Hepatitis B virus (HBV) S protein | FLLTRILTI | HLA-A*0201 | 5 |
| | GLSPTVWLSV | HLA-A*0201 | 6 |
| | WLSLLVPFV | HLA-A*0201 | 7 |
| HBV core protein | FLPSDFFPSV | HLA-A*0201 | 8 |
| | YVNVNMGLK | HLA-A*11 | 9 |
| HBV polymerase | KLHLYSHPI | HLA-A*0201 | 10 |
| | GLSRYVARL | HLA-A*0201 | 11 |
| HBV polyprotein | KLVALGINAV | HLA-A*0201 | 12 |
| | GVDPNIRTGV | HLA-A*0201 | 13 |
| | ALYDVVTKL | HLA-A*0201 | 14 |

TABLE 1-continued

| Diseases to be treated: Infections | | | |
|---|---|---|---|
| Antigen | Sequence | MHC subtype | SEQ ID NO. |
| HBV HBsAg | VWLSVIWM | H-2 Kb | 15 |
| Herpes simplex virus (HSV) | SLPITVYYA | HLA-A*0201 | 16 |
| glycoprotein D | VLLNAPSEA | HLA-A*0201 | 17 |
| | ALLEDPVGT | HLA-A*0201 | 18 |
| HSV glycoprotein B | RMLGDVMAV | HLA-A*0201 | 19 |
| | NLLTTPKFT | HLA-A*0201 | 20 |
| Cytomegalovirus (CMV) pp65 | NLVPMVATV | HLA-A*0201 | 21 |
| | VYALPLKML | HLA-A*2402 | 22 |
| | QYDPVAALF | HLA-A*2402 | 23 |
| CMV 1E-1 | VLEETSVML | HLA-A*0201 | 24 |
| | AYAQKIFKI | HLA-A*2402 | 25 |
| Influenza virus NP | CTELKLSDY | HLA-A*0101 | 26 |
| Influenza virus M1 | GILGFVFTL | HLA-A*0201 | 27 |
| | ILGFVFTLTV | HLA-A*0201 | 28 |
| Influenza virus HA2 | YIGEVLVSV | HLA-A*0201 | 29 |
| Influenza virus nucleoprotein | KLGEFYNQMM | HLA-A*0201 | 30 |
| Respiratory Syncytial Virus (RSV) M2 | YLEKESIYY | HLA-A*0101 | 31 |
| | SYIGSINNI | H-2 Kd | 32 |
| RSV NP | KMLKEMGEV | HLA-A*0201 | 33 |
| RSV F protein | AITTILAAV | HLA-A*0201 | 34 |
| | ALLSTNKAV | HLA-A*0201 | 35 |

TABLE 2

| Diseases to be treated: Infections | | | |
|---|---|---|---|
| Antigen | Sequence | MHC subtype | SEQ ID NO. |
| | ELDKYKNAV | HLA-A*0201 | 36 |
| | FLLGVGSAI | HLA-A*0201 | 37 |
| | FMNYTLNNT | HLA-A*0201 | 38 |
| | HLEGEVNKI | HLA-A*0201 | 39 |
| | KIMTSKTDV | HLA-A*0201 | 40 |
| | KINQSLAFI | HLA-A*0201 | 41 |
| | SVYDFFVWL | H-2 Kb | 42 |
| Human Immunodeficiency Virus (HIV) | RYLKDQQLL | HLA-A*2402 | 43 |
| Env | SLLNATAIAV | HLA-A*0201 | 44 |
| HIV Gag | SLYNTVATL | HLA-A*0201 | 45 |
| | RTLNAWVKV | HLA-A*0201 | 46 |
| | FLGKIWPS | HLA-A*0201 | 47 |
| | TLNAWVKVV | HLA-A*0201 | 48 |
| | SLFNTVATL | HLA-A*0201 | 49 |
| | SLYNTVATLY | HLA-A*0201 | 50 |
| Polyomavirus VP1 | LLMWEAVTV | HLA-A*0201 | 51 |
| Polyomavirus Large T | LLLIWFRPV | HLA-A*0201 | 52 |
| Human T-cell leukemia virus type 1 | LLFGYPVYV | HLA-A*0201 | 53 |
| (HTLV-1) Tax | SFHSLHLLF | HLA-A*2402 | 54 |
| Epstein-Barr virus (EBV) BRLF1 | DYCNVLNKEF | HLA-A*2402 | 55 |
| | TLDYKPLSV | HLA-A*0201 | 55 |
| | YVLDHLIVV | HLA-A*0201 | 57 |
| EBV LIMP-1 | YLLEMLWRL | HLA-A*0201 | 58 |
| | YLQQNWWTL | HLA-A*0201 | 59 |

TABLE 3

| Diseases to be treated: Cancers | | | |
|---|---|---|---|
| Antigen | Sequence | MHC subtype | SEQ ID NO. |
| ABL1 | QQAHCLWCV | HLA-A*0201 | 60 |
| ACPP | ALDVYNGLL | HLA-A*0201 | 61 |
| ACPP | ALNVYNGLL | HLA-A*0201 | 62 |
| BA46 | NLFETPVEA | HLA-A*0201 | 63 |
| BA46 | GLQHWVPEL | HLA-A*0201 | 64 |
| BAP31 | KLDVGNAEV | HLA-A*0201 | 65 |
| BCL-2 | PLFDFSWLSL | HLA-A*0201 | 66 |
| BCL-2 | YLNRHLHTWI | HLA-A*0201 | 67 |
| BCL-2 | WLSLKTLLSL | HLA-A*0201 | 68 |
| BCL-2 | ALSPVPPVV | HLA-A*0201 | 69 |
| BCL-X | YLNDHLEPWI | HLA-A*0201 | 70 |
| BMI1 | CLPSPSTPV | HLA-A*0201 | 71 |
| BMI1 | TLQDIVYKL | HLA-A*0201 | 72 |
| CAMEL | MLMAQEALAFL | HLA-A*0201 | 73 |
| CB9L2 | ALYLMELTM | HLA-A*0201 | 74 |
| CD33 | YLISGDSPV | HLA-A*0201 | 75 |
| CEACAM | YLSGANLNL | HLA-A*0201 | 76 |
| DLK1 | ILGVLTSLV | HLA-A*0201 | 77 |
| Endosialin | LLVPTCVFLV | HLA-A*0201 | 78 |
| EphA2 | TLADFDPRV | HLA-A*0201 | 79 |
| EZH2 | YMCSFLFNL | HLA-A*0201 | 80 |
| EZH2 | SQADALKYV | HLA-A*0201 | 81 |
| FAPα | ALVCYGPGI | HLA-A*0201 | 82 |
| FAPα | GLFKCGIAV | HLA-A*0201 | 83 |
| FLT1 | TLFWLLTL | HLA-A*0201 | 84 |
| FOLR1 | EIWTHSYKV | HLA-A*0201 | 85 |
| Glycipan 3 | FVGEFFTDV | HLA-A*0201 | 86 |
| gp100 | KTWGQYWQV | HLA-A*0201 | 87 |
| gp100 | ITDQVPFSV | HLA-A*0201 | 88 |
| gp100 | IMDQVPFSV | HLA-A*0201 | 89 |
| gp100 | YLEPGPVTV | HLA-A*0201 | 90 |
| HO-1 | QLFEELQEL | HLA-A*0201 | 91 |
| Heparanase | LLLGPLGPL | HLA-A*0201 | 92 |
| HER2 | ILHDGAYSL | HLA-A*0201 | 93 |
| HER2 | LIAHNQVRQV | HLA-A*0201 | 94 |

TABLE 4

| Diseases to be treated: Cancers | | | |
|---|---|---|---|
| Antigen | Sequence | MHC subtype | SEQ ID NO. |
| HER2 | KIFGSLAFL | HLA-A*0201 | 95 |
| HMMR | ILSLELMKL | HLA-A*0201 | 96 |
| IL13Ra | ALPFGFILV | HLA-A*0201 | 97 |
| IDO | ALLEIASCL | HLA-A*0201 | 98 |
| ITGB8 | ALMEQQHYV | HLA-A*0201 | 99 |
| KLK | VISNDVCAQV | HLA-A*0201 | 100 |
| Lengsin | FIYDFCIFGV | HLA-A*0201 | 101 |
| LIVIN | QLCPICRAPV | HLA-A*0201 | 102 |
| LMP-1 | YLQQNWWTL | HLA-A*0201 | 103 |
| LY6K | LLLASIAAGL | HLA-A*0201 | 104 |
| MAGE-10 | GLYDGMEHL | HLA-A*0201 | 105 |
| MAGE-A3 | KVAELVHFL | HLA-A*0201 | 106 |
| MAGE-C1 | FLAMLKNTV | HLA-A*0201 | 107 |
| MAGE-3 | FLWGPRALV | HLA-A*0201 | 108 |
| MAGE-4 | GVYDGREHTV | HLA-A*0201 | 109 |
| MAGE-A1 | KVLEYVIKV | HLA-A*0201 | 110 |
| MAGE-A2 | YLQLVFGIEV | HLA-A*0201 | 111 |
| MART-1 | ELAGIGILTV | HLA-A*0201 | 112 |
| MSLN | SLLFLLFSL | HLA-A*0201 | 113 |
| MSLN | VLPLTVAEV | HLA-A*0201 | 114 |
| Midkine | AQCQETIRV | HLA-A*0201 | 115 |
| MS4A1 | SLFLGILSV | HLA-A*0201 | 116 |
| NRP-1 | GMLGMVSGL | HLA-A*0201 | 117 |
| NY-ESO-1 | SLLMWITQC | HLA-A*0201 | 118 |
| NY-ESO-1 | SLLMWITQV | HLA-A*0201 | 119 |
| BGLAP | YLYQWLGAPV | HLA-A*0201 | 120 |
| p53 | YLGSYGFRL | HLA-A*0201 | 121 |
| p53 | KLCPVQLWV | HLA-A*0201 | 122 |
| p53 | SLPPPGTRV | HLA-A*0201 | 123 |
| p53 | GLAPPQHLIRV | HLA-A*0201 | 124 |
| p53 | LLGRNSFEV | HLA-A*0201 | 125 |
| p53 | RMPEAAPPV | HLA-A*0201 | 126 |
| p53 | STPPPGTRV | HLA-A*0201 | 127 |
| PASD1 | YLVGNVCIL | HLA-A*0201 | 128 |
| PASD1 | QLLDGFMITL | HLA-A*0201 | 129 |

TABLE 5

| Diseases to be treated: Cancers | | | |
|---|---|---|---|
| Antigen | Sequence | MHC subtype | SEQ ID NO. |
| PASD1 | ELSDSLGPV | HLA-A*0201 | 130 |
| PIAC1 | SIDWFMVTV | HLA-A*0201 | 131 |
| Pr1 | VLQELNVTV | HLA-A*0201 | 132 |
| PRAME | ALYVDSLFFL | HLA-A*0201 | 133 |
| PRAME | VLDGLDVLL | HLA-A*0201 | 134 |
| Prominin1 | YLQWIEFSI | HLA-A*0201 | 135 |
| PSA | KLQCVDLHV | HLA-A*0201 | 136 |
| PSA | FLTPKKLQCV | HLA-A*0201 | 137 |
| PSCA | AILALLPAL | HLA-A*0201 | 138 |
| PSCA | QLGEQCWTV | HLA-A*0201 | 139 |
| PSMA | SLFEPPPPG | HLA-A*0201 | 140 |
| PSMA | MMNDQLMFL | HLA-A*0201 | 141 |
| PSMA | VLAGGFFLL | HLA-A*0201 | 142 |
| RNF43 | ALWPWLLMAT | HLA-A*0201 | 143 |
| SART3 | RLAEYQAYI | HLA-A*0201 | 144 |
| STEAP1 | MLAVFLPIV | HLA-A*0201 | 145 |
| Survivin | LMLGEFLKL | HLA-A*0201 | 146 |
| Survivin-3a | LTLGEFLKL | HLA-A*0201 | 147 |
| Survivin | TLPPAWQPFL | HLA-A*0201 | 148 |
| TACE | YLIELIDRV | HLA-A*0201 | 149 |
| TARP 2M | FLPSPLFFFL | HLA-A*0201 | 150 |
| TARP | FLFLRNFSL | HLA-A*0201 | 151 |
| Telomerese | YLQVNSLQTV | HLA-A*0201 | 152 |
| Telomerase | ILAKFLHWL | HLA-A*0201 | 153 |
| Telomerase | ALLTSRLRFI | HLA-A*0201 | 154 |
| Telomerase | RLTSRVKAL | HLA-A*0201 | 155 |
| Telomerase | GLLGASVLGL | HLA-A*0201 | 166 |
| TGF I3 | RLSSCVPVA | HLA-A*0201 | 157 |
| topII | FLYDDNQRV | HLA-A*0201 | 158 |
| TRAG | GLIQLVEGV | HLA-A*0201 | 159 |
| TRAG | SILLRDAGLV | HLA-A*0201 | 160 |
| Mucin | LLLTVLTVV | HLA-A*0201 | 161 |
| Mucin | LLLLTVLTV | HLA-A*0201 | 162 |
| Tyrosinase | YMDGTMSQV | HLA-A*0201 | 163 |
| WT1 | RMFPNAPYL | HLA-A*0201 | 164 |

TABLE 6

| Diseases to be treated: Cancers | | | |
|---|---|---|---|
| Antigen | Sequence | MHC subtype | SEQ ID NO. |
| WT1 | VLDFAPPGA | HLA-A*0201 | 165 |
| WT1 | SLGEQQYSV | HLA-A*0201 | 166 |
| ABL1 | CLWCVPQLR | HLA-A*0201 | 167 |
| BCR-ABL | GVRGRVEEI | HLA-A*0201 | 168 |
| HSP105 | RLMNDMTAV | HLA-A*0201 | 169 |
| HSP105 | KLMSSNSTDL | HLA-A*0201 | 170 |
| CD105 | LLTAALWYV | HLA-A*0201 | 171 |
| BCL-2A1 | DYLQYVLQI | HLA-A*2402 | 172 |
| C1orf59 | GYCTQIGIF | HLA-A*2402 | 173 |
| Carbonic anhydrase | EYRALQLHL | HLA-A*2402 | 174 |
| DEP DC1 | EYYELFVNI | HLA-A*2402 | 175 |
| FOXM1 | IYTWIEDHF | HLA-A*2402 | 176 |
| Glycipan 3 | EYILSLEEL | HLA-A*2402 | 177 |
| gp100 | VYFFLPDHL | HLA-A*2402 | 178 |
| HJURP | KWLISPVKI | HLA-A*2402 | 179 |
| hTOM34p | KLRGEVKQNL | HLA-A*2402 | 180 |
| IL13r | VYYNWQYLL | HLA-A*2402 | 181 |
| KIF20A | KYYLRVRPLL | HLA-A*2402 | 182 |
| KIF20A | VYLRVRPLL | HLA-A*2402 | 183 |
| LY6K | RYCNLEGPPI | HLA-A*2402 | 184 |
| MELK | EYCPGGNLF | HLA-A*2402 | 185 |
| Midkine | RYNAQCQETI | HLA-A*2402 | 186 |
| Nuf2 | VYGIRLEHF | HLA-A*2402 | 187 |
| BGLAP | LYQWLGAPV | HLA-A*2402 | 188 |
| p-Cadherin | DYLNEWGSRF | HLA-A*2402 | 189 |
| PSA | CYASGWGSI | HLA-A*2402 | 190 |
| RNF43 | NYQPVWLCL | HLA-A*2402 | 191 |
| Survivin | AYACNTSTL | HLA-A*2402 | 192 |
| TTK | SYRNEIAYL | HLA-A*2402 | 193 |
| Tyrosinase | AFLPWHRLF | HLA-A*2402 | 194 |
| WT1 | CYTWNQMNL | HLA-A*2402 | 195 |

TABLE 7

| Origin of peptide | Amino acid sequence | SEQ ID NO. |
|---|---|---|
| Ovalbumin (OVA) | SIINFEKL | 196 |
| Murine melanocyte gp100 | EGSRNQDWL | 197 |
| Human melanocyte gp100 | KVPRNQDWL | 198 |
| CT26 (colon cancer line) | SPSYVYHQF | 199 |
| Influenza virus HA | IYSTVASSL | 200 |
| Influenza virus NP | ASNENMDTM | 201 |
| Influenza virus PA | SSLENFRAYV | 202 |
| β-galactosidase | DAPIYTNV | 203 |
| MuLV (Murine leukemia virus) p15E | KSPWFTTL | 204 |
| SeV (Sendai virus) | FAPGNYPAL | 205 |
| MCMV (Murine cytomegalovirus) IE1 | YPHFMPTNL | 206 |
| LCMV (Lymphocytic gp33 choriomeningitis virus) | KAVYNFATM | 207 |
| LCMV NP396 | FQPQNGQFI | 208 |
| LCMV NP118 | RPQASGVYM | 209 |
| *Plasmodium malariae* Pb9 | SYIPSAEKI | 210 |
| HIV P18-I10 | RGPGRAFVTI | 211 |
| BCG MPT51 | GGPHAVYLL | 212 |
| Human CEA (Human carcinoembryonic antigen) | EAQNTTYL | 213 |
| P815 (Mouse-derived antigen-presenting cell) | LPYLGWLVF | 214 |
| HBsAg (Hepatitis B virus antigen) | IPQSLDSWWTSL | 215 |
| HSV-1 (Murine herpes simplex virus) gB | SSIEFARL | 216 |
| HY (Male-specific antigen) Uty | WMHHNMDLI | 217 |
| EGFP (Enhanced green fluorescent protein) | HYLSTQSAL | 218 |
| HER2 | TYLPTNASL | 219 |
| VSV (Vesicular stomatitis virus) NP | RGYVYQGL | 220 |
| Polyomavirus MT | RRLGRTLLL | 221 |

As the single-chain polynucleotide or polynucleotide derivative constituting a polynucleotide/peptide conjugate, any polynucleotide or polynucleotide derivative having any nucleotide sequence consisting of any numbers of nucleotides can be used without particular limitation, as long as it comprises one or a plurality of (preferably a plurality of) CpG motifs. Specific examples of CpG motifs include AGCGTT, GACGTT, GACGTC, GTCGTT, and the like. The number of CpG motifs contained in the polynucleotide is not particularly limited, but preferably one to six CpG motifs, more preferably two to four CpG motifs, are contained in the polynucleotide. The polynucleotide or polynucleotide derivative is preferably a polydeoxyribonucleotide (DNA) or a phosphorothioate-modified DNA derivative comprising two or more CpG motifs, but may be partially composed of an RNA or an RNA derivative. When an RNA or an RNA derivative is contained, the content of one or a plurality of such RNAs or RNA derivatives is preferably not more than 20% (specifically not more than 20, 19, 18, 17, 16, 15, 14, 13, 12, 11, 10, 9, 8, 7, 6, 5, 4, 3, 2 or 1%).

The number of nucleotides contained in the polynucleotide or polynucleotide derivative is in the range of preferably from 15 to 40 (specifically 15, 16, 17, 18, 19, 20, 21, 22, 23, 24, 25, 26, 27, 28, 29, 30, 31, 32, 33, 34, 35, 36, 37, 38, 39 or 40), more preferably from 20 to 30 (specifically 20, 21, 22, 23, 24, 25, 26, 27, 28, 29 or 30). Specific examples of preferred polynucleotides or polynucleotide derivatives include those listed in Table 8 below.

TABLE 8

| | DNA comprising CpG motifs (5'→3') *Phosphodiester bonds are completely substituted with phosphorothioate bonds. | SEQ ID NO. |
|---|---|---|
| K3 | ATCGACTCTCGAGCGTTCTC | 222 |
| K3-20(b) | GAGCGTTCTCGAGCGTTCTC | 223 |
| K3-21 | CGAGCGTTCTCGAGCGTTCTC | 224 |
| K3-24 | TCTCGAGCGTTCTCGAGCGTTCTC | 225 |
| K3-27 | GACTCTCGAGCGTTCTCGAGCGTTCTC | 226 |
| K3-30(a) | GAGCGTTCTCATCGACTCTCGAGCGTTCTC | 227 |
| K3-30(b) | ATCGACTCTCGAGCGTTCTCGAGCGTTCTC | 228 |
| K3-40 | ATCGACTCTCGAGCGTTCTCATCGACTCTCGAGCGTTCTC | 229 |
| K3-30(c) | CTCAGCGTTCTCAGCGTTCTCAGCGTTCTC | 230 |
| K3-30(d) | TTTAGCGTTTTTAGCGTTTTAGCGTTTTT | 231 |
| K3-30(e) | TTAGCGTTTAGCGTTTAGCGTTTAGCGTTT | 232 |
| K3-30(f) | TTAGCGTTTAGCGTTTAGCGTTTAGCGTTT | 233 |
| K3-26(a) | TCAGCGTTTCAGCGTTTCAGCGTTTC | 234 |
| K3-26(b) | TTAGCGTTTTAGCGTTTTAGCGTTTT | 235 |
| ODN1668 | TCCATGACGTTCCTGATGCT | 236 |
| ODN1668-30 | TGACGTTCCTTCCATGACGTTCCTGATGCT | 237 |
| ODN1668-40 | TCCATGACGTTCCTGATGCTTCCATGACGTTCCTGATGCT | 238 |
| ODN1826 | TCCATGACGTTCCTGACGTT | 239 |
| ODN1826-30 | TGACGTTCCTTCCATGACGTTCCTGACGTT | 240 |
| ODN1826-40 | TCCATGACGTTCCTGACGTTTCCATGACGTTCCTGACGTT | 241 |
| ODN2006 | TCGTCGTTTTGTCGTTTTGTCGTT | 242 |
| ODN2006-30 | GTCGTTTCGTCGTTTTGTCGTTTTGTCGTT | 243 |
| ODN2006-40 | TCGTCGTTTTGTCGTTTCGTCGTTTTGTCGTTTTGTCGTT | 244 |
| ODN684 | TCGACGTTCGTCGTTCGTCGTTC | 245 |
| ODN684-30 | TCGTCGTTCGACGTTCGTCGTTCGTCGTTC | 246 |
| ODN684-40 | GTTCGTCGTTTCGTCGTTCGACGTTCGTCGTTCGTCGTTC | 247 |
| ODND-SL01 | TCGCGACGTTCGCCCGACGTTCGGTA | 248 |
| ODND-SL01-35 | TCGCGACGTTCGCGACGTTCGCCCGACGTTCGGTA | 249 |

Since the polynucleotide is susceptible to degradation by nuclease in the living body, a polynucleotide derivative may be used instead of the polynucleotide with the aim of enhancing stability in the living body. Examples of the polynucleotide derivative include those derivatives in which the hydroxyl groups at the 2' position of a ribonucleotide are completely or partially substituted with fluorine or methoxy groups, those derivatives in which the phosphodiester bonds in a polyribonucleotide (RNA) or a polydeoxyribonucleotide (DNA) are completely or partially substituted with phosphorothioate bonds, and the like. In the case of those derivatives in which the phosphodiester bonds in a polyribonucleotide or a polydeoxyribonucleotide are partially substituted with phosphorothioate bonds, it is preferred that not less than 50% (specifically not less than 50, 60, 70, 80 or 90%) of the phosphodiester bonds should be substituted with phosphorothioate bonds, and it is more preferred that not less than 90% (specifically not less than 90, 91, 92, 93, 94, 95, 96, 97, 98 or 99%) of the phosphodiester bonds should be substituted with phosphorothioate bonds. The phosphodiester bonds may be substantially completely substituted with phosphorothioate bonds. The positions of phosphodiester bonds to be substituted with phosphorothioate bonds are not particularly limited. Two or more consecutive phosphodiester bonds may be substituted, or phosphodiester bonds may be substituted so as to ensure that phosphorothioate bonds are not adjacent to each other.

The polynucleotide or polynucleotide derivative, which is covalently bound to the antigenic peptide via a spacer, can be bound to any of the N-terminus, C-terminus, and side chains of the antigenic peptide, but it is preferred that the polynucleotide or polynucleotide derivative should be bound toward the N-terminus of the antigenic peptide. If an antigenic peptide contains no Cys residue, a peptide modified by adding a Cys residue to the N-terminus of the antigenic peptide can be used. The polynucleotide or polynucleotide derivative and the antigenic peptide are bound together via a spacer, which is covalently bound at one end thereof to the polynucleotide or polynucleotide derivative and covalently bound at the other end thereof to the antigenic peptide. As the reactive functional groups used to form bonding between the spacer and the polynucleotide or polynucleotide derivative or between the spacer and the antigenic peptide, any functional groups present in the antigenic peptide and the polynucleotide or polynucleotide derivative can be used as they are, or any groups that can react with a functional group activated by chemical modification to form covalent bonding can be used. It is preferred that an oxygen atom of the hydroxy group at the 5' end or 3' end of the polynucleotide or polynucleotide derivative should be bound to the spacer. Also, it is preferred that a sulfur atom of the sulfhydryl group at the side chain of a Cys residue in the antigenic peptide should be bound to the spacer.

One preferred example of the peptide/polynucleotide conjugate has a structure represented by formula (A) below, in which a region toward the N-terminus of an antigenic peptide is bound via a spacer Sp to a region toward the 3' end or 5' end of a polynucleotide or polynucleotide derivative.

[Polynucleotide or polynucleotide derivative]—Sp—[Antigenic peptide] Formula (A)

Examples of the spacer Sp include alkylene group, polyethylene glycol (PEG), and the like. The spacer may comprise a repeating unit having a phosphodiester structure, as represented by the following formula.

[Chem. 4]

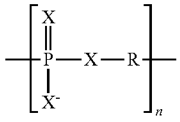

In the above formula, X represents an oxygen atom or a sulfur atom (wherein each X may be the same or different), R represents any of $(CH_2)_pO$, $(CH_2)_qNH$, and $(CH_2CH_2O)_m$ (wherein m, p and q each independently represent a natural number of not more than 10), and n represents a natural number of not more than 10.

Since such repeating unit do not undergo hydrolysis by nuclease, there occurs no significant decrease in stability in the living body even when X is an oxygen atom. For example, when R is $(CH_2)_3$, the size of the repeating unit is nearly equal to that of a ribonucleotide or a deoxyribonucleotide, so that it can be expected that a production cost associated with substitution of part of the polynucleotide or polynucleotide derivative with the spacer can be reduced. Specific examples of the spacer Sp include the following.

[Chem. 5)

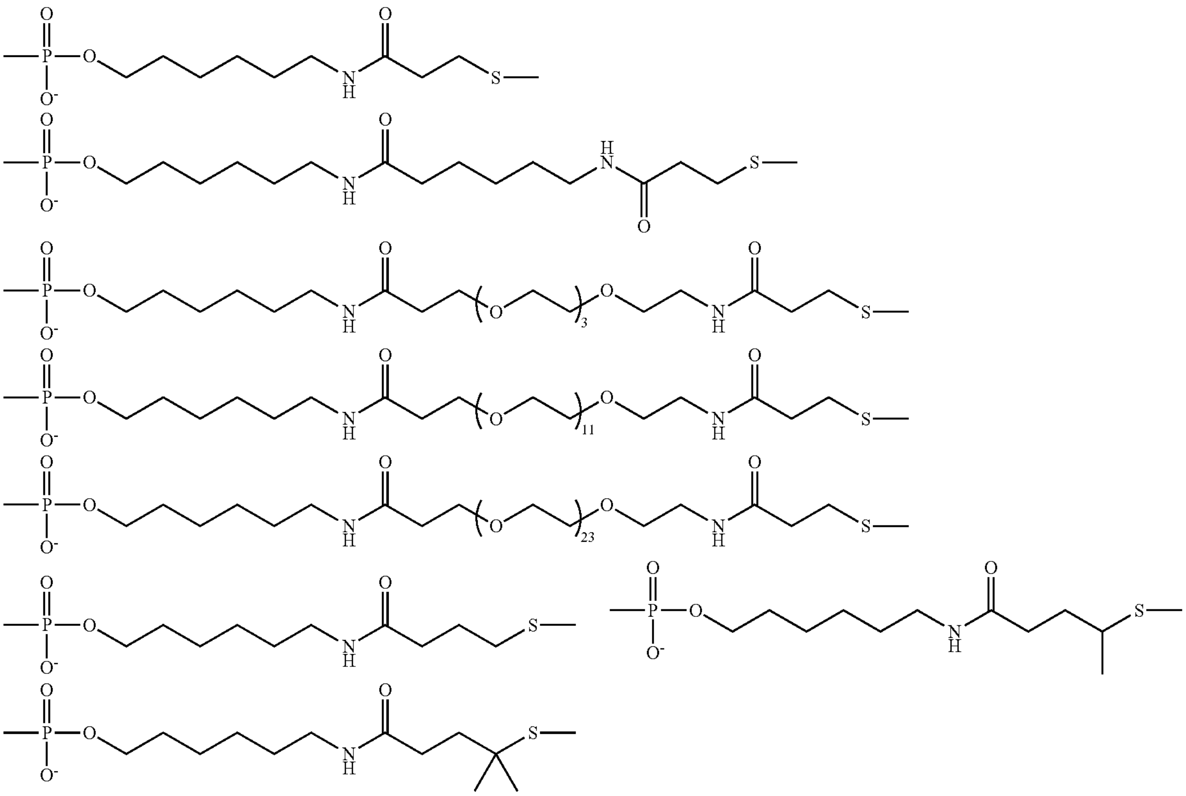

-continued
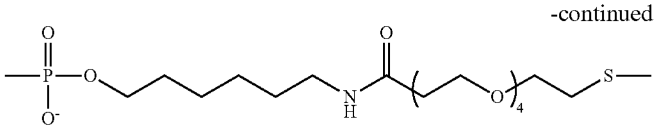
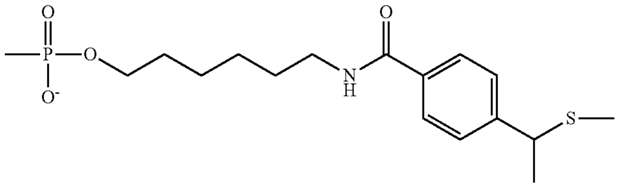
[Chem. 6]
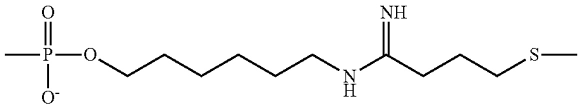
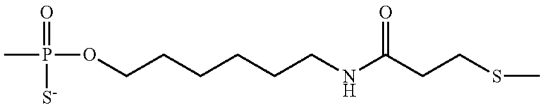
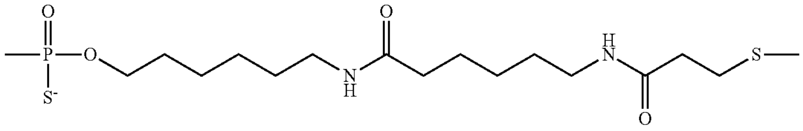
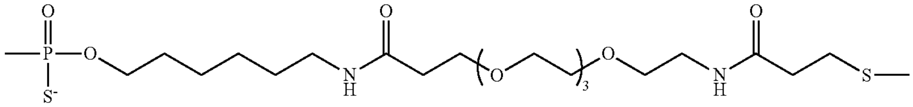
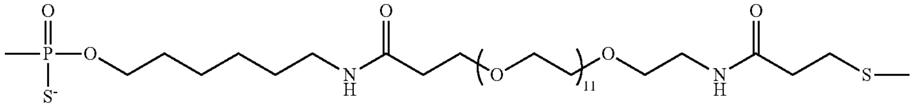
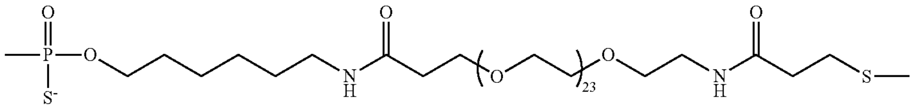
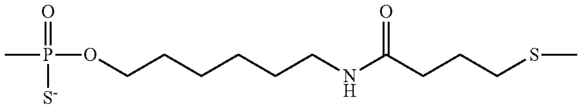
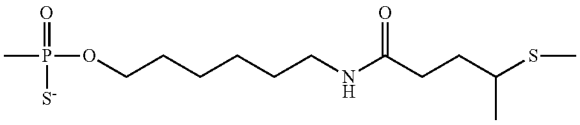
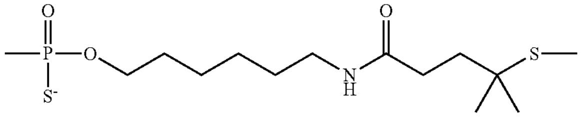
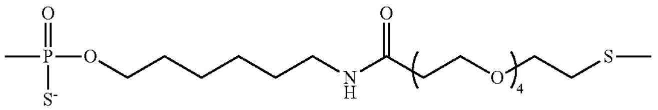
[Chem. 7]
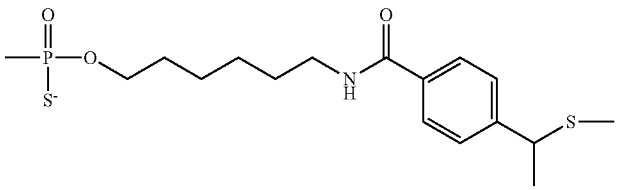
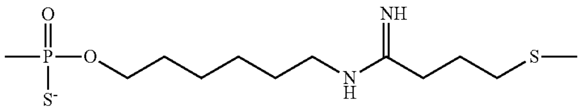
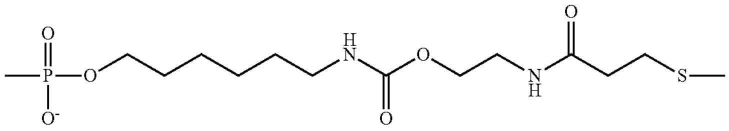

-continued
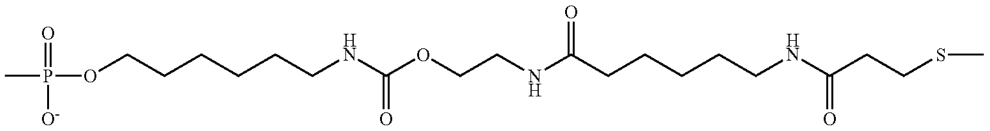
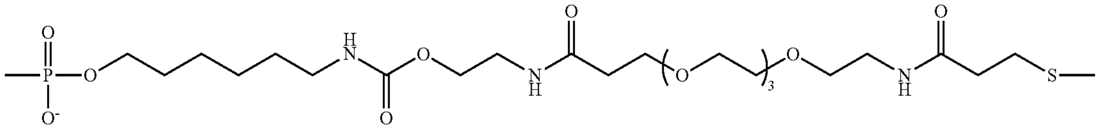
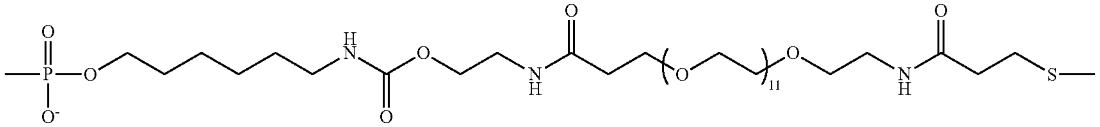
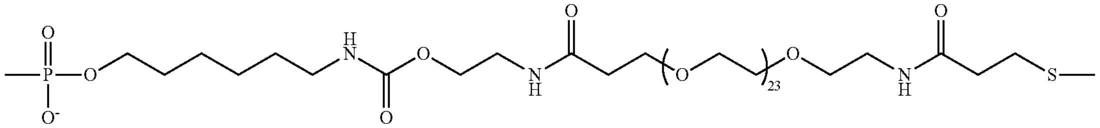
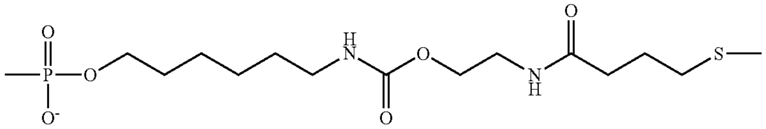
[Chem. 8]
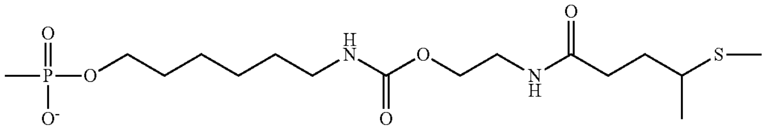
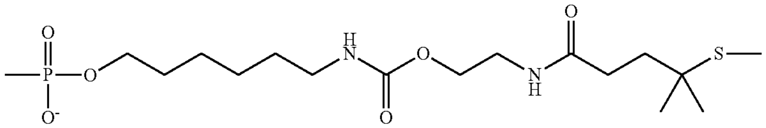
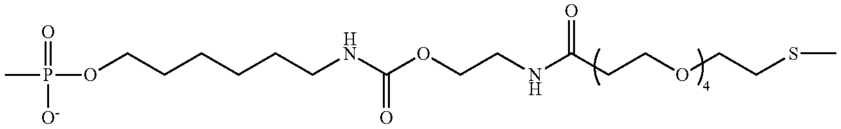
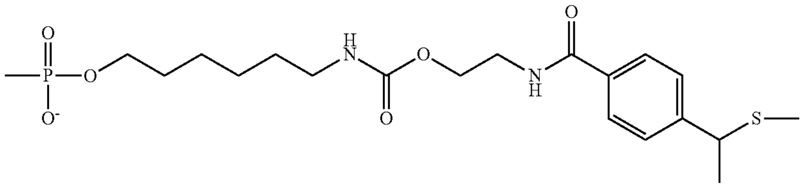
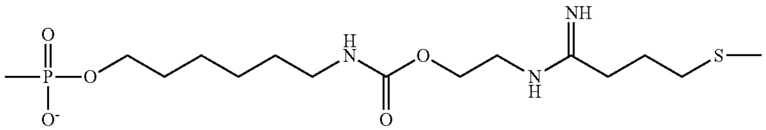
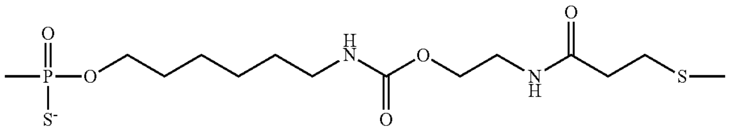
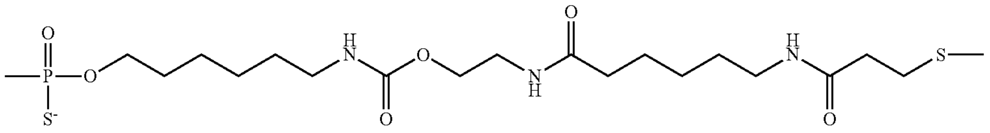

-continued
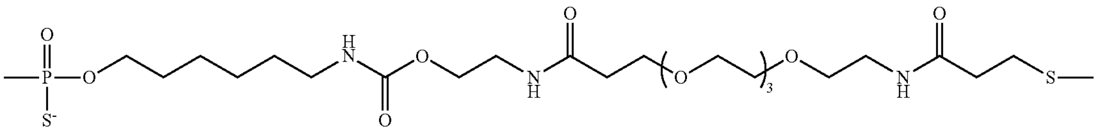
[Chem. 9]
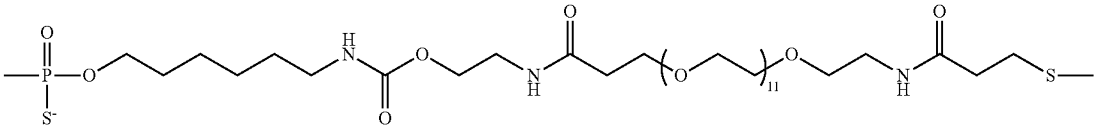
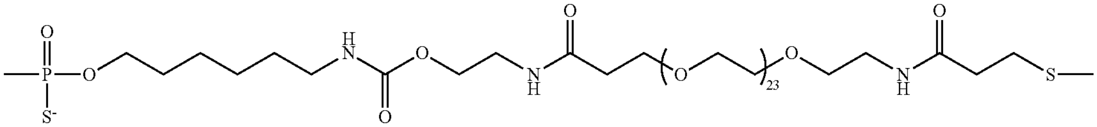
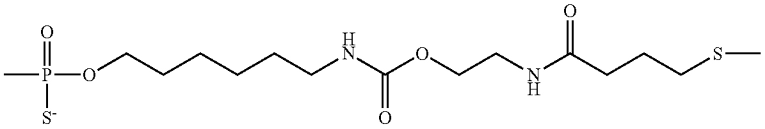
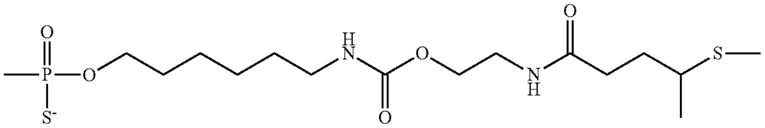
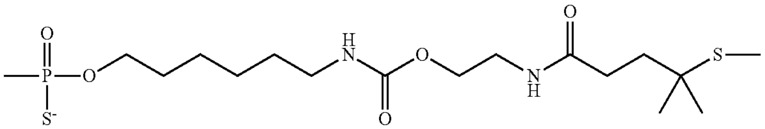
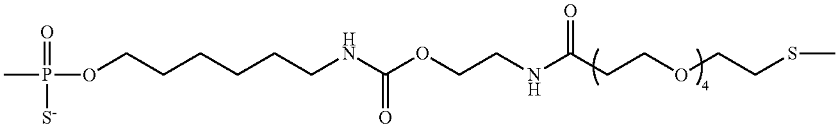
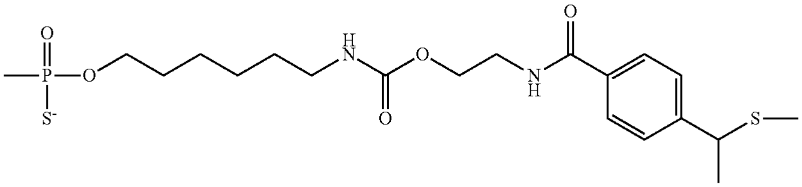
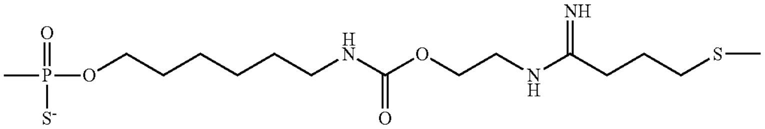
[Chem. 10]
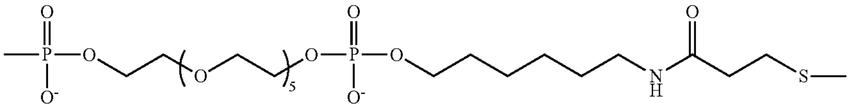
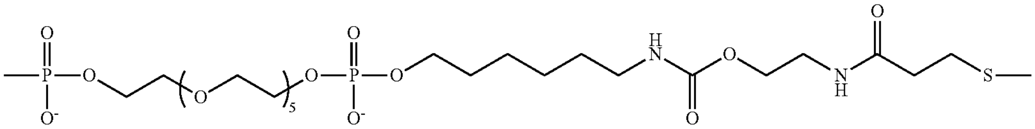
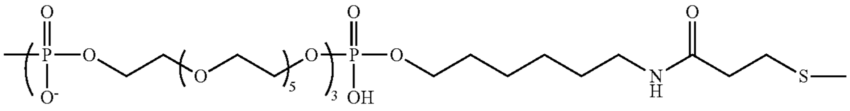

-continued
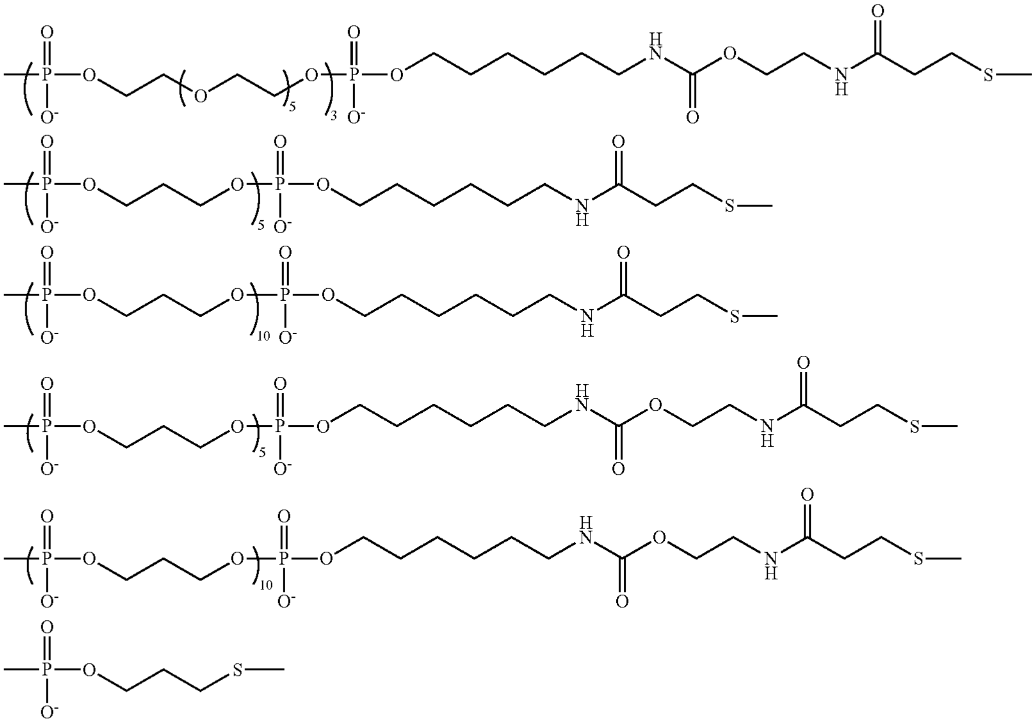
[Chem. 11]
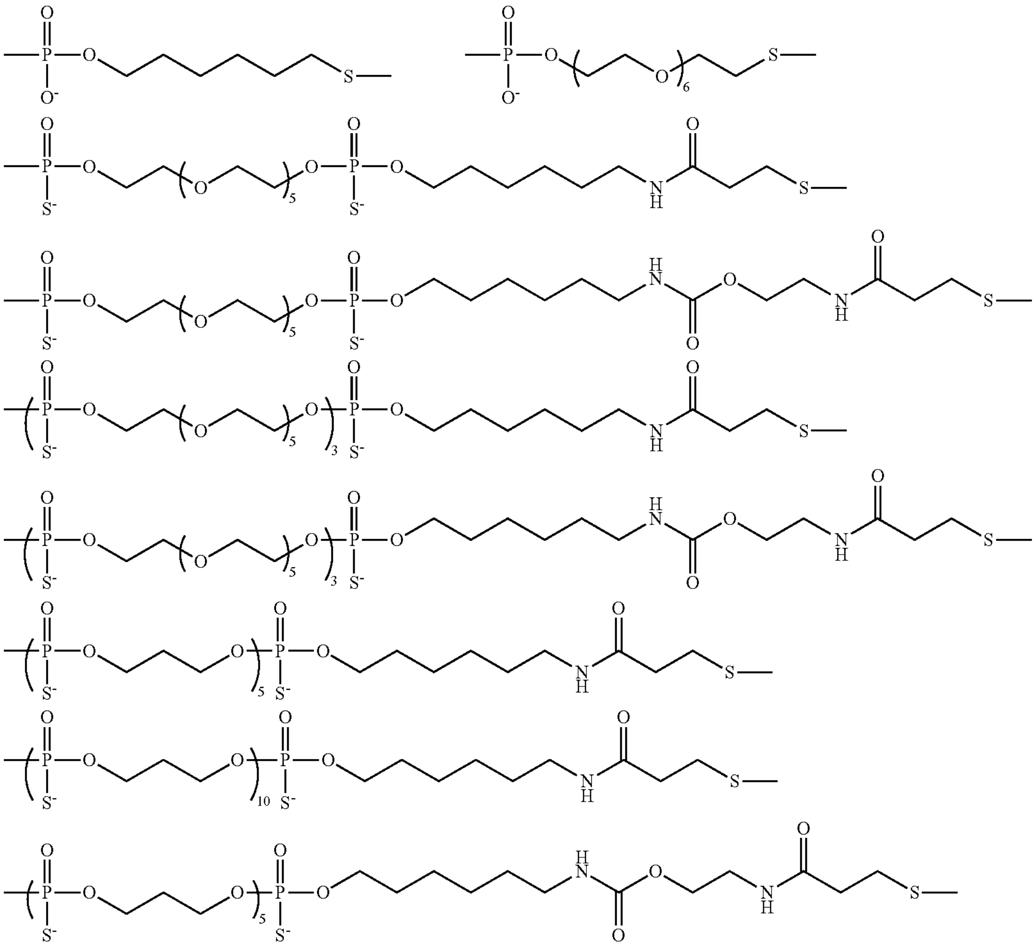

-continued
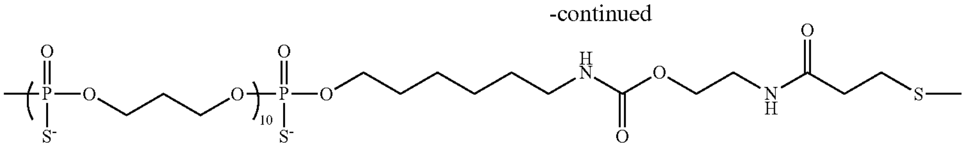
[Chem. 12]
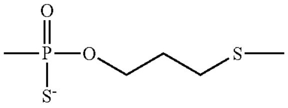
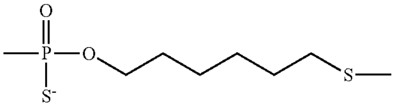
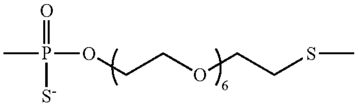
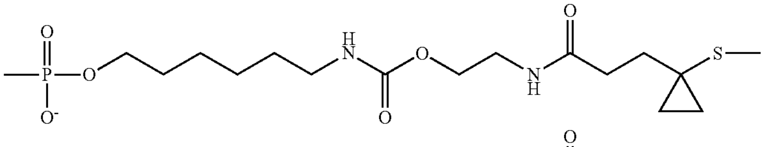
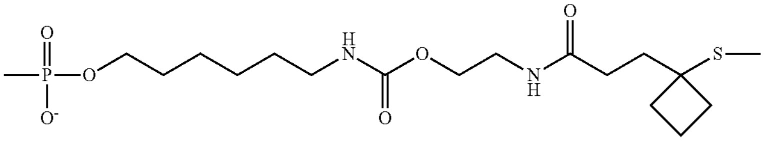
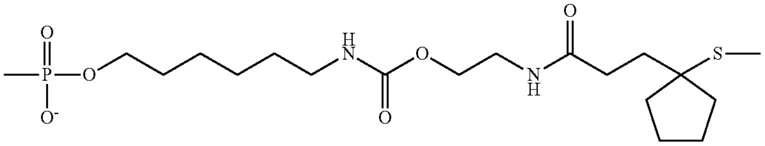
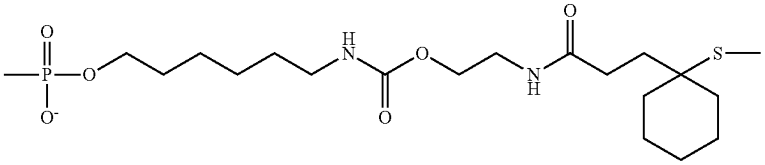
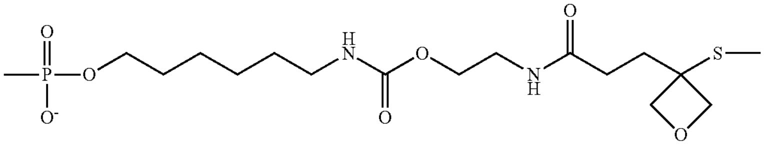
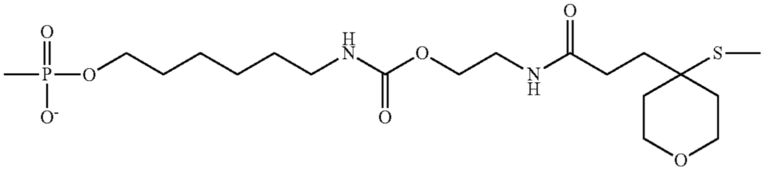
Preferred examples of the spacer Sp include those having any of the following structures.
[Chem. 13]
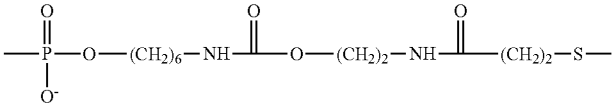
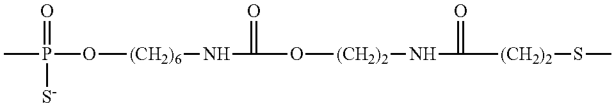
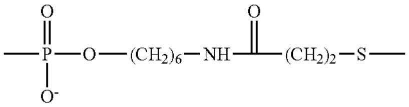
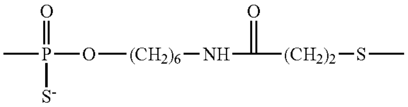

-continued

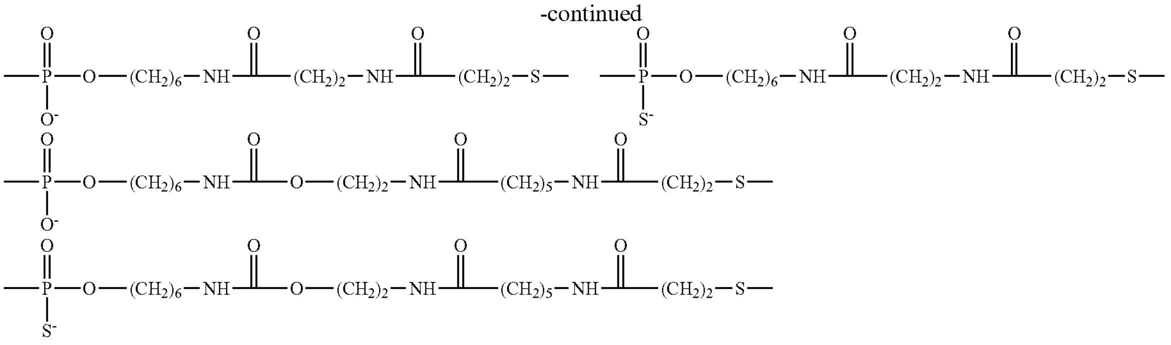

Examples of a combination of reactive functional groups used to form bonding between the spacer and the polynucleotide or polynucleotide derivative or between the spacer and the antigenic peptide include not only a combination of reactive functional groups used to form ester bonds, amide bonds, phosphoester bonds, or the like, but also a combination of reactive functional groups used to immobilize a biomolecule on a biochip surface. More specific examples thereof are detailed below.

(a) Alkyne and an Azide

Alkyne and an azide form a 1,2,3-triazole ring through a cycloaddition reaction (Huisgen reaction) as illustrated below. These compounds, which are stable functional groups capable of being introduced into many organic compounds including biomolecules, react with each other rapidly and nearly quantitatively even in a solvent including water, and generate no unnecessary wastes with little side effects; thus, they are widely used predominantly in so-called "click chemistry" reactions in the field of biochemistry. An alkyne derivative and an azido group can be introduced into an antigenic peptide or a polynucleotide or polynucleotide derivative using any known method. As for the alkyne derivative, those derivatives having a reactive functional group are easily available, such as propargyl alcohols or propargyl amines. By being reacted directly with a reactive functional group such as carboxyl group or hydroxyl group, or reacted with carbonyldiimidazole or the like, such an alkyne derivative can be introduced into an antigenic peptide or a polynucleotide or polynucleotide derivative, through amide bonding, ester bonding, urethane bonding, or other bonding formed by the reaction. The azido group can also be introduced into an antigenic peptide or a polynucleotide or polynucleotide derivative using any known method. Additionally, the Huisgen reaction is performed in the presence of a copper catalyst. However, since antigenic peptides, and polynucleotide derivatives in which the phosphodiester bonds are substituted with sulfur-containing functional groups such as phosphorothioate bonds, contain sulfur atoms coordinating to a copper ion, there may occur a deterioration of the catalytic activity of copper. Thus, it is preferred to add an excess amount of copper for the purpose of increasing the rate of reaction.

[Chem. 14]

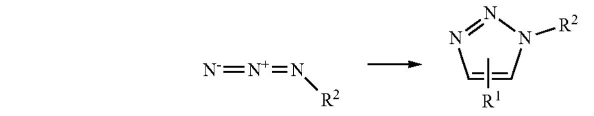

(b) Maleimide or Vinyl Sulfone and a Thiol Group

Maleimide or vinyl sulfone, which has double bonds adjacent to an electron-withdrawing carbonyl or sulfone group, produces a stable thioether derivative at a near-neutral pH through an addition reaction (Michael addition reaction) with a thiol group as illustrated below. Since maleimide and vinyl sulfone derivatives containing a suitable spacer are commercially available, it is easy to introduce such a functional group into an antigenic peptide or a polynucleotide or polynucleotide derivative. In the case of introduction of a thiol group into an antigenic peptide, when the antigenic peptide contains cysteine, a thiol group at the side chain of the cysteine residue can be utilized. However, since cysteine is an amino acid with low abundance ratio, a peptide modified by introducing cysteine toward the N-terminus of an antigenic peptide is used. As the polynucleotide or polynucleotide derivative containing a thiol group, a thiolated polynucleotide in which the hydroxyl group at the 5' end is converted to a thiol group is used.

[Chem. 15]

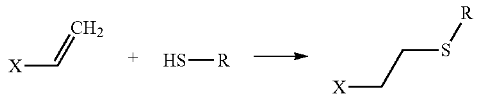

(X: COR' or $SO_2R'$)

(c) Thiol Group at the Side Chain of Cysteine and Thiol Group of a Thiolated Polynucleotide As mentioned above, a thiol group at the side chain of a cysteine residue in an antigenic peptide having cysteine introduced toward the N-terminus thereof is reacted with a thiol group of a thiolated polynucleotide to form a disulfide group. Since the disulfide bonding is cleaved in the presence of a reducing agent, this bonding is inferior in stability over those mentioned in the previous sections. The introduction of a thiol group into a polynucleotide or polynucleotide derivative can be performed using any known method. One specific example of such a method is a reaction of an aminated polynucleotide or polynucleotide derivative with a succinimidyl ester of ω-(2-pyridyldithio) fatty acid as illustrated below.

[Chem. 16]

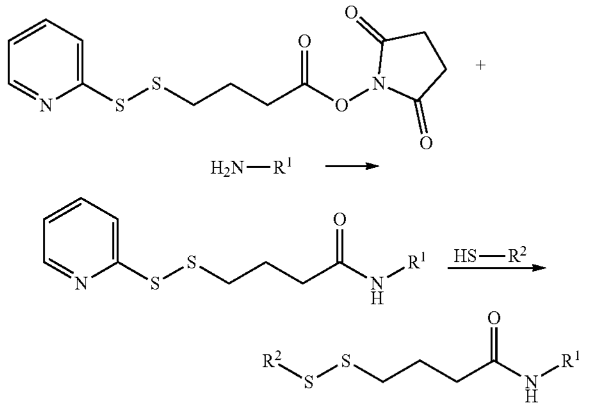

Inter alia, disulfide bonding formed by combination of a thiol group at the side chain of cysteine with a thiol group of a thiolated polynucleotide is preferred since this bonding is easily cleavable in the living body.

The polynucleotide/peptide conjugate used as an active component of the immunity-inducing agent according to this aspect of the present invention can be in a free form or in the form of a pharmaceutically acceptable salt. Examples of pharmaceutically acceptable salts include salts of alkali metals (e.g., potassium, sodium, lithium), salts of alkali earth metals (e.g., calcium, magnesium), ammonium salts (including tetramethylammonium salt, tetrabutylammonium salt), salts of organic amines (e.g., triethylamine, methylamine, dimethylamine, cyclopentylamine, benzylamine, phenethylamine, piperidine, monoethanolamine, diethanolamine, tris(hydroxymethyl)methylamine, lysine, arginine, N-methyl-D-glucamine), and acid adduct salts (including inorganic acid salts such as hydrochloride, hydrobromate, hydroiodide, hydrosulfate, phosphate and nitrate; and organic acid salts such as acetate, trifluoroacetate, lactate, tartrate, oxalate, fumarate, maleate, benzoate, citrate, methanesulfonate (mesylate), ethanesulfonate, benzenesulfonate, toluenesulfonate, isethionate, glucuronate, and gluconate). Further examples of pharmaceutically acceptable salts also include hydrates thereof.

The pharmaceutical composition according to the second aspect of the present invention (hereinafter also simply abbreviated as "pharmaceutical composition") comprises the immunity-inducing agent according to the first aspect of this invention. In order to produce the pharmaceutical composition, the peptide/polynucleotide conjugate as an active component can be used in combination with any known components (any carriers, excipients and additives acceptable for pharmaceutical purposes) and any known pharmaceutical formulation method. In order to produce the pharmaceutical composition comprising an immunity-inducing agent, the peptide/polynucleotide conjugate as an active component can be used in combination with any known components (any carriers, excipients and additives acceptable for pharmaceutical purposes) and any known pharmaceutical formulation method. Examples of pharmaceutical substances include, but are not limited to, the following: amino acids such as glycine, alanine, glutamine, asparagine, arginine or lysine; antioxidants such as ascorbic acid, sodium sulfate or sodium hydrogen sulfite; buffers such as phosphate buffer, citrate buffer, borate buffer, sodium hydrogen carbonate, or Tris-hydrochloride (Tris-HCl) solution; fillers such as mannitol or glycine; chelators such as ethylenediaminetetraacetic acid (EDTA); complexing agents such as caffeine, polyvinylpyrrolidine, β-cyclodextrin or hydroxypropyl-β-cyclodextrin; bulking agents such as glucose, mannose or dextrin; other carbohydrates such as monosaccharides or disaccharides; colorants; flavorants; diluents; emulsifiers; hydrophilic polymers such as polyvinylpyrrolidine; low-molecular-weight polypeptides; salt-forming counterions; preservatives such as benzalkonium chloride, benzoic acid, salicylic acid, thimerosal, phenethyl alcohol, methylparaben, propylparaben, chlorhexidine, sorbic acid or hydrogen peroxide; solvents such as glycerol, propylene glycol or polyethylene glycol; sugar alcohols such as mannitol or sorbitol; suspending agents; surfactants such as sorbitan esters, polysorbates (e.g., polysorbate 20, polysorbate 80), triton, tromethamine, lecithin or cholesterol; stability enhancers such as sucrose or sorbitol; elasticity enhancers such as sodium chloride, potassium chloride, mannitol or sorbitol; transporting agents; excipients; and/or pharmaceutical aids. Such a pharmaceutical substance is preferably added to a pharmaceutical agent in an amount of from 0.01 to 100 times, especially from 0.1 to 10 times, higher than the weight of the pharmaceutical agent. The preferred compositional profile of a pharmaceutical composition prepared as a pharmaceutical preparation can be determined, as appropriate, by any skilled artisan depending on the disease to be treated, the administration route to be applied, and the like.

The pharmaceutical composition is provided in a dosage form suitable for oral or parenteral administration. For example, the pharmaceutical composition is used as an injection, a suppository or the like. Examples of injections include various injection forms such as intravenous injection, subcutaneous injection, intradermal injection, intramuscular injection and drip infusion. Such injections can be prepared according to known methods. With regard to a method for preparing an injection, the injection can be prepared by, for example, dissolving or suspending the polynucleotide/peptide conjugate of the present invention in a sterile aqueous solvent commonly used for injection. Examples of the aqueous solvent for injection that can be used include distilled water, physiological saline, a buffer such as phosphate buffer, carbonate buffer, Tris buffer or acetate buffer, or the like. The pH of such an aqueous solvent is in the range of from 5 to 10, preferably from 6 to 8. The prepared injection is preferably filled in an appropriate ampule. The injection may be made into a freeze-dried formulation. As for other dosage forms besides injections, the pharmaceutical composition can be provided in a dosage form for transdermal or transmucosal absorption (e.g., liquid spray, ointment, gel, lotion, patch), in a subcutaneous, local, sustained-release dosage form (e.g., suspension containing a nanogel, a biodegradable micro/nano-capsule, etc., temperature-responsive gel), or in the form of a pharmaceutical preparation accompanied with a percutaneous device for skin permeation (e.g., iontophoresis, microneedle), a powder, a tablet, a capsule, a syrup, or an inhalant such as aerosol or dry powder.

The pharmaceutical composition may further comprise a substance having immunostimulatory activity as an adjuvant. The adjuvant is, but not limited to, a substance that activates innate immunity. The adjuvant is preferably an agonist of an innate immunity receptor. Examples of innate immunity receptor agonists include TLR agonists (e.g., TLR2 agonist, TLR3 agonist, TLR4 agonist, TLR7 agonist, TLR8 agonist, TLR9 agonist), RLR (retinoic acid-inducible gene I (RIG-1)-like receptors) agonists, STING (stimulator of Interferon genes) agonists, NLR (nucleotide-binding oligomerization domain (NOD)-like receptors) agonists, and CLR (C-type lectin receptors) agonists. Examples of TLR agonists include lipopeptide, Poly IC RNA, imiquimod, resiquimod, monophosphoryl lipid (MPL), CpG-ODN, and the like. Examples of RLR agonists include pppRNA, Poly IC RNA, and the like. Examples of STING agonists include cGAMP, c-di-AMP, c-di-GMP, and the like. Examples of NLR agonists include iE-DAP, FK565, MDP, murabutide, and the like. Examples of CLR agonists include B-glucan, trehalose-6,6'-dimycolate, and the like. The adjuvant is preferably a TLR agonist, more preferably TLR4 agonist, TLR7 agonist or TLR9 agonist, still more preferably imiquimod, resiquimod, MPL or CpG-ODN. In some embodiments, the adjuvant is imiquimod, MPL or CpG-ODN. The adjuvant is selected as appropriate depending on the type of an antigenic peptide introduced into the peptide/polynucleotide conjugate, or the like. For example, the adjuvant can be CpG DNA or the like, or can be a polynucleotide/β-1,3-glucan complex, as disclosed in International Patent Publication No. WO 2015/118789, which is formed by binding a polynucleotide or polynucleotide derivative containing a partial nucleotide sequence having immunostimulatory activity to a polysaccharide having a β-1,3-glucan backbone via hydrogen bonding, and which has a triple helix structure consisting of one molecular chain of the polynucleotide or polynucleotide derivative and two molecular chains of the polysaccharide having a β-1,3-glucan backbone.

The pharmaceutical composition can be administered to a human or a warm-blooded animal (e.g., mouse, rat, rabbit, sheep, pig, cow, horse, chicken, cat, dog, monkey) by any of oral and parenteral routes. Examples of parenteral routes include subcutaneous, intracutaneous and intramuscular injections, intraperitoneal administration, drip infusion, and spray into nasal mucosa or pharyngeal region.

The dose of the peptide/polynucleotide conjugate serving as an active component of the pharmaceutical composition differs according to activity, the disease to be treated, the type, body weight, sex and age of an animal to be medicated, the severity of a disease, administration method, and/or the like. As an example, in the case of medication of an adult human with a body weight of 60 kg, the daily dose for oral administration is generally in the range of from about 0.1 to about 100 mg, preferably from about 1.0 to about 50 mg, more preferably from about 1.0 to about 20 mg, and the daily dose for parenteral administration is generally in the range of from about 0.01 to about 30 mg, preferably from about 0.1 to about 20 mg, more preferably from about 0.1 to about 10 mg. When the pharmaceutical composition is administered to other animals, the dose to be used for such animals is calculated by converting the aforementioned dose into a dose per unit body weight and multiplying the dose per unit body weight by the body weight of an animal to be medicated.

By administering the pharmaceutical composition according to this aspect of the present invention to a patient with a pathogenic infection or a cancer, or a subject predisposed to suffering from a cancer or a pathogenic infection, cytotoxic T lymphocytes (CTLs) present in the medicated patient or subject are activated in an antigen-specific manner to induce antigen-specific antibody production, or namely to induce a protective immune response of a warm-blooded animal (preferably a human), thereby enabling prevention or treatment of the infection or cancer. In other words, the pharmaceutical composition according to this aspect of the invention is useful as a vaccine for the prevention or treatment of diseases such as infections or cancers as mentioned above. In this invention, the terms "tumor(s)" and "cancer(s)" are exchangeably used. Also, in this invention, tumors, malignant tumors, cancers, malignant neoplasms, carcinomas, sarcomas and the like may be collectively referred to as "tumors" or "cancers". Further, the terms "tumor(s)" and "cancer(s)" may in some cases include pathological conditions classified as pre-cancer stages, such as myelodysplastic syndromes.

The types of tumors to be treated are not particularly limited as long as they are tumors proved to be susceptible to the pharmaceutical composition of the present invention. Examples of tumors to be treated include breast cancer, colon cancer, prostate cancer, lung cancer (including small-cell lung cancer, non-small-cell lung cancer, etc.), stomach cancer, ovarian cancer, cervical cancer, endometrial cancer, corpus uteri cancer, kidney cancer, hepatocellular cancer, thyroid cancer, esophageal cancer, osteosarcoma, skin cancer (including melanoma, etc.), glioblastoma, neuroblastoma, ovarian cancer, head and neck cancer, testicular tumor, bowel cancer, blood cancer (including leukemia, malignant lymphoma, multiple myeloma, etc.), retinoblastoma, pancreatic cancer, and the like.

The pharmaceutical composition according to this aspect of the present invention may be used in combination with other antitumor agents. Examples of other antitumor agents include antitumor antibiotics, antitumor plant extracts, BRMs (biological response modifiers), hormones, vitamins, antitumor antibodies, molecular targeted drugs, alkylating agents, metabolic antagonists, other antitumor agents, and the like.

More specifically, examples of alkylating agents include alkylating agents such as nitrogen mustard, nitrogen mustard N-oxide, bendamustine or chlorambucil; aziridine-based alkylating agents such as carboquone or thiotepa; epoxide-based alkylating agents such as dibromomannitol or dibromodulcitol; nitrosourea-based alkylating agents such as carmustine, lomustine, semustine, nimustine hydrochloride, streptozocin, chlorozotocin or ranimustine; other alkylating agents such as busulfan, improsulfan tosilate, temozolomide or dacarbazine, and the like.

Examples of metabolic antagonists include purine metabolic antagonists such as 6-mercaptopurine, 6-thioguanine or thioinosine; pyrimidine metabolic antagonists such as fluorouracil, tegafur, tegafur-uracil, carmofur, doxifluridine, broxuridine, cytarabine or enocitabine; folate metabolic antagonists such as methotrexate or trimetrexate, and the like.

Examples of antitumor antibiotics include mitomycin C, bleomycin, peplomycin, daunorubicin, aclarbicin, doxorubicin, idarubicin, pirarubicin, THP-adriamycin, 4'-epi-doxorubicin or epirubicin, chromomycin A3 or actinomycin D, and the like.

Examples of antitumor plant extracts and derivatives thereof include vinca alkaloids such as vindesine, vincristine or vinblastine; taxanes such as paclitaxel, docetaxel or cabazitaxel; or epipodophyllotoxins such as etoposide or teniposide, and the like.

Examples of BRMs include tumor necrosis factors or indomethacin, and the like.

Examples of hormones include hydrocortisone, dexamethasone, methylprednisolone, prednisolone, prasterone, betamethasone, triamcinolone, oxymetholone, nandrolone, metenolone, fosfestrol, ethinylestradiol, chlormadinone, mepitiostane or medroxyprogesterone, and the like.

Examples of vitamins include vitamin C or vitamin A, and the like.

Examples of antitumor antibodies or molecular targeted drugs include trastuzumab, rituximab, cetuximab, panitumumab, nimotuzumab, denosumab, bevacizumab, infliximab, ipilimumab, nivolumab, pembrolizumab, avelumab, pidilizumab, atezolizumab, ramucirumab, imatinib mesylate, dasatinib, sunitinib, lapatinib, dabrafenib, trametinib, cobimetinib, pazopanib, palbociclib, panobinostat, sorafenib, crizotinib, vemurafenib, kizaruchinib, bortezomib, carfilzomib, ixazomib, midostaurin, gilteritinib, and the like.

Examples of other antitumor agents include cisplatin, carboplatin, oxaliplatin, tamoxifen, letrozole, anastrozole, exemestane, toremifene citrate, fulvestrant, bicalutamide, flutamide, mitotane, leuprorelin, goserelin acetate, camptothecin, ifosfamide, cyclophosphamide, melphalan, L-asparaginase, aceglatone, schizophyllan, picibanil, procarbazine, pipobroman, neocarzinostatin, hydroxyurea, ubenimex, thalidomide, lenalidomide, pomalidomide, eribulin, tretinoin or krestin, and the like.

Examples of infections to be treated include infections with pathogens such as viruses, fungi or bacteria. Examples of viruses include influenza virus, hepatitis virus, human immunodeficiency virus (HIV), RS virus, rubella virus, measles virus, epidemic parotitis virus, herpesvirus, poliovirus, rotavirus, Japanese encephalitis virus, varicella virus, adenovirus, rabies virus, yellow fever virus, and the like. Examples of bacteria include *Corynebacterium diphtheriae, Clostridium tetani, Bordetella pertussis, Hemophilus influenza, Mycobacterium tuberculosis, Streptococcus pneumoniae, Helicobacter pylori, Bacillus anthracis, Salmonella typhosa, Neisseria meningitidis, Bacillus dysenteriae, Vibrio cholerae*, and the like. Examples of fungi include fungi of the genus *Candida*, fungi of the genus *Histoplasma*, fungi of the genus *Cryptococcus*, fungi of the genus *Aspergillus*, and the like. The pharmaceutical composition of the present invention may be used in combination with existing therapeutic agents for such infections.

Administration of the pharmaceutical composition of this aspect of the present invention in combination with an adjuvant or other drugs means ingestion of both of the drugs into the body of a medicated subject within a certain period of time. A single preparation incorporating both of the drugs may be administered, or both of the drugs may be formulated into separate preparations and administered separately. When both of the drugs are formulated into separate preparations, the timings of administration of the separate preparations are not particularly limited, and they may be administered simultaneously or may be sequentially administered at intervals of times or days. When separate preparations are administered at different times or on different days, the order of their administration is not particularly limited. Since separate preparations are generally administered according to their respective administration methods, the numbers of doses of these preparations may be the same or different. Also, when both of the drugs are formulated into separate preparations, the separate preparations may be administered by the same administration method (via the same administration route) or by different administration methods (via different administration routes). Further, both of the drugs are not necessarily present simultaneously in the body, and it is only necessary that both of the drugs should be ingested into the body within a certain period of time (e.g., for one month, preferably for one week, more preferably for a few days, still more preferably for one day). The active component of one preparation may be eliminated from the body at the time of administration of the other preparation.

EXAMPLES

Next, the following describes working examples conducted to confirm the actions and effects of the present invention. As referred to in the following examples, the term “CpG DNA(S)” refers to a DNA derivative (an example of polynucleotide derivative) which has a nucleotide sequence comprising a CpG motif(s) and in which phosphodiester bonds are substituted with phosphorothioate bonds. In the chemical structural formulas shown in the following examples, the nucleotide sequences of polynucleotide derivatives are written in single letter codes with the 5' end to the left (and the 3' end to the right), and the amino acid sequences of peptides, except for cysteine at the N-terminus, are written in three letter codes with the N-terminus to the left (and the C-terminus to the right). In the polynucleotide derivatives written in single letter codes, all phosphodiester bonds are substituted with phosphorothioate bonds, and their termini end with an oxygen atom at the 5'- or 3'-hydroxy group of the terminal nucleoside when coupled to a spacer, or end with the entire 5'- or 3'-hydroxy group (including a hydrogen atom) of the terminal nucleoside when not coupled to a spacer. Further, in the following examples, the CpG DNA(S)-peptide conjugate was prepared in the form of a salt having triethylamine and acetic acid added thereto.

Example 1: Preparation of a CpG DNA(S)-Peptide Conjugate

One mol of amino group-modified CpG DNA(S) synthesized by a given method known in the art (a CpG DNA(S) derivative having introduced at its 5' end an amino group with a structure represented by the following formula; nucleotide sequence:

(SEQ ID NO: 229
ATCGACTCTCGAGCGTTCTCATCGACTCTCGAGCGTTCTC;

hereinafter abbreviated as “CpG40 (S)”); all phosphodiester bonds were substituted with phosphorothioate bonds) was mixed with 30 mol of succinimidyl 6-[3'-(2-pyridyldithio)-propionamido]hexanoate (LC-PDP) in a phosphate buffer (pH 8.0). After being left to stand at 40° C. for 3 hours, SPDP-modified CpG DNA(S) was purified using a NAP-5 column.

[Chem. 17]

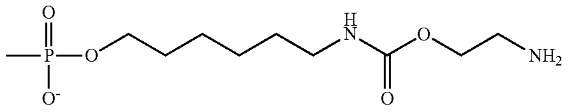

Hereinafter, the structure represented by the following formula is abbreviated as “ssH amino linker”.

[Chem. 18]

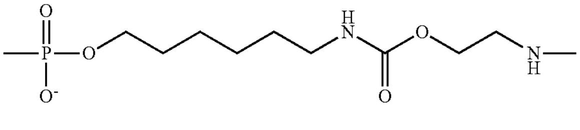

A peptide (amino acid sequence: CSIINFEKL (SEQ ID NO: 250; hereinafter abbreviated as "OVApep9")) having cysteine added toward the N-terminus of an ovalbumin (OVA)-derived antigenic peptide (257th to 264th amino acids (amino acid sequence: SIINFEKL (SEQ ID NO:196))) was mixed at a ratio of 25 mol to 1 mol of the SPDP-modified CpG DNA(S) in an aqueous solution of 30% N,N-dimethylformamide (DMF). After being left to stand at 40° C. for 3 hours, the mixture was fractionated by HPLC to obtain a CpG DNA(S)-peptide conjugate. HPLC was performed under the following gradient conditions using 0.1 M triethylammonium acetate (TEAA; pH 7.0) and acetonitrile as solvents A and B, respectively, and the column ZORBAX Eclipse Plus C18.

| | | |
|---|---|---|
| 0 min | A: 90% | B: 10% |
| to 25 min | A: 70% | B: 30% |
| to 30 min | A: 0% | B: 100% |

During the process of the HPLC fractionation of the solution obtained after the reaction of SPDP-modified CpG DNA(S) with the OVA-derived peptide, detection was performed by monitoring the absorption at 260 nm for dA40 (S). It was observed that the elution time of the peak of the fractionated CpG DNA(S)-peptide conjugate was delayed as compared to that of SPDP-modified CpG DNA(S). This is considered to be because the elution time became later since SPDP-modified CpG DNA(S) was bound to the hydrophobic peptide. Further, in the chromatogram obtained from the fractionation, no peak for unreacted SPDP-modified CpG DNA(S) was observed, and only the peak for the CpG DNA(S)-peptide conjugate was detected—this fact confirmed that the CpG DNA(S)-peptide conjugate of interest (CpG40 (S)-OVApep9 conjugate; see below for its structural formula) was obtained in high purity.

CFSE was varied such that the fluorescence intensity of the antigen-retaining splenocytes (CFSE: 5 μM) was higher than that of the non-antigen-retaining splenocytes (CFSE: 0.5 μM). The same numbers of the antigen-retaining and non-antigen-retaining splenocytes were mixed together, and administered via tail vain to the mice administered the CpG DNA(S)-peptide conjugate as an antigen, after one week of administration. The dose of the CpG DNA(S)-peptide conjugate was 20 ng per mouse in terms of peptide (250 ng in terms of CpG40 (S)).

After the lapse of 24 hours from the tail vein administration, splenocytes were isolated from the mice, and evaluated for induced cytotoxic T lymphocyte activity through flow cytometrically quantifying the percentages of antigen-retaining and non-antigen-retaining splenocytes to determine the amount of decrease in antigen-retaining splenocytes. The results of the flow cytometric analysis are shown in FIG. 1(FIG. 1(*b*)). For comparison's sake, the results of the flow cytometric analysis conducted for the control groups under the same conditions are also shown in FIG. 1; as the control groups, other mice were either administered PBS (phosphate-buffered saline) (FIG. 1(*a*)) or separately administered the antigenic peptide and CpG DNA(S) (FIG. 1(*c*)), instead of the CpG DNA(S)-peptide conjugate.

As shown in FIG. 1(*a*), the splenocytes collected from the mice administered PBS contained the same numbers of antigen-retaining and non-antigen-retaining splenocytes. However, as shown in FIG. 1(*b*), about 95% of antigen-retaining splenocytes disappeared from the splenocytes collected from the mice administered the CpG DNA(S)-peptide conjugate. This revealed that administration of the CpG DNA(S)-peptide conjugate resulted in induction of a peptide antigen-specific immune response. Also, by comparison with FIG. 1(*c*), it was found that the effect of administration

[Chem. 19]

CpG40(S) (SEQ ID NO:229)

ATCGACTCTCGAGCGTTCTCATCGACTCTCGAGCGTTCTC

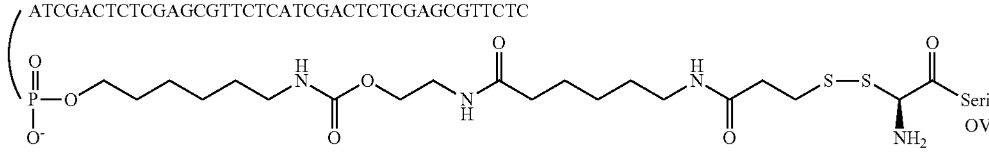

SerIleIleAsnPheGluLysLeu

OVApep9 (SEQ ID NO:250)

of the CpG DNA(S)-peptide conjugate was higher than that of separate administration of the antigenic peptide and CpG DNA(S).

Example 2: Evaluation of Induction of Cytotoxic T Lymphocytes by CpG DNA(S)-Peptide Conjugate The CpG DNA(S)-peptide conjugate was intracutaneously administered as an antigen to mice (C57BL/6 mice (♀, 7 weeks old)) (once at 20 ng per mouse). After one week of administration, splenocytes were isolated from those mice of the same strain not receiving administration, and divided into two groups. To one group, an ovalbumin (egg albumin, OVA)-derived antigenic peptide (peptide sequence: SIINFEKL (SEQ ID NO: 196)) was added, and the mixture was left to stand for 90 minutes to prepare antigen-retaining splenocytes. The other group of splenocytes not receiving addition of the peptide was regarded as non-antigen-retaining splenocytes. Both of the antigen-retaining splenocytes and the non-antigen-retaining splenocytes were fluorescently modified with 5,6-carboxyfluorescein succinimidyl ester (CFSE). During this process, the concentration of

Example 3: Dependence on the Dose of a CpG DNA(S)-Peptide Conjugate

Mice were immunized with varied doses of the CpG DNA(S)-peptide conjugate. Then, as in Example 2, the same numbers of antigen-retaining and non-antigen-retaining splenocytes were mixed together, and administered via tail vain to the mice administered the CpG DNA(S)-peptide conjugate. Thereafter, splenocytes were isolated from the mice, and evaluated for induced cytotoxic T lymphocyte activity through flow cytometrically quantifying the percentages of antigen-retaining and non-antigen-retaining splenocytes to determine the amount of decrease in antigen-retaining splenocytes.

Figure 2:
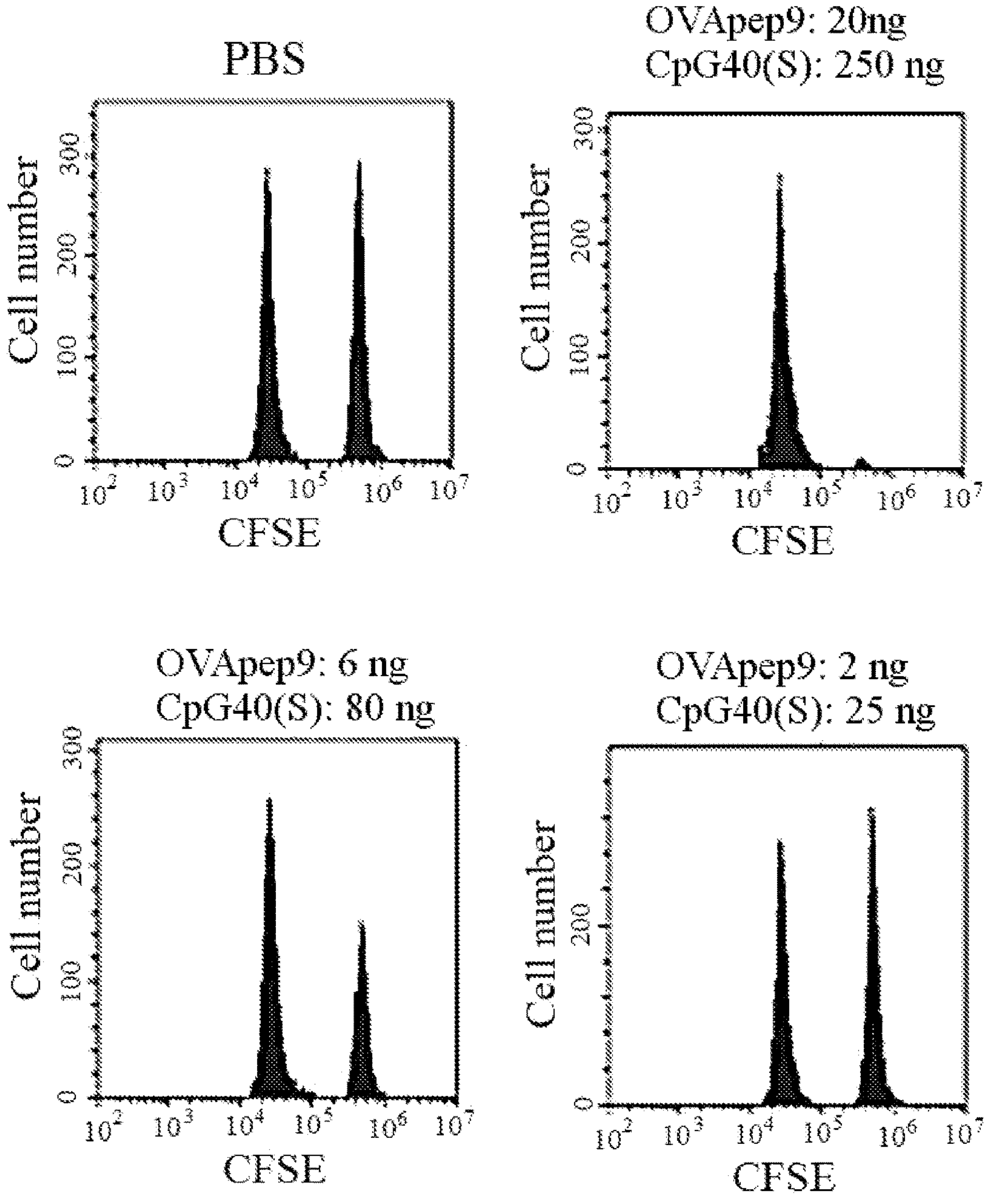
FIG. 2 depicts the results of the flow cytometric analysis performed in Example 3.

The results of the flow cytometric analysis are shown in FIG. 2. It was found that as the dose of the CpG DNA(S)-peptide conjugate was decreased to less than 20 ng in terms of peptide, the effect of the conjugate diminished gradually. In general, peptide immunization requires administration of the peptide at a dose of several micrograms. However, by the use of the CpG DNA(S)-peptide conjugate prepared in Example 1, the peptide dose was successfully reduced to a hundredth to a thousandth.

Example 4: Dependence on the Nucleotide Length and Nucleotide Sequence of CpG DNA(s) Contained in a CpG DNA(S)-Peptide Conjugate Different CpG DNA(S)-peptide conjugates were prepared by the same procedure as in Example 1, except that the 40-nucleotide-long CpG DNA(S) derivative (nucleotide sequence: ATCGACTCTCGAGCGTTCTCATCGACTCTCGAGCGTTCTC (SEQ ID NO: 229; hereinafter abbreviated as "CpG40 (S)")), which was used to prepare a CpG DNA(S)-peptide conjugate in Example 1, was replaced with any of the following CpG DNA(S) derivatives: 30-nucleotide-long CpG DNA(S) derivatives (nucleotide sequence:

GAGCGTTCTCATCGACTCTCGAGCGTTCTC (SEQ ID NO: 227; hereinafter abbreviated as "CpG30 (S) a"), and nucleotide sequence:

ATCGACTCTCGAGCGTTCTCGAGCGTTCTC (SEQ ID NO: 228; hereinafter abbreviated as "CpG30 (S) b")); a 24-nucleotide-long CpG DNA(S) derivative (nucleotide sequence:

TCTCGAGCGTTCTCGAGCGTTCTC (SEQ ID NO: 225; hereinafter abbreviated as "CpG24 (S)")); and 20-nucleotide-long CpG DNA(S) derivatives (nucleotide sequence:

ATCGACTCTCGAGCGTTCTC (SEQ ID NO: 222; hereinafter abbreviated as "CpG20 (S) a", and nucleotide sequence: GAGCGTTCTCGAGCGTTCTC (SEQ ID NO: 223; hereinafter abbreviated as "CpG20 (S) b")) (see below for their structural formulas) (as for the structural formulas and nucleotide sequences of these derivatives, see the structural formulas and Table 9 shown below; the nucleotide sequences indicated in boldface with underline in Table 9 are CpG motifs; all phosphodiester bonds were substituted with phosphorothioate bonds).

TABLE 9

| Abbreviated name | Nucleotide sequence | SEQ ID NO. |
|---|---|---|
| CpG40(S) | ATCGACTCTCG**AGCGTT**CTCATCGACTCTCG**AGCGTT**CTC | 229 |
| CpG30(S)a | G**AGCGTT**CTCATCGACTCTCG**AGCGTT**CTC | 227 |
| CpG30(S)b | ATCGACTCTCG**AGCGTT**CTCG**AGCGTT**CTC | 228 |
| CpG24(S) | TCTCG**AGCGTT**CTCG**AGCGTT**CTC | 225 |
| CpG20(S)a | ATCGACTCTCG**AGCGTT**CTC | 222 |
| CpG20(S)b | G**AGCGTT**CTCG**AGCGTT**CTC | 223 |

[Chem. 20]

CpG20(S)a (SEQ ID NO: 222)

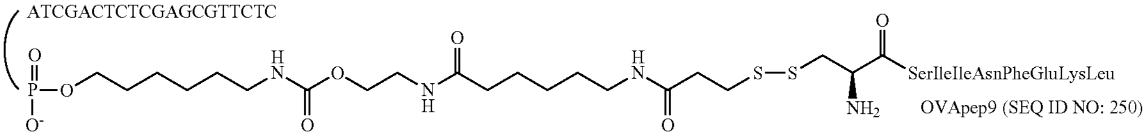

[Chem. 21]

CpG20(S)b (SEQ ID NO: 223)

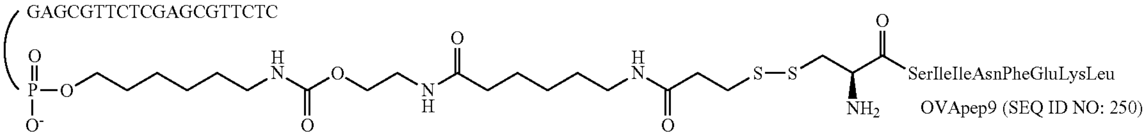

[Chem. 22]

CpG24(S) (SEQ ID NO: 225)

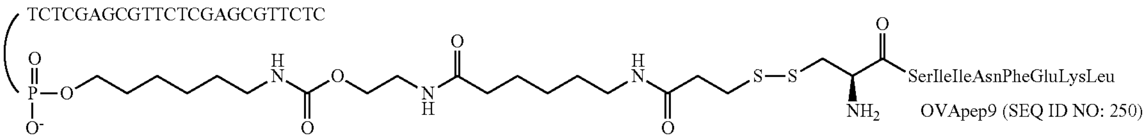

-continued

[Chem. 23]

CpG30(S)a (SEQ ID NO: 227)

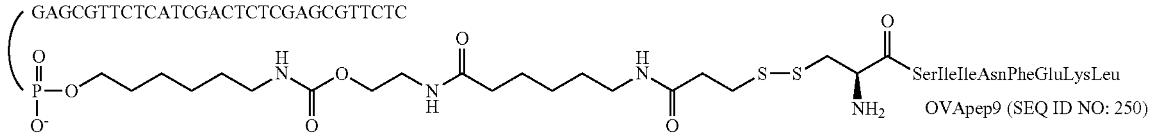

OVApep9 (SEQ ID NO: 250)

[Chem. 24]

CpG30(S)b (SEQ ID NO: 228)

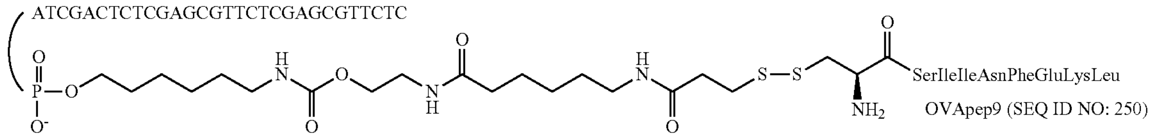

OVApep9 (SEQ ID NO: 250)

Mice were immunized with the different CpG DNA(S)-peptide conjugates comprising different nucleotide lengths of CpG DNA(S) (20 ng per mouse in terms of peptide), and then, as in Example 2, administered a mixture of antigen-retaining and non-antigen-retaining splenocytes by tail vein injection and evaluated for induced cytotoxic T lymphocyte activity through flow cytometrically quantifying the percentages of antigen-retaining and non-antigen-retaining splenocytes to determine the amount of decrease in antigen-retaining splenocytes.

Figure 3:
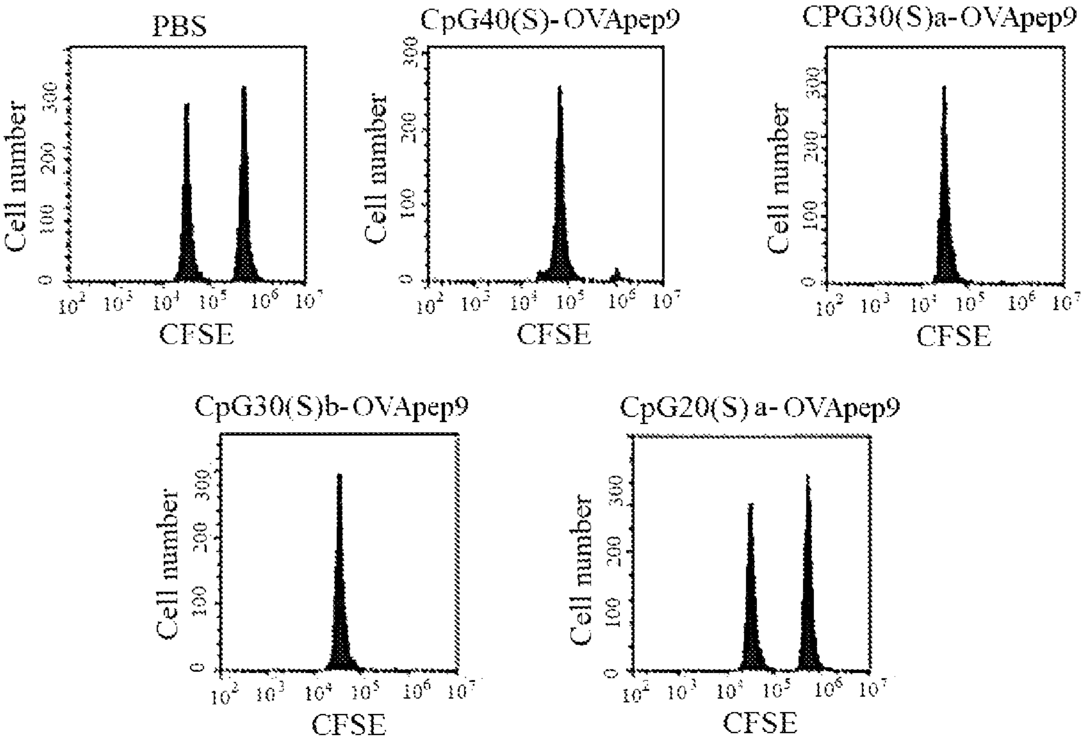
FIG. 3 depicts the results of the flow cytometric analysis performed in Example 4.
Figure 4:
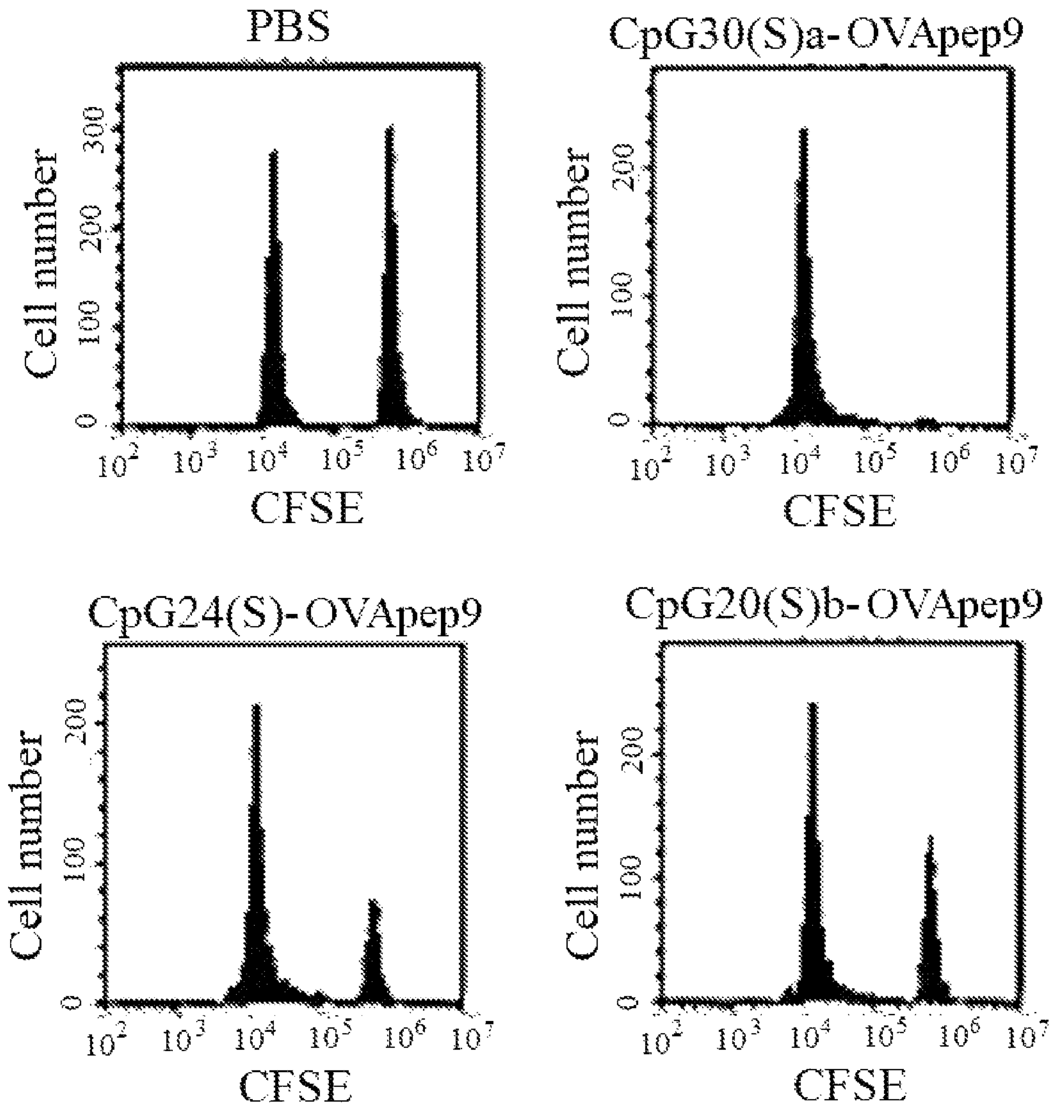
FIG. 4 depicts the results of the flow cytometric analysis performed in Example 4.

The results of the flow cytometric analysis are shown in FIGS. 3 and 4. It was found that even in the case of CpG DNA(S) shorten to 30 nucleotides, antigen-retaining splenocytes completely disappeared. With regard to CpG DNA (S) shorten to 20 nucleotides, no decrease in the number of antigen-retaining splenocytes was observed in the case of CpG DNA(S) containing only a single CpG motif, whereas a decrease in the number of antigen-retaining splenocytes was observed in the case of CpG DNA(S) containing two CpG motifs, which indicates that the activity of peptide-specific cytotoxic T lymphocytes was induced.

Example 5: Dependence on the Amino Acid Length of a Peptide Contained in a CpG DNA(S)-Peptide Conjugate Different CpG DNA(S)-peptide conjugates were prepared using a 18-amino acid-long peptide (amino acid sequence: CEVSGLEQLESIINFEKL (SEQ ID NO: 251; hereinafter abbreviated as "OVApep18")) or a 27-amino acid-long peptide (amino acid sequence: CMSMLVLLPDEVSGLEQLESIINFEKL (SEQ ID NO: 252; hereinafter abbreviated as "OVApep27")), which were generated by extending the antigenic peptide used in the CpG DNA(S)-peptide conjugate of Example 1 in a direction toward the N-terminus (see below for the structural formulas of the two conjugates). Mice were immunized with the different CpG DNA(S)-peptide conjugates (20 ng per mouse in terms of peptide), and then, as in Example 2, administered a mixture of antigen-retaining and non-antigen-retaining splenocytes by tail vein injection and evaluated for induced cytotoxic T lymphocyte activity through flow cytometrically quantifying the percentages of antigen-retaining and non-antigen-retaining splenocytes to determine the amount of decrease in antigen-retaining splenocytes.

[Chem. 25]

CpG40(S) (SEQ ID NO: 229)

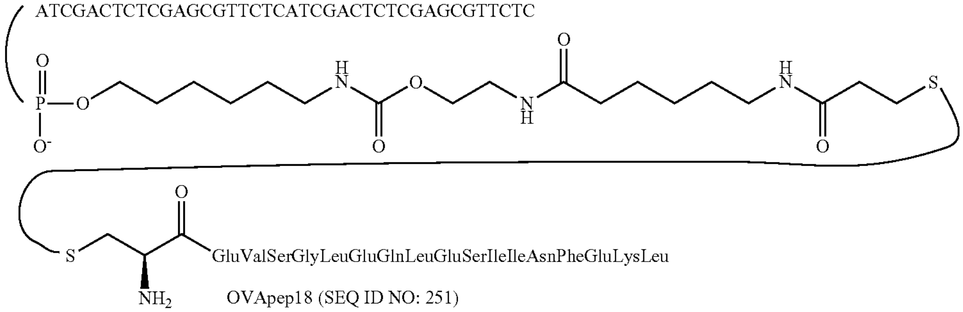

OVApep18 (SEQ ID NO: 251)

-continued

[Chem. 26]

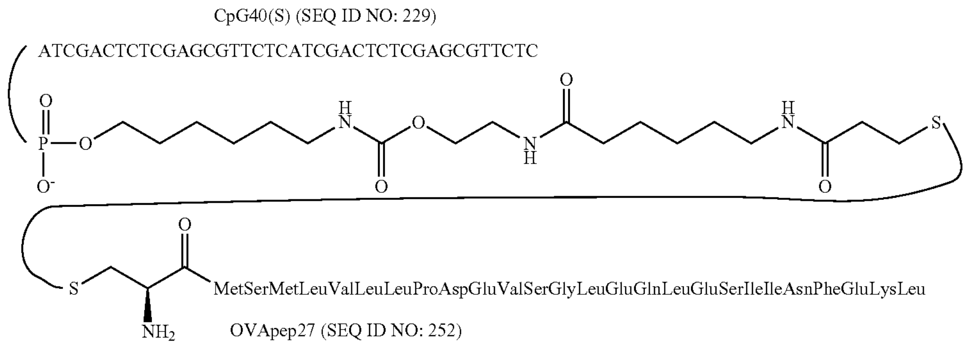

CpG40(S) (SEQ ID NO: 229)

OVApep27 (SEQ ID NO: 252)

Figure 5:
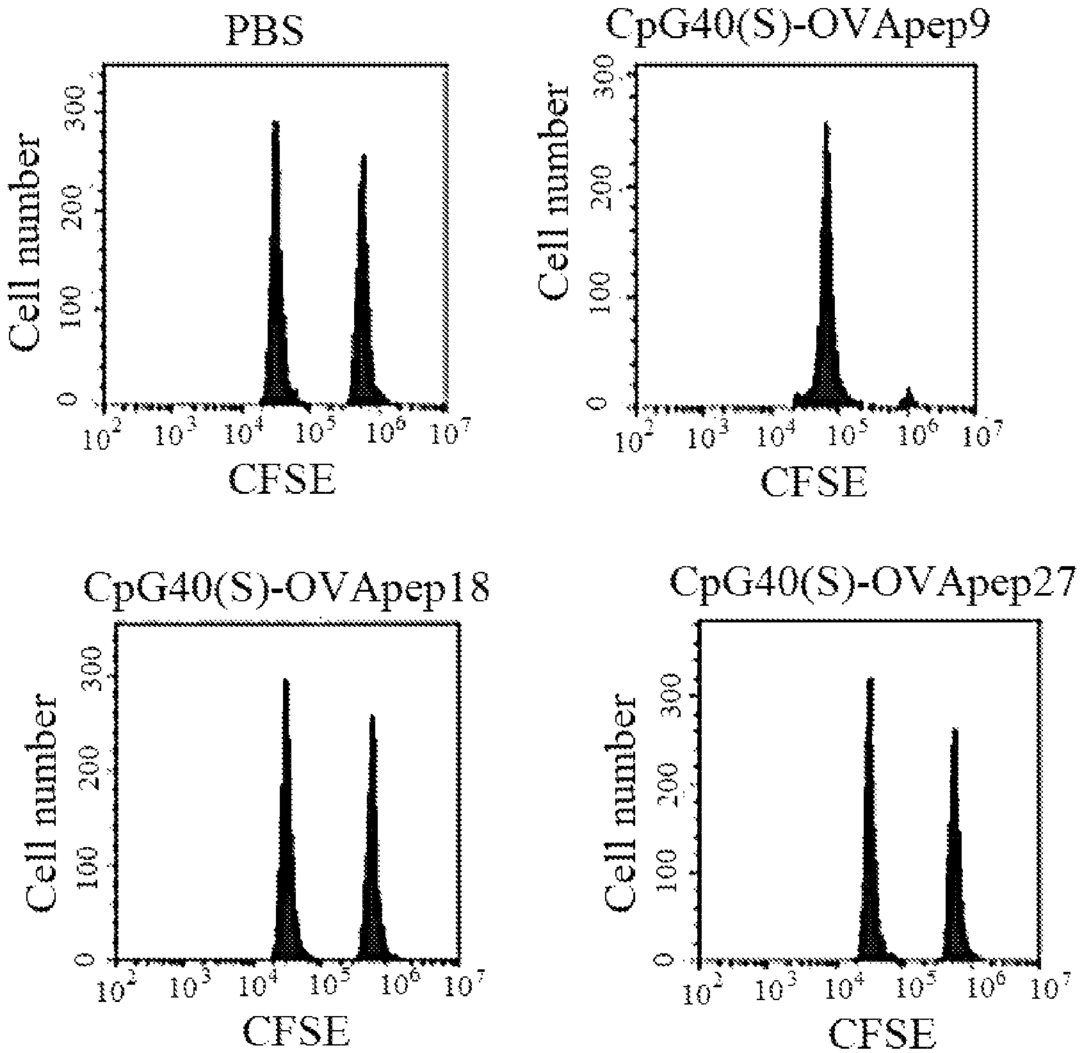
FIG. 5 depicts the results of the flow cytometric analysis performed in Example 5.

The results of the flow cytometric analysis are shown in FIG. 5. It was observed that the activity of peptide-specific cytotoxic T lymphocytes tends to decrease when the length of the antigenic peptide is extended to 18 or 27 amino acids.

Example 6: Dependence on the Spacer Structure and the Conjugation Site of Peptide in a CpG DNA(S)-Peptide Conjugate Evaluation of induced cytotoxic T lymphocyte activity was conducted by the same procedure as in Example 2 by using three different CpG DNA(S)-peptide conjugates as detailed below: a CpG DNA(S)-peptide conjugate which was prepared using an amino linker with the structure shown below (hereinafter abbreviated as "C6 amino linker") instead of the ssH amino linker used to prepare the CpG DNA(S)-peptide conjugate of Example 1 (hereinafter referred to as "Compound (I)"); a CpG DNA(S)-peptide conjugate in which a PEGylated C18 spacer was inserted between CpG DNA(S) and the ssH amino linker; and a CpG DNA(S)-peptide conjugate in which an antigenic peptide was covalently bound to the 3' end, not to the 5' end, of CpG DNA(S) via the same spacer structure as used in Compound (I). As a result, it was observed that immunization with any of these conjugates resulted in induction of potent peptide-specific cytotoxic T lymphocyte activity to comparable levels to immunization with the CpG DNA(S)-peptide conjugate prepared in Example 1.

[Chem. 27]

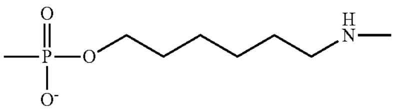

[Chem. 28]

(I)

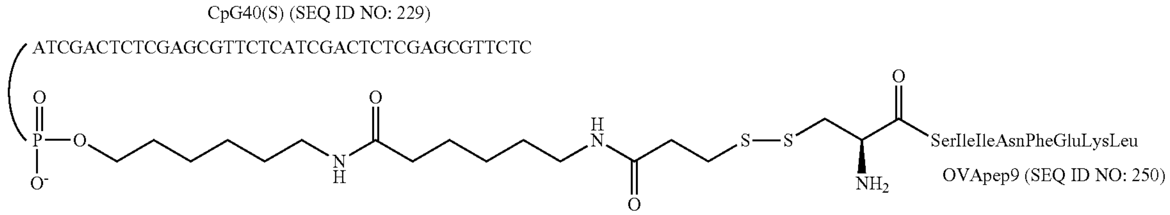

CpG40(S) (SEQ ID NO: 229)

OVApep9 (SEQ ID NO: 250)

[Chem. 29]

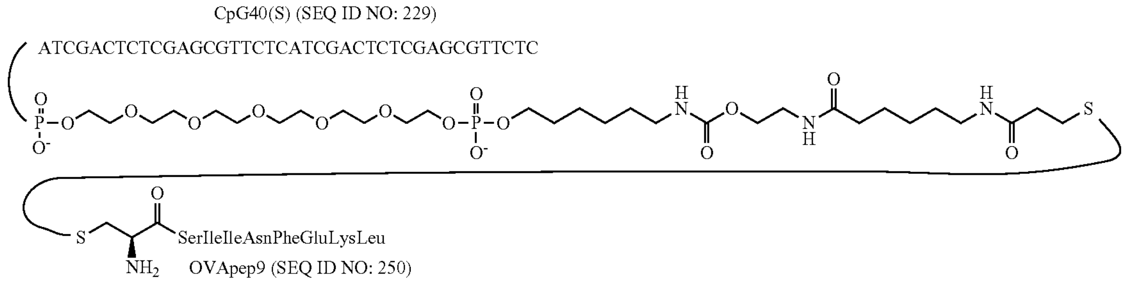

CpG40(S) (SEQ ID NO: 229)

OVApep9 (SEQ ID NO: 250)

-continued

[Chem. 30]

CpG40(S) (SEQ ID NO: 229)

ATCGACTCTCGAGCGTTCTCATCGACTCTCGAGCGTTCTC

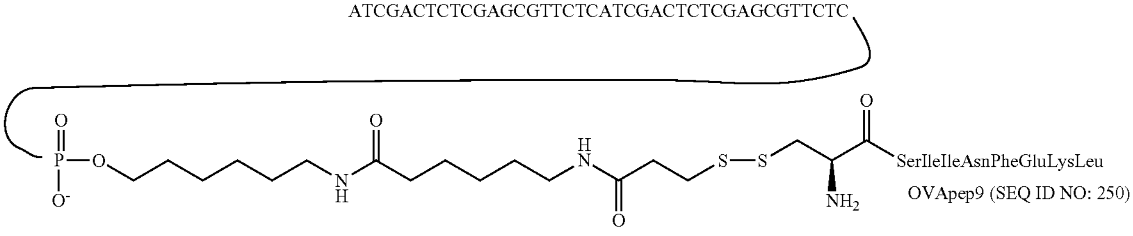

OVApep9 (SEQ ID NO: 250)

Example 7: Evaluation of the Amount of Antigen Presented on Peritoneal Macrophages Peritoneal macrophages collected from mice were placed in 48-well plates ($1.5\times10^5$ cells/well). Different CpG DNA (S)-peptide conjugates prepared using different amino acid lengths of antigenic peptides (OVApep9, OVApep18, OVA-pep27) and different nucleotide lengths of CpG DNA(S) (CpG40 (S), CpG30 (S) a, CpG30 (S) b, CpG20 (S) a) were added to the wells at a concentration of 2 μg/mL in terms of peptide, followed by culturing for 24 hours. After the culturing, an antibody specific for the OVApep8-MHC molecular complex (fluorescently labeled with phycoerythrin (PE); hereinafter abbreviated as "PE labelled H-2$K^b$/FIINFEKL" (FIINFEKL (SEQ ID NO:196)) was added, and antibody-bound peritoneal macrophages were quantified by flow cytometry to evaluate the amount of antigen presented.

Figure 6:
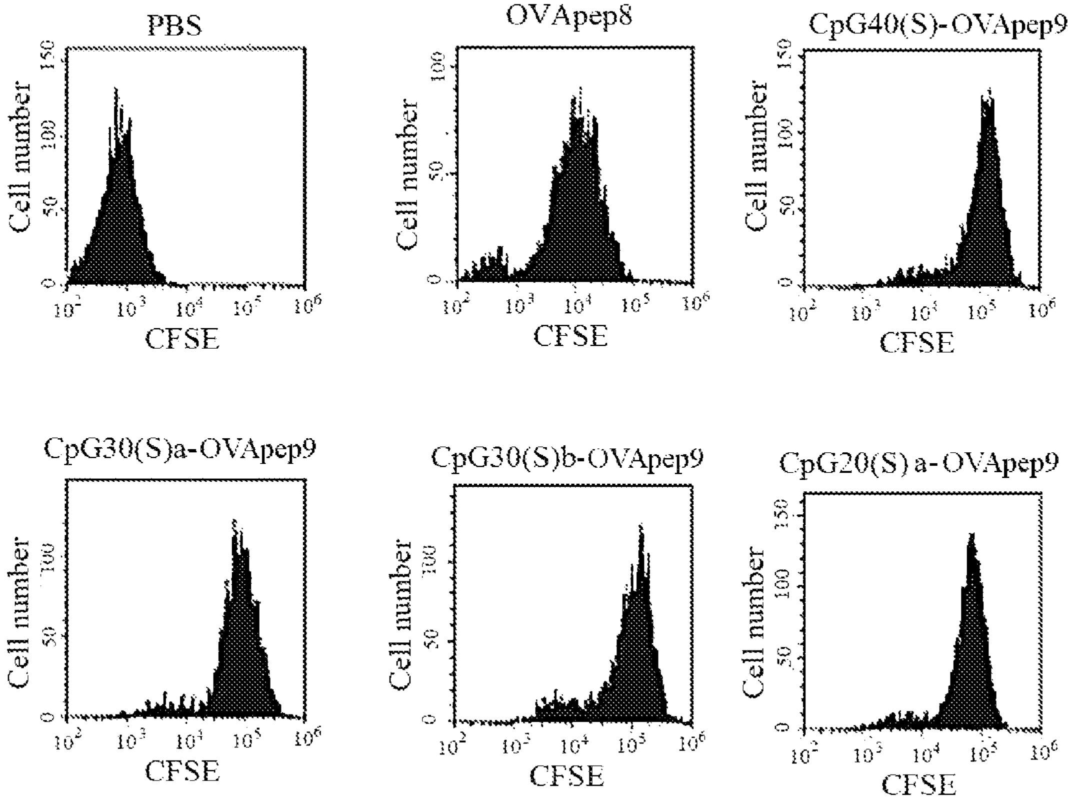
FIG. 6 depicts the results of the flow cytometric analysis performed in Example 7.
Figure 7:
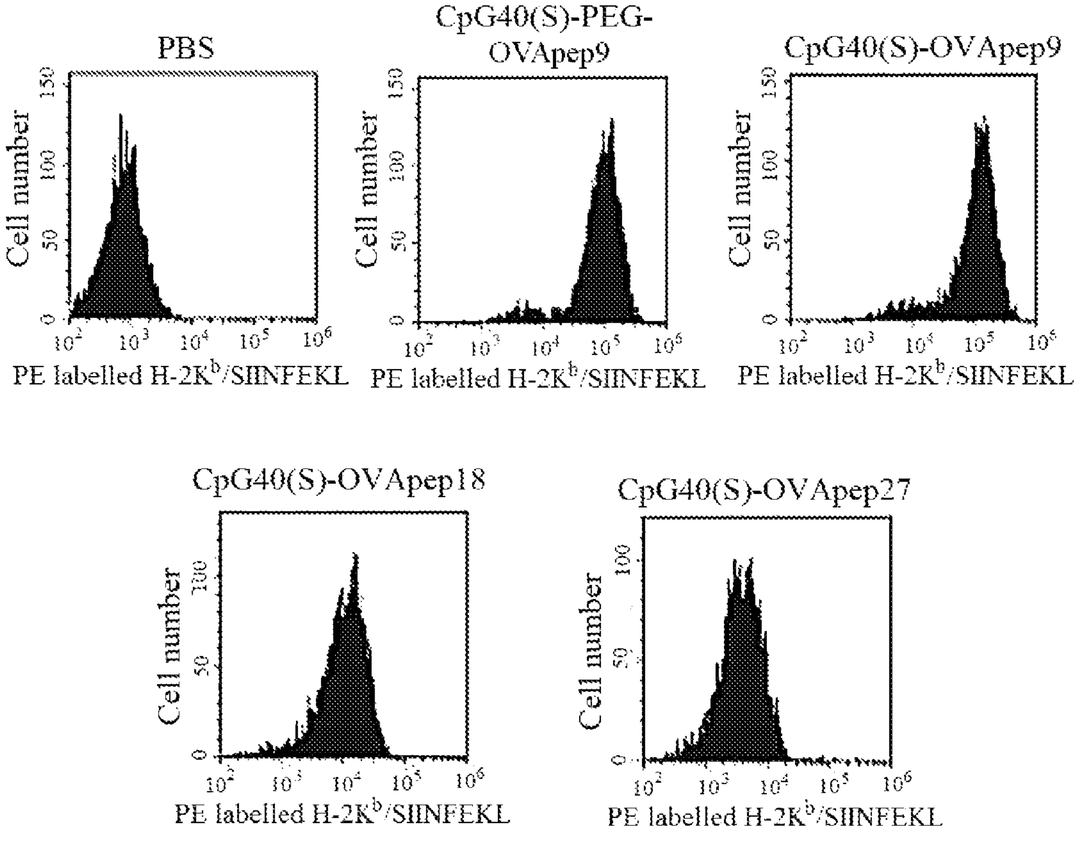
FIG. 7 depicts the results of the flow cytometric analysis performed in Example 7 comparing cell number as a function of H-2$K^b$/SIINFEKL (SEQ ID NO: 196).

The results of the flow cytometric analysis are shown in FIGS. 6 and 7. The results demonstrated that the nucleotide length of CpG DNA(S) has little effect on the amount of antigen presented, and that the amount of antigen presented tends to decrease as the antigenic peptide is extended to a length of 18 or 27 amino acids. Also, from the result obtained in FIG. 7 for "CpG40 (S)-PEG-OVApep9", which is a CpG40 (S)-OVApep9 conjugate having a polyoxyethylene group inserted into a spacer, it was observed that the polyoxyethylene group inserted into the spacer has little effect on the amount of antigen presented.

The invention claimed is:

1. An immunity-inducing agent comprising, as an active component, a conjugate comprising (i) a single-chain polynucleotide or a single-chain polynucleotide derivative comprising a CpG motif, and (ii) an antigenic peptide bound thereto via a spacer, wherein the spacer is covalently bound at one end thereof to the single-chain polynucleotide or the single-chain polynucleotide derivative comprising a CpG motif and covalently bound at the other end thereof to the antigenic peptide, wherein the single-chain polynucleotide or the single-chain polynucleotide derivative comprising a CpG motif is not complexed with β-1,3-glucan, wherein the antigenic peptide and the spacer are bound together via a disulfide bond produced by a reaction between a thiol group of a cysteine residue at the N-terminus of the antigenic peptide and a thiol group of the spacer, and wherein the spacer comprises a repeating unit represented by the formula:

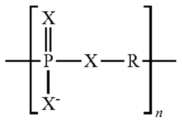

wherein

X represents an oxygen atom or a sulfur atom, wherein each X may be the same or different, R represents any of $(CH_2)_pO$, $(CH_2)_qNH$, and $(CH_2CH_2O)_m$, wherein m, p and q each independently represent a natural number of not more than 10, and n represents a natural number of not more than 10.

2. The immunity-inducing agent according to claim 1, wherein the antigenic peptide has an amino acid length of not less than 5 but not more than 30.

3. The immunity-inducing agent according to claim 1, wherein the antigenic peptide has an amino acid length of not less than 8 but not more than 11.

4. The immunity-inducing agent according to claim 1, wherein the single-chain polynucleotide or the single-chain polynucleotide derivative is a polydeoxyribonucleotide (DNA) or a DNA derivative comprising two or more CpG motifs.

5. The immunity-inducing agent according to claim 1, wherein the single-chain polynucleotide or the single-chain polynucleotide derivative comprising a CpG motif has a nucleotide length of not less than 15 but not more than 40.

6. The immunity-inducing agent according to claim 1, wherein the single-chain polynucleotide or the single-chain polynucleotide derivative comprising a CpG motif has a nucleotide length of not less than 20 but not more than 30.

7. The immunity-inducing agent according to claim 1, wherein the single-chain polynucleotide or the single-chain polynucleotide derivative comprising a CpG motif is a polynucleotide derivative in which phosphodiester bonds are at least partially substituted with phosphorothioate bonds.

8. The immunity-inducing agent according to claim 7, wherein, in the polynucleotide derivative in which phosphodiester bonds are at least partially substituted with phosphorothioate bonds, not less than 50% of the phosphodiester bonds are substituted with phosphorothioate bonds.

9. The immunity-inducing agent according to claim 7, wherein, in the polynucleotide derivative in which phosphodiester bonds are at least partially substituted with phosphorothioate bonds, not less than 90% of the phosphodiester bonds are substituted with phosphorothioate bonds.

10. The immunity-inducing agent according to claim 1, wherein the spacer comprises a repeating unit represented by the formula:

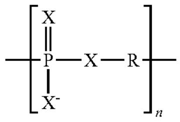

wherein

X represents an oxygen atom or a sulfur atom, wherein each X may be the same or different, R represents $(CH_2)_qNH$, wherein each q independently represents a natural number of not more than 10, and n represents a natural number of not more than 10.

11. The immunity-inducing agent according to claim 1, wherein the spacer has a structure represented by any of the formulas:

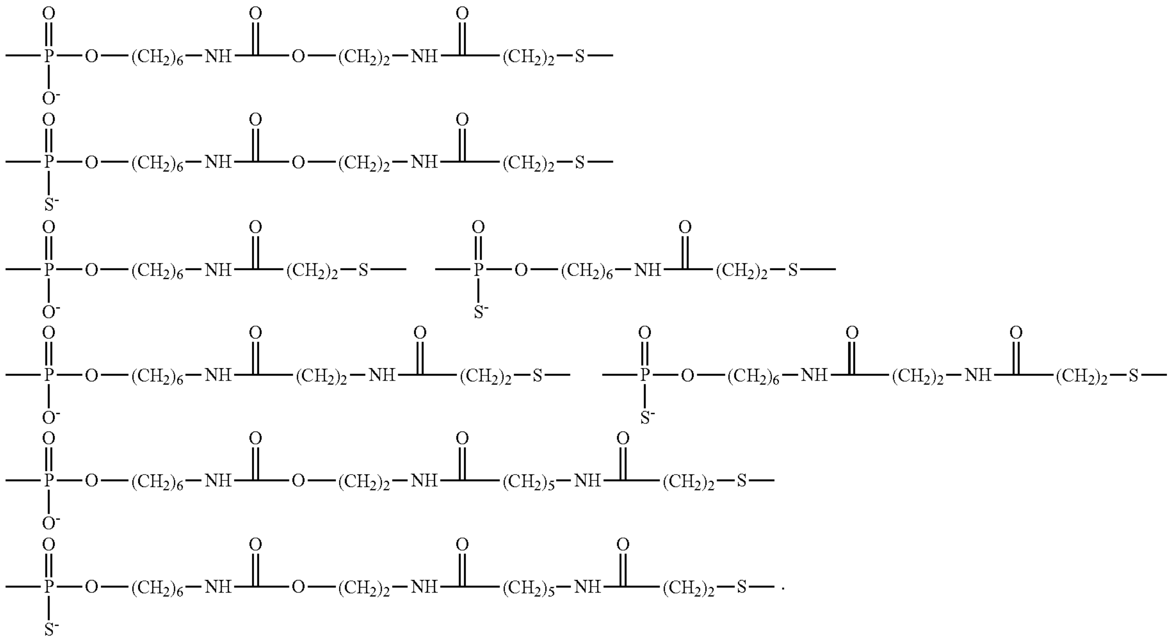

12. The immunity-inducing agent according to claim 1, further comprising a substance having immunostimulatory activity as an adjuvant.

13. An immunity-inducing agent according to claim 1, wherein the antigenic peptide has an amino acid length of not less than 5 but not more than 30, wherein the single-chain polynucleotide or the single-chain polynucleotide derivative comprising a CpG motif is a polydeoxyribonucleotide (DNA) or a DNA derivative comprising two or more CpG motifs, wherein the single-chain polynucleotide or the single-chain polynucleotide derivative comprising a CpG motif is a polynucleotide derivative in which phosphodiester bonds are at least partially substituted with phosphorothioate bonds, and wherein the antigenic peptide and the spacer are bound together via a disulfide bond produced by a reaction between a thiol group of a cysteine residue at the N-terminus of the antigenic peptide and a thiol group of the spacer.

14. An immunity-inducing agent according to claim 1, wherein the antigenic peptide has an amino acid length of not less than 8 but not more than 11, wherein the single-chain polynucleotide or the single-chain polynucleotide derivative comprising a CpG motif is a polydeoxyribonucleotide (DNA) or a DNA derivative comprising two or more CpG motifs, wherein the single-chain polynucleotide or the single-chain polynucleotide derivative comprising a CpG motif has a nucleotide length of not less than 20 but not more than 30, wherein, in the polynucleotide derivative in which phosphodiester bonds are at least partially substituted with phosphorothioate bonds, not less than 90% of the phosphodiester bonds are substituted with phosphorothioate bonds, and the antigenic peptide and the spacer are bound together via a disulfide bond produced by a reaction between a thiol group of a cysteine residue at the N-terminus of the antigenic peptide and a thiol group of the spacer.

15. An immunity-inducing agent according to claim 1, wherein the antigenic peptide has an amino acid length of not less than 8 but not more than 11, wherein the single-chain polynucleotide or the single-chain polynucleotide derivative comprising a CpG motif is a polydeoxyribonucleotide (DNA) or a DNA derivative comprising two or more CpG motifs, wherein the single-chain polynucleotide or the single-chain polynucleotide derivative comprising a CpG motif has a nucleotide length of not less than 20 but not more than 30, wherein, in the polynucleotide derivative in which phosphodiester bonds are at least partially substituted with phosphorothioate bonds, not less than 90% of the phosphodiester bonds are substituted with phosphorothioate bonds, wherein the antigenic peptide and the spacer are bound together via a disulfide bond produced by a reaction between a thiol group of a cysteine residue at the N-terminus of the antigenic peptide and a thiol group of the spacer, and wherein the spacer comprises a repeating unit represented by the formula:

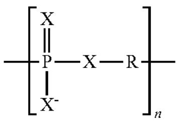

wherein

X represents an oxygen atom or a sulfur atom, wherein each X may be the same or different, R represents any of $(CH_2)_pO$, $(CH_2)_qNH$, and $(CH_2CH_2O)_m$, wherein m, p and q each independently represent a natural number of not more than 10, and n represents a natural number of not more than 10.

16. An immunity-inducing agent according to claim 1, wherein the antigenic peptide has an amino acid length of not less than 8 but not more than 11, wherein the single-chain polynucleotide or the single-chain polynucleotide derivative comprising a CpG motif is a polydeoxyribonucleotide (DNA) or a DNA derivative comprising two or more CpG motifs, wherein the single-chain polynucleotide or the single-chain polynucleotide derivative comprising a CpG motif has a nucleotide length of not less than 20 but not more than 30, wherein, in the polynucleotide derivative in which phosphodiester bonds are at least partially substituted with phosphorothioate bonds, not less than 90% of the phosphodiester bonds are substituted with phosphorothioate bonds, wherein the antigenic peptide and the spacer are bound together via a disulfide bond produced by a reaction between a thiol group of a cysteine residue at the N-terminus of the antigenic peptide and a thiol group of the spacer, and wherein the spacer has a structure represented by any of the formulas:

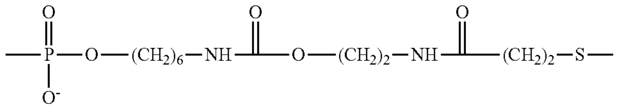

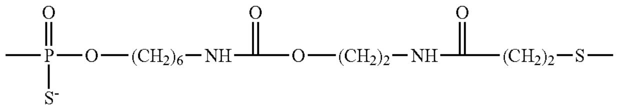

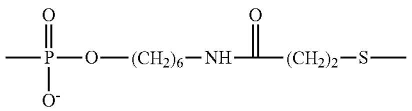

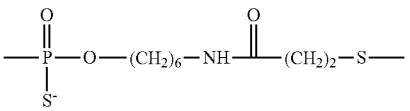

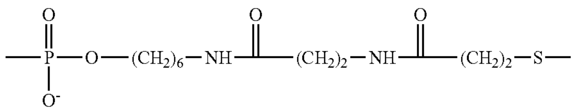

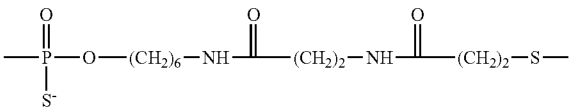

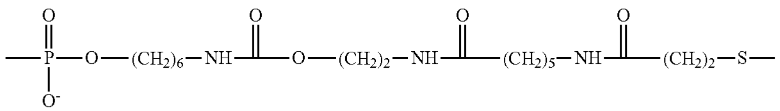

-continued

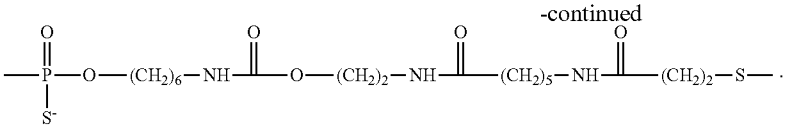

17. A pharmaceutical composition comprising a conjugate comprising (i) a single-chain polynucleotide or a single-chain polynucleotide derivative comprising a CpG motif, and (ii) an antigenic peptide bound thereto via a spacer, wherein the spacer is covalently bound at one end thereof to the single-chain polynucleotide or the single-chain polynucleotide derivative comprising a CpG motif and covalently bound at the other end thereof to the antigenic peptide, wherein the single-chain polynucleotide or the single-chain polynucleotide derivative comprising a CpG motif is not complexed with β-1,3-glucan, wherein the antigenic peptide and the spacer are bound together via a disulfide bond produced by a reaction between a thiol group of a cysteine residue at the N-terminus of the antigenic peptide and a thiol group of the spacer, and wherein the spacer comprises a repeating unit represented by the formula:

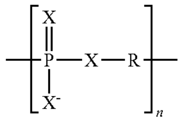

wherein

X represents an oxygen atom or a sulfur atom, wherein each X may be the same or different, R represents any of $(CH_2)_pO$, $(CH_2)_qNH$, and $(CH_2CH_2O)_m$, wherein m, p and q each independently represent a natural number of not more than 10, and n represents a natural number of not more than 10.

18. A pharmaceutical composition comprising the immunity-inducing agent according to claim 13.

19. A pharmaceutical composition comprising the immunity-inducing agent according to claim 14.

20. A pharmaceutical composition comprising the immunity-inducing agent according to claim 15.

21. A pharmaceutical composition comprising the immunity-inducing agent according to claim 16.

22. A method for treating a tumor, comprising administering an effective amount of the immunity-inducing agent according to claim 1 to a subject in need thereof.

23. A method for treating a tumor, comprising administering an effective amount of the pharmaceutical composition of according to claim 17 to a subject in need thereof.

24. A method for treating a tumor, comprising administering an effective amount of the pharmaceutical composition of according to claim 18 to a subject in need thereof.

25. A method for treating a tumor, comprising administering an effective amount of the pharmaceutical composition of according to claim 19 to a subject in need thereof.

26. A method for treating a tumor, comprising administering an effective amount of the pharmaceutical composition of according to claim 20 to a subject in need thereof.

27. A method for treating a tumor, comprising administering an effective amount of the pharmaceutical composition of according to claim 21 to a subject in need thereof.

* * * * *

SEQUENCE LISTING

<160> NUMBER OF SEQ ID NOS: 252

<210> SEQ ID NO 1
<211> LENGTH: 10
<212> TYPE: PRT
<213> ORGANISM: HPV

<400> SEQUENCE: 1

Tyr Met Leu Asp Leu Gln Pro Glu Thr Thr
1               5                   10

<210> SEQ ID NO 2
<211> LENGTH: 9
<212> TYPE: PRT
<213> ORGANISM: HPV

<400> SEQUENCE: 2

Arg Ala His Tyr Asn Ile Val Thr Phe
1               5

<210> SEQ ID NO 3
<211> LENGTH: 9
<212> TYPE: PRT
<213> ORGANISM: HPV

<400> SEQUENCE: 3

Asn Thr Leu Glu Gln Thr Val Lys Lys
1               5

<210> SEQ ID NO 4
<211> LENGTH: 10
<212> TYPE: PRT
<213> ORGANISM: HPV

<400> SEQUENCE: 4

```
Glu Val Tyr Asp Phe Ala Phe Arg Asp Leu
1               5                   10


<210> SEQ ID NO 5
<211> LENGTH: 9
<212> TYPE: PRT
<213> ORGANISM: HBV

<400> SEQUENCE: 5

Phe Leu Leu Thr Arg Ile Leu Thr Ile
1               5


<210> SEQ ID NO 6
<211> LENGTH: 10
<212> TYPE: PRT
<213> ORGANISM: HBV

<400> SEQUENCE: 6

Gly Leu Ser Pro Thr Val Trp Leu Ser Val
1               5                   10


<210> SEQ ID NO 7
<211> LENGTH: 9
<212> TYPE: PRT
<213> ORGANISM: HBV

<400> SEQUENCE: 7

Trp Leu Ser Leu Leu Val Pro Phe Val
1               5


<210> SEQ ID NO 8
<211> LENGTH: 10
<212> TYPE: PRT
<213> ORGANISM: HBV

<400> SEQUENCE: 8

Phe Leu Pro Ser Asp Phe Phe Pro Ser Val
1               5                   10


<210> SEQ ID NO 9
<211> LENGTH: 9
<212> TYPE: PRT
<213> ORGANISM: HBV

<400> SEQUENCE: 9

Tyr Val Asn Val Asn Met Gly Leu Lys
1               5


<210> SEQ ID NO 10
<211> LENGTH: 9
<212> TYPE: PRT
<213> ORGANISM: HBV

<400> SEQUENCE: 10

Lys Leu His Leu Tyr Ser His Pro Ile
1               5


<210> SEQ ID NO 11
<211> LENGTH: 9
<212> TYPE: PRT
<213> ORGANISM: HBV

<400> SEQUENCE: 11

Gly Leu Ser Arg Tyr Val Ala Arg Leu
```

1 5

<210> SEQ ID NO 12
<211> LENGTH: 10
<212> TYPE: PRT
<213> ORGANISM: HBV

<400> SEQUENCE: 12

Lys Leu Val Ala Leu Gly Ile Asn Ala Val
1 5 10

<210> SEQ ID NO 13
<211> LENGTH: 10
<212> TYPE: PRT
<213> ORGANISM: HBV

<400> SEQUENCE: 13

Gly Val Asp Pro Asn Ile Arg Thr Gly Val
1 5 10

<210> SEQ ID NO 14
<211> LENGTH: 9
<212> TYPE: PRT
<213> ORGANISM: HBV

<400> SEQUENCE: 14

Ala Leu Tyr Asp Val Val Thr Lys Leu
1 5

<210> SEQ ID NO 15
<211> LENGTH: 8
<212> TYPE: PRT
<213> ORGANISM: HBV

<400> SEQUENCE: 15

Val Trp Leu Ser Val Ile Trp Met
1 5

<210> SEQ ID NO 16
<211> LENGTH: 9
<212> TYPE: PRT
<213> ORGANISM: HSV

<400> SEQUENCE: 16

Ser Leu Pro Ile Thr Val Tyr Tyr Ala
1 5

<210> SEQ ID NO 17
<211> LENGTH: 9
<212> TYPE: PRT
<213> ORGANISM: HSV

<400> SEQUENCE: 17

Val Leu Leu Asn Ala Pro Ser Glu Ala
1 5

<210> SEQ ID NO 18
<211> LENGTH: 9
<212> TYPE: PRT
<213> ORGANISM: HSV

<400> SEQUENCE: 18

Ala Leu Leu Glu Asp Pro Val Gly Thr
1 5

<210> SEQ ID NO 19
<211> LENGTH: 9
<212> TYPE: PRT
<213> ORGANISM: HSV

<400> SEQUENCE: 19

Arg Met Leu Gly Asp Val Met Ala Val
1 5

<210> SEQ ID NO 20
<211> LENGTH: 9
<212> TYPE: PRT
<213> ORGANISM: HSV

<400> SEQUENCE: 20

Asn Leu Leu Thr Thr Pro Lys Phe Thr
1 5

<210> SEQ ID NO 21
<211> LENGTH: 9
<212> TYPE: PRT
<213> ORGANISM: CMV

<400> SEQUENCE: 21

Asn Leu Val Pro Met Val Ala Thr Val
1 5

<210> SEQ ID NO 22
<211> LENGTH: 9
<212> TYPE: PRT
<213> ORGANISM: CMV

<400> SEQUENCE: 22

Val Tyr Ala Leu Pro Leu Lys Met Leu
1 5

<210> SEQ ID NO 23
<211> LENGTH: 9
<212> TYPE: PRT
<213> ORGANISM: CMV

<400> SEQUENCE: 23

Gln Tyr Asp Pro Val Ala Ala Leu Phe
1 5

<210> SEQ ID NO 24
<211> LENGTH: 9
<212> TYPE: PRT
<213> ORGANISM: CMV

<400> SEQUENCE: 24

Val Leu Glu Glu Thr Ser Val Met Leu
1 5

<210> SEQ ID NO 25
<211> LENGTH: 9
<212> TYPE: PRT
<213> ORGANISM: CMV

<400> SEQUENCE: 25

Ala Tyr Ala Gln Lys Ile Phe Lys Ile
1 5

<210> SEQ ID NO 26

<211> LENGTH: 9
<212> TYPE: PRT
<213> ORGANISM: Influenza virus

<400> SEQUENCE: 26

Cys Thr Glu Leu Lys Leu Ser Asp Tyr
1 5

<210> SEQ ID NO 27
<211> LENGTH: 9
<212> TYPE: PRT
<213> ORGANISM: Influenza virus

<400> SEQUENCE: 27

Gly Ile Leu Gly Phe Val Phe Thr Leu
1 5

<210> SEQ ID NO 28
<211> LENGTH: 10
<212> TYPE: PRT
<213> ORGANISM: Influenza virus

<400> SEQUENCE: 28

Ile Leu Gly Phe Val Phe Thr Leu Thr Val
1 5 10

<210> SEQ ID NO 29
<211> LENGTH: 9
<212> TYPE: PRT
<213> ORGANISM: Influenza virus

<400> SEQUENCE: 29

Tyr Ile Gly Glu Val Leu Val Ser Val
1 5

<210> SEQ ID NO 30
<211> LENGTH: 10
<212> TYPE: PRT
<213> ORGANISM: Influenza virus

<400> SEQUENCE: 30

Lys Leu Gly Glu Phe Tyr Asn Gln Met Met
1 5 10

<210> SEQ ID NO 31
<211> LENGTH: 9
<212> TYPE: PRT
<213> ORGANISM: RSV

<400> SEQUENCE: 31

Tyr Leu Glu Lys Glu Ser Ile Tyr Tyr
1 5

<210> SEQ ID NO 32
<211> LENGTH: 9
<212> TYPE: PRT
<213> ORGANISM: RSV

<400> SEQUENCE: 32

Ser Tyr Ile Gly Ser Ile Asn Asn Ile
1 5

<210> SEQ ID NO 33
<211> LENGTH: 9
<212> TYPE: PRT

<213> ORGANISM: RSV

<400> SEQUENCE: 33

Lys Met Leu Lys Glu Met Gly Glu Val
1 5

<210> SEQ ID NO 34
<211> LENGTH: 9
<212> TYPE: PRT
<213> ORGANISM: RSV

<400> SEQUENCE: 34

Ala Ile Thr Thr Ile Leu Ala Ala Val
1 5

<210> SEQ ID NO 35
<211> LENGTH: 9
<212> TYPE: PRT
<213> ORGANISM: RSV

<400> SEQUENCE: 35

Ala Leu Leu Ser Thr Asn Lys Ala Val
1 5

<210> SEQ ID NO 36
<211> LENGTH: 9
<212> TYPE: PRT
<213> ORGANISM: RSV

<400> SEQUENCE: 36

Glu Leu Asp Lys Tyr Lys Asn Ala Val
1 5

<210> SEQ ID NO 37
<211> LENGTH: 9
<212> TYPE: PRT
<213> ORGANISM: RSV

<400> SEQUENCE: 37

Phe Leu Leu Gly Val Gly Ser Ala Ile
1 5

<210> SEQ ID NO 38
<211> LENGTH: 9
<212> TYPE: PRT
<213> ORGANISM: RSV

<400> SEQUENCE: 38

Phe Met Asn Tyr Thr Leu Asn Asn Thr
1 5

<210> SEQ ID NO 39
<211> LENGTH: 9
<212> TYPE: PRT
<213> ORGANISM: RSV

<400> SEQUENCE: 39

His Leu Glu Gly Glu Val Asn Lys Ile
1 5

<210> SEQ ID NO 40
<211> LENGTH: 9
<212> TYPE: PRT
<213> ORGANISM: RSV

<400> SEQUENCE: 40

Lys Ile Met Thr Ser Lys Thr Asp Val
1               5

<210> SEQ ID NO 41
<211> LENGTH: 9
<212> TYPE: PRT
<213> ORGANISM: RSV

<400> SEQUENCE: 41

Lys Ile Asn Gln Ser Leu Ala Phe Ile
1               5

<210> SEQ ID NO 42
<211> LENGTH: 9
<212> TYPE: PRT
<213> ORGANISM: RSV

<400> SEQUENCE: 42

Ser Val Tyr Asp Phe Phe Val Trp Leu
1               5

<210> SEQ ID NO 43
<211> LENGTH: 9
<212> TYPE: PRT
<213> ORGANISM: HIV

<400> SEQUENCE: 43

Arg Tyr Leu Lys Asp Gln Gln Leu Leu
1               5

<210> SEQ ID NO 44
<211> LENGTH: 10
<212> TYPE: PRT
<213> ORGANISM: HIV

<400> SEQUENCE: 44

Ser Leu Leu Asn Ala Thr Ala Ile Ala Val
1               5                   10

<210> SEQ ID NO 45
<211> LENGTH: 9
<212> TYPE: PRT
<213> ORGANISM: HIV

<400> SEQUENCE: 45

Ser Leu Tyr Asn Thr Val Ala Thr Leu
1               5

<210> SEQ ID NO 46
<211> LENGTH: 9
<212> TYPE: PRT
<213> ORGANISM: HIV

<400> SEQUENCE: 46

Arg Thr Leu Asn Ala Trp Val Lys Val
1               5

<210> SEQ ID NO 47
<211> LENGTH: 8
<212> TYPE: PRT
<213> ORGANISM: HIV

<400> SEQUENCE: 47

Phe Leu Gly Lys Ile Trp Pro Ser
1 5

<210> SEQ ID NO 48
<211> LENGTH: 9
<212> TYPE: PRT
<213> ORGANISM: HIV

<400> SEQUENCE: 48

Thr Leu Asn Ala Trp Val Lys Val Val
1 5

<210> SEQ ID NO 49
<211> LENGTH: 9
<212> TYPE: PRT
<213> ORGANISM: HIV

<400> SEQUENCE: 49

Ser Leu Phe Asn Thr Val Ala Thr Leu
1 5

<210> SEQ ID NO 50
<211> LENGTH: 10
<212> TYPE: PRT
<213> ORGANISM: HIV

<400> SEQUENCE: 50

Ser Leu Tyr Asn Thr Val Ala Thr Leu Tyr
1 5 10

<210> SEQ ID NO 51
<211> LENGTH: 9
<212> TYPE: PRT
<213> ORGANISM: Polynomavirus

<400> SEQUENCE: 51

Leu Leu Met Trp Glu Ala Val Thr Val
1 5

<210> SEQ ID NO 52
<211> LENGTH: 9
<212> TYPE: PRT
<213> ORGANISM: Polynomavirus

<400> SEQUENCE: 52

Leu Leu Leu Ile Trp Phe Arg Pro Val
1 5

<210> SEQ ID NO 53
<211> LENGTH: 9
<212> TYPE: PRT
<213> ORGANISM: HTLV-1

<400> SEQUENCE: 53

Leu Leu Phe Gly Tyr Pro Val Tyr Val
1 5

<210> SEQ ID NO 54
<211> LENGTH: 9
<212> TYPE: PRT
<213> ORGANISM: HTLV-1

<400> SEQUENCE: 54

Ser Phe His Ser Leu His Leu Leu Phe
1 5

<210> SEQ ID NO 55
<211> LENGTH: 10
<212> TYPE: PRT
<213> ORGANISM: EBV

<400> SEQUENCE: 55

Asp Tyr Cys Asn Val Leu Asn Lys Glu Phe
1 5 10

<210> SEQ ID NO 56
<211> LENGTH: 9
<212> TYPE: PRT
<213> ORGANISM: EBV

<400> SEQUENCE: 56

Thr Leu Asp Tyr Lys Pro Leu Ser Val
1 5

<210> SEQ ID NO 57
<211> LENGTH: 9
<212> TYPE: PRT
<213> ORGANISM: EBV

<400> SEQUENCE: 57

Tyr Val Leu Asp His Leu Ile Val Val
1 5

<210> SEQ ID NO 58
<211> LENGTH: 9
<212> TYPE: PRT
<213> ORGANISM: EBV

<400> SEQUENCE: 58

Tyr Leu Leu Glu Met Leu Trp Arg Leu
1 5

<210> SEQ ID NO 59
<211> LENGTH: 9
<212> TYPE: PRT
<213> ORGANISM: EBV

<400> SEQUENCE: 59

Tyr Leu Gln Gln Asn Trp Trp Thr Leu
1 5

<210> SEQ ID NO 60
<211> LENGTH: 9
<212> TYPE: PRT
<213> ORGANISM: Homo sapiens

<400> SEQUENCE: 60

Gln Gln Ala His Cys Leu Trp Cys Val
1 5

<210> SEQ ID NO 61
<211> LENGTH: 9
<212> TYPE: PRT
<213> ORGANISM: Homo sapiens

<400> SEQUENCE: 61

Ala Leu Asp Val Tyr Asn Gly Leu Leu
1 5

<210> SEQ ID NO 62
<211> LENGTH: 9
<212> TYPE: PRT
<213> ORGANISM: Homo sapiens

<400> SEQUENCE: 62

Ala Leu Asn Val Tyr Asn Gly Leu Leu
1 5

<210> SEQ ID NO 63
<211> LENGTH: 9
<212> TYPE: PRT
<213> ORGANISM: Homo sapiens

<400> SEQUENCE: 63

Asn Leu Phe Glu Thr Pro Val Glu Ala
1 5

<210> SEQ ID NO 64
<211> LENGTH: 9
<212> TYPE: PRT
<213> ORGANISM: Homo sapiens

<400> SEQUENCE: 64

Gly Leu Gln His Trp Val Pro Glu Leu
1 5

<210> SEQ ID NO 65
<211> LENGTH: 9
<212> TYPE: PRT
<213> ORGANISM: Homo sapiens

<400> SEQUENCE: 65

Lys Leu Asp Val Gly Asn Ala Glu Val
1 5

<210> SEQ ID NO 66
<211> LENGTH: 10
<212> TYPE: PRT
<213> ORGANISM: Homo sapiens

<400> SEQUENCE: 66

Pro Leu Phe Asp Phe Ser Trp Leu Ser Leu
1 5 10

<210> SEQ ID NO 67
<211> LENGTH: 10
<212> TYPE: PRT
<213> ORGANISM: Homo sapiens

<400> SEQUENCE: 67

Tyr Leu Asn Arg His Leu His Thr Trp Ile
1 5 10

<210> SEQ ID NO 68
<211> LENGTH: 10
<212> TYPE: PRT
<213> ORGANISM: Homo sapiens

<400> SEQUENCE: 68

Trp Leu Ser Leu Lys Thr Leu Leu Ser Leu
1 5 10

<210> SEQ ID NO 69
<211> LENGTH: 9

<212> TYPE: PRT
<213> ORGANISM: Homo sapiens

<400> SEQUENCE: 69

Ala Leu Ser Pro Val Pro Pro Val Val
1               5

<210> SEQ ID NO 70
<211> LENGTH: 10
<212> TYPE: PRT
<213> ORGANISM: Homo sapiens

<400> SEQUENCE: 70

Tyr Leu Asn Asp His Leu Glu Pro Trp Ile
1               5                   10

<210> SEQ ID NO 71
<211> LENGTH: 9
<212> TYPE: PRT
<213> ORGANISM: Homo sapiens

<400> SEQUENCE: 71

Cys Leu Pro Ser Pro Ser Thr Pro Val
1               5

<210> SEQ ID NO 72
<211> LENGTH: 9
<212> TYPE: PRT
<213> ORGANISM: Homo sapiens

<400> SEQUENCE: 72

Thr Leu Gln Asp Ile Val Tyr Lys Leu
1               5

<210> SEQ ID NO 73
<211> LENGTH: 11
<212> TYPE: PRT
<213> ORGANISM: Homo sapiens

<400> SEQUENCE: 73

Met Leu Met Ala Gln Glu Ala Leu Ala Phe Leu
1               5                   10

<210> SEQ ID NO 74
<211> LENGTH: 9
<212> TYPE: PRT
<213> ORGANISM: Homo sapiens

<400> SEQUENCE: 74

Ala Leu Tyr Leu Met Glu Leu Thr Met
1               5

<210> SEQ ID NO 75
<211> LENGTH: 9
<212> TYPE: PRT
<213> ORGANISM: Homo sapiens

<400> SEQUENCE: 75

Tyr Leu Ile Ser Gly Asp Ser Pro Val
1               5

<210> SEQ ID NO 76
<211> LENGTH: 9
<212> TYPE: PRT
<213> ORGANISM: Homo sapiens

<400> SEQUENCE: 76

Tyr Leu Ser Gly Ala Asn Leu Asn Leu
1               5

<210> SEQ ID NO 77
<211> LENGTH: 9
<212> TYPE: PRT
<213> ORGANISM: Homo sapiens

<400> SEQUENCE: 77

Ile Leu Gly Val Leu Thr Ser Leu Val
1               5

<210> SEQ ID NO 78
<211> LENGTH: 10
<212> TYPE: PRT
<213> ORGANISM: Homo sapiens

<400> SEQUENCE: 78

Leu Leu Val Pro Thr Cys Val Phe Leu Val
1               5                   10

<210> SEQ ID NO 79
<211> LENGTH: 9
<212> TYPE: PRT
<213> ORGANISM: Homo sapiens

<400> SEQUENCE: 79

Thr Leu Ala Asp Phe Asp Pro Arg Val
1               5

<210> SEQ ID NO 80
<211> LENGTH: 9
<212> TYPE: PRT
<213> ORGANISM: Homo sapiens

<400> SEQUENCE: 80

Tyr Met Cys Ser Phe Leu Phe Asn Leu
1               5

<210> SEQ ID NO 81
<211> LENGTH: 9
<212> TYPE: PRT
<213> ORGANISM: Homo sapiens

<400> SEQUENCE: 81

Ser Gln Ala Asp Ala Leu Lys Tyr Val
1               5

<210> SEQ ID NO 82
<211> LENGTH: 9
<212> TYPE: PRT
<213> ORGANISM: Homo sapiens

<400> SEQUENCE: 82

Ala Leu Val Cys Tyr Gly Pro Gly Ile
1               5

<210> SEQ ID NO 83
<211> LENGTH: 9
<212> TYPE: PRT
<213> ORGANISM: Homo sapiens

<400> SEQUENCE: 83

Gly Leu Phe Lys Cys Gly Ile Ala Val
1 5

<210> SEQ ID NO 84
<211> LENGTH: 8
<212> TYPE: PRT
<213> ORGANISM: Homo sapiens

<400> SEQUENCE: 84

Thr Leu Phe Trp Leu Leu Thr Leu
1 5

<210> SEQ ID NO 85
<211> LENGTH: 9
<212> TYPE: PRT
<213> ORGANISM: Homo sapiens

<400> SEQUENCE: 85

Glu Ile Trp Thr His Ser Tyr Lys Val
1 5

<210> SEQ ID NO 86
<211> LENGTH: 9
<212> TYPE: PRT
<213> ORGANISM: Homo sapiens

<400> SEQUENCE: 86

Phe Val Gly Glu Phe Phe Thr Asp Val
1 5

<210> SEQ ID NO 87
<211> LENGTH: 9
<212> TYPE: PRT
<213> ORGANISM: Homo sapiens

<400> SEQUENCE: 87

Lys Thr Trp Gly Gln Tyr Trp Gln Val
1 5

<210> SEQ ID NO 88
<211> LENGTH: 9
<212> TYPE: PRT
<213> ORGANISM: Homo sapiens

<400> SEQUENCE: 88

Ile Thr Asp Gln Val Pro Phe Ser Val
1 5

<210> SEQ ID NO 89
<211> LENGTH: 9
<212> TYPE: PRT
<213> ORGANISM: Homo sapiens

<400> SEQUENCE: 89

Ile Met Asp Gln Val Pro Phe Ser Val
1 5

<210> SEQ ID NO 90
<211> LENGTH: 9
<212> TYPE: PRT
<213> ORGANISM: Homo sapiens

<400> SEQUENCE: 90

Tyr Leu Glu Pro Gly Pro Val Thr Val 1 5

<210> SEQ ID NO 91
<211> LENGTH: 9
<212> TYPE: PRT
<213> ORGANISM: Homo sapiens

<400> SEQUENCE: 91

Gln Leu Phe Glu Glu Leu Gln Glu Leu
1 5

<210> SEQ ID NO 92
<211> LENGTH: 9
<212> TYPE: PRT
<213> ORGANISM: Homo sapiens

<400> SEQUENCE: 92

Leu Leu Leu Gly Pro Leu Gly Pro Leu
1 5

<210> SEQ ID NO 93
<211> LENGTH: 9
<212> TYPE: PRT
<213> ORGANISM: Homo sapiens

<400> SEQUENCE: 93

Ile Leu His Asp Gly Ala Tyr Ser Leu
1 5

<210> SEQ ID NO 94
<211> LENGTH: 10
<212> TYPE: PRT
<213> ORGANISM: Homo sapiens

<400> SEQUENCE: 94

Leu Ile Ala His Asn Gln Val Arg Gln Val
1 5 10

<210> SEQ ID NO 95
<211> LENGTH: 9
<212> TYPE: PRT
<213> ORGANISM: Homo sapiens

<400> SEQUENCE: 95

Lys Ile Phe Gly Ser Leu Ala Phe Leu
1 5

<210> SEQ ID NO 96
<211> LENGTH: 9
<212> TYPE: PRT
<213> ORGANISM: Homo sapiens

<400> SEQUENCE: 96

Ile Leu Ser Leu Glu Leu Met Lys Leu
1 5

<210> SEQ ID NO 97
<211> LENGTH: 9
<212> TYPE: PRT
<213> ORGANISM: Homo sapiens

<400> SEQUENCE: 97

Ala Leu Pro Phe Gly Phe Ile Leu Val
1 5

<210> SEQ ID NO 98
<211> LENGTH: 9
<212> TYPE: PRT
<213> ORGANISM: Homo sapiens

<400> SEQUENCE: 98

Ala Leu Leu Glu Ile Ala Ser Cys Leu
1               5

<210> SEQ ID NO 99
<211> LENGTH: 9
<212> TYPE: PRT
<213> ORGANISM: Homo sapiens

<400> SEQUENCE: 99

Ala Leu Met Glu Gln Gln His Tyr Val
1               5

<210> SEQ ID NO 100
<211> LENGTH: 10
<212> TYPE: PRT
<213> ORGANISM: Homo sapiens

<400> SEQUENCE: 100

Val Ile Ser Asn Asp Val Cys Ala Gln Val
1               5                   10

<210> SEQ ID NO 101
<211> LENGTH: 10
<212> TYPE: PRT
<213> ORGANISM: Homo sapiens

<400> SEQUENCE: 101

Phe Ile Tyr Asp Phe Cys Ile Phe Gly Val
1               5                   10

<210> SEQ ID NO 102
<211> LENGTH: 10
<212> TYPE: PRT
<213> ORGANISM: Homo sapiens

<400> SEQUENCE: 102

Gln Leu Cys Pro Ile Cys Arg Ala Pro Val
1               5                   10

<210> SEQ ID NO 103
<211> LENGTH: 9
<212> TYPE: PRT
<213> ORGANISM: Homo sapiens

<400> SEQUENCE: 103

Tyr Leu Gln Gln Asn Trp Trp Thr Leu
1               5

<210> SEQ ID NO 104
<211> LENGTH: 10
<212> TYPE: PRT
<213> ORGANISM: Homo sapiens

<400> SEQUENCE: 104

Leu Leu Leu Ala Ser Ile Ala Ala Gly Leu
1               5                   10

<210> SEQ ID NO 105

<211> LENGTH: 9
<212> TYPE: PRT
<213> ORGANISM: Homo sapiens

<400> SEQUENCE: 105

Gly Leu Tyr Asp Gly Met Glu His Leu
1               5

<210> SEQ ID NO 106
<211> LENGTH: 9
<212> TYPE: PRT
<213> ORGANISM: Homo sapiens

<400> SEQUENCE: 106

Lys Val Ala Glu Leu Val His Phe Leu
1               5

<210> SEQ ID NO 107
<211> LENGTH: 9
<212> TYPE: PRT
<213> ORGANISM: Homo sapiens

<400> SEQUENCE: 107

Phe Leu Ala Met Leu Lys Asn Thr Val
1               5

<210> SEQ ID NO 108
<211> LENGTH: 9
<212> TYPE: PRT
<213> ORGANISM: Homo sapiens

<400> SEQUENCE: 108

Phe Leu Trp Gly Pro Arg Ala Leu Val
1               5

<210> SEQ ID NO 109
<211> LENGTH: 10
<212> TYPE: PRT
<213> ORGANISM: Homo sapiens

<400> SEQUENCE: 109

Gly Val Tyr Asp Gly Arg Glu His Thr Val
1               5                   10

<210> SEQ ID NO 110
<211> LENGTH: 9
<212> TYPE: PRT
<213> ORGANISM: Homo sapiens

<400> SEQUENCE: 110

Lys Val Leu Glu Tyr Val Ile Lys Val
1               5

<210> SEQ ID NO 111
<211> LENGTH: 10
<212> TYPE: PRT
<213> ORGANISM: Homo sapiens

<400> SEQUENCE: 111

Tyr Leu Gln Leu Val Phe Gly Ile Glu Val
1               5                   10

<210> SEQ ID NO 112
<211> LENGTH: 10
<212> TYPE: PRT

<213> ORGANISM: Homo sapiens

<400> SEQUENCE: 112

Glu Leu Ala Gly Ile Gly Ile Leu Thr Val
1 5 10

<210> SEQ ID NO 113
<211> LENGTH: 9
<212> TYPE: PRT
<213> ORGANISM: Homo sapiens

<400> SEQUENCE: 113

Ser Leu Leu Phe Leu Leu Phe Ser Leu
1 5

<210> SEQ ID NO 114
<211> LENGTH: 9
<212> TYPE: PRT
<213> ORGANISM: Homo sapiens

<400> SEQUENCE: 114

Val Leu Pro Leu Thr Val Ala Glu Val
1 5

<210> SEQ ID NO 115
<211> LENGTH: 9
<212> TYPE: PRT
<213> ORGANISM: Homo sapiens

<400> SEQUENCE: 115

Ala Gln Cys Gln Glu Thr Ile Arg Val
1 5

<210> SEQ ID NO 116
<211> LENGTH: 9
<212> TYPE: PRT
<213> ORGANISM: Homo sapiens

<400> SEQUENCE: 116

Ser Leu Phe Leu Gly Ile Leu Ser Val
1 5

<210> SEQ ID NO 117
<211> LENGTH: 9
<212> TYPE: PRT
<213> ORGANISM: Homo sapiens

<400> SEQUENCE: 117

Gly Met Leu Gly Met Val Ser Gly Leu
1 5

<210> SEQ ID NO 118
<211> LENGTH: 9
<212> TYPE: PRT
<213> ORGANISM: Homo sapiens

<400> SEQUENCE: 118

Ser Leu Leu Met Trp Ile Thr Gln Cys
1 5

<210> SEQ ID NO 119
<211> LENGTH: 9
<212> TYPE: PRT
<213> ORGANISM: Homo sapiens

<400> SEQUENCE: 119

Ser Leu Leu Met Trp Ile Thr Gln Val
1 5

<210> SEQ ID NO 120
<211> LENGTH: 10
<212> TYPE: PRT
<213> ORGANISM: Homo sapiens

<400> SEQUENCE: 120

Tyr Leu Tyr Gln Trp Leu Gly Ala Pro Val
1 5 10

<210> SEQ ID NO 121
<211> LENGTH: 9
<212> TYPE: PRT
<213> ORGANISM: Homo sapiens

<400> SEQUENCE: 121

Tyr Leu Gly Ser Tyr Gly Phe Arg Leu
1 5

<210> SEQ ID NO 122
<211> LENGTH: 9
<212> TYPE: PRT
<213> ORGANISM: Homo sapiens

<400> SEQUENCE: 122

Lys Leu Cys Pro Val Gln Leu Trp Val
1 5

<210> SEQ ID NO 123
<211> LENGTH: 9
<212> TYPE: PRT
<213> ORGANISM: Homo sapiens

<400> SEQUENCE: 123

Ser Leu Pro Pro Pro Gly Thr Arg Val
1 5

<210> SEQ ID NO 124
<211> LENGTH: 11
<212> TYPE: PRT
<213> ORGANISM: Homo sapiens

<400> SEQUENCE: 124

Gly Leu Ala Pro Pro Gln His Leu Ile Arg Val
1 5 10

<210> SEQ ID NO 125
<211> LENGTH: 9
<212> TYPE: PRT
<213> ORGANISM: Homo sapiens

<400> SEQUENCE: 125

Leu Leu Gly Arg Asn Ser Phe Glu Val
1 5

<210> SEQ ID NO 126
<211> LENGTH: 9
<212> TYPE: PRT
<213> ORGANISM: Homo sapiens

<400> SEQUENCE: 126

-continued

```
Arg Met Pro Glu Ala Ala Pro Pro Val
1               5


<210> SEQ ID NO 127
<211> LENGTH: 9
<212> TYPE: PRT
<213> ORGANISM: Homo sapiens

<400> SEQUENCE: 127

Ser Thr Pro Pro Pro Gly Thr Arg Val
1               5


<210> SEQ ID NO 128
<211> LENGTH: 9
<212> TYPE: PRT
<213> ORGANISM: Homo sapiens

<400> SEQUENCE: 128

Tyr Leu Val Gly Asn Val Cys Ile Leu
1               5


<210> SEQ ID NO 129
<211> LENGTH: 10
<212> TYPE: PRT
<213> ORGANISM: Homo sapiens

<400> SEQUENCE: 129

Gln Leu Leu Asp Gly Phe Met Ile Thr Leu
1               5                   10


<210> SEQ ID NO 130
<211> LENGTH: 9
<212> TYPE: PRT
<213> ORGANISM: Homo sapiens

<400> SEQUENCE: 130

Glu Leu Ser Asp Ser Leu Gly Pro Val
1               5


<210> SEQ ID NO 131
<211> LENGTH: 9
<212> TYPE: PRT
<213> ORGANISM: Homo sapiens

<400> SEQUENCE: 131

Ser Ile Asp Trp Phe Met Val Thr Val
1               5


<210> SEQ ID NO 132
<211> LENGTH: 9
<212> TYPE: PRT
<213> ORGANISM: Homo sapiens

<400> SEQUENCE: 132

Val Leu Gln Glu Leu Asn Val Thr Val
1               5


<210> SEQ ID NO 133
<211> LENGTH: 10
<212> TYPE: PRT
<213> ORGANISM: Homo sapiens

<400> SEQUENCE: 133

Ala Leu Tyr Val Asp Ser Leu Phe Phe Leu
1               5                   10
```

<210> SEQ ID NO 134
<211> LENGTH: 9
<212> TYPE: PRT
<213> ORGANISM: Homo sapiens

<400> SEQUENCE: 134

Val Leu Asp Gly Leu Asp Val Leu Leu
1 5

<210> SEQ ID NO 135
<211> LENGTH: 9
<212> TYPE: PRT
<213> ORGANISM: Homo sapiens

<400> SEQUENCE: 135

Tyr Leu Gln Trp Ile Glu Phe Ser Ile
1 5

<210> SEQ ID NO 136
<211> LENGTH: 9
<212> TYPE: PRT
<213> ORGANISM: Homo sapiens

<400> SEQUENCE: 136

Lys Leu Gln Cys Val Asp Leu His Val
1 5

<210> SEQ ID NO 137
<211> LENGTH: 10
<212> TYPE: PRT
<213> ORGANISM: Homo sapiens

<400> SEQUENCE: 137

Phe Leu Thr Pro Lys Lys Leu Gln Cys Val
1 5 10

<210> SEQ ID NO 138
<211> LENGTH: 9
<212> TYPE: PRT
<213> ORGANISM: Homo sapiens

<400> SEQUENCE: 138

Ala Ile Leu Ala Leu Leu Pro Ala Leu
1 5

<210> SEQ ID NO 139
<211> LENGTH: 9
<212> TYPE: PRT
<213> ORGANISM: Homo sapiens

<400> SEQUENCE: 139

Gln Leu Gly Glu Gln Cys Trp Thr Val
1 5

<210> SEQ ID NO 140
<211> LENGTH: 9
<212> TYPE: PRT
<213> ORGANISM: Homo sapiens

<400> SEQUENCE: 140

Ser Leu Phe Glu Pro Pro Pro Pro Gly
1 5

-continued

<210> SEQ ID NO 141
<211> LENGTH: 9
<212> TYPE: PRT
<213> ORGANISM: Homo sapiens

<400> SEQUENCE: 141

Met Met Asn Asp Gln Leu Met Phe Leu
1 5

<210> SEQ ID NO 142
<211> LENGTH: 9
<212> TYPE: PRT
<213> ORGANISM: Homo sapiens

<400> SEQUENCE: 142

Val Leu Ala Gly Gly Phe Phe Leu Leu
1 5

<210> SEQ ID NO 143
<211> LENGTH: 10
<212> TYPE: PRT
<213> ORGANISM: Homo sapiens

<400> SEQUENCE: 143

Ala Leu Trp Pro Trp Leu Leu Met Ala Thr
1 5 10

<210> SEQ ID NO 144
<211> LENGTH: 9
<212> TYPE: PRT
<213> ORGANISM: Homo sapiens

<400> SEQUENCE: 144

Arg Leu Ala Glu Tyr Gln Ala Tyr Ile
1 5

<210> SEQ ID NO 145
<211> LENGTH: 9
<212> TYPE: PRT
<213> ORGANISM: Homo sapiens

<400> SEQUENCE: 145

Met Leu Ala Val Phe Leu Pro Ile Val
1 5

<210> SEQ ID NO 146
<211> LENGTH: 9
<212> TYPE: PRT
<213> ORGANISM: Homo sapiens

<400> SEQUENCE: 146

Leu Met Leu Gly Glu Phe Leu Lys Leu
1 5

<210> SEQ ID NO 147
<211> LENGTH: 9
<212> TYPE: PRT
<213> ORGANISM: Homo sapiens

<400> SEQUENCE: 147

Leu Thr Leu Gly Glu Phe Leu Lys Leu
1 5

<210> SEQ ID NO 148
<211> LENGTH: 10

<212> TYPE: PRT
<213> ORGANISM: Homo sapiens

<400> SEQUENCE: 148

Thr Leu Pro Pro Ala Trp Gln Pro Phe Leu
1 5 10

<210> SEQ ID NO 149
<211> LENGTH: 9
<212> TYPE: PRT
<213> ORGANISM: Homo sapiens

<400> SEQUENCE: 149

Tyr Leu Ile Glu Leu Ile Asp Arg Val
1 5

<210> SEQ ID NO 150
<211> LENGTH: 10
<212> TYPE: PRT
<213> ORGANISM: Homo sapiens

<400> SEQUENCE: 150

Phe Leu Pro Ser Pro Leu Phe Phe Phe Leu
1 5 10

<210> SEQ ID NO 151
<211> LENGTH: 9
<212> TYPE: PRT
<213> ORGANISM: Homo sapiens

<400> SEQUENCE: 151

Phe Leu Phe Leu Arg Asn Phe Ser Leu
1 5

<210> SEQ ID NO 152
<211> LENGTH: 10
<212> TYPE: PRT
<213> ORGANISM: Homo sapiens

<400> SEQUENCE: 152

Tyr Leu Gln Val Asn Ser Leu Gln Thr Val
1 5 10

<210> SEQ ID NO 153
<211> LENGTH: 9
<212> TYPE: PRT
<213> ORGANISM: Homo sapiens

<400> SEQUENCE: 153

Ile Leu Ala Lys Phe Leu His Trp Leu
1 5

<210> SEQ ID NO 154
<211> LENGTH: 10
<212> TYPE: PRT
<213> ORGANISM: Homo sapiens

<400> SEQUENCE: 154

Ala Leu Leu Thr Ser Arg Leu Arg Phe Ile
1 5 10

<210> SEQ ID NO 155
<211> LENGTH: 9
<212> TYPE: PRT
<213> ORGANISM: Homo sapiens

<400> SEQUENCE: 155

Arg Leu Thr Ser Arg Val Lys Ala Leu
1 5

<210> SEQ ID NO 156
<211> LENGTH: 10
<212> TYPE: PRT
<213> ORGANISM: Homo sapiens

<400> SEQUENCE: 156

Gly Leu Leu Gly Ala Ser Val Leu Gly Leu
1 5 10

<210> SEQ ID NO 157
<211> LENGTH: 9
<212> TYPE: PRT
<213> ORGANISM: Homo sapiens

<400> SEQUENCE: 157

Arg Leu Ser Ser Cys Val Pro Val Ala
1 5

<210> SEQ ID NO 158
<211> LENGTH: 9
<212> TYPE: PRT
<213> ORGANISM: Homo sapiens

<400> SEQUENCE: 158

Phe Leu Tyr Asp Asp Asn Gln Arg Val
1 5

<210> SEQ ID NO 159
<211> LENGTH: 9
<212> TYPE: PRT
<213> ORGANISM: Homo sapiens

<400> SEQUENCE: 159

Gly Leu Ile Gln Leu Val Glu Gly Val
1 5

<210> SEQ ID NO 160
<211> LENGTH: 10
<212> TYPE: PRT
<213> ORGANISM: Homo sapiens

<400> SEQUENCE: 160

Ser Ile Leu Leu Arg Asp Ala Gly Leu Val
1 5 10

<210> SEQ ID NO 161
<211> LENGTH: 9
<212> TYPE: PRT
<213> ORGANISM: Homo sapiens

<400> SEQUENCE: 161

Leu Leu Leu Thr Val Leu Thr Val Val
1 5

<210> SEQ ID NO 162
<211> LENGTH: 9
<212> TYPE: PRT
<213> ORGANISM: Homo sapiens

<400> SEQUENCE: 162

Leu Leu Leu Leu Thr Val Leu Thr Val
1               5

<210> SEQ ID NO 163
<211> LENGTH: 9
<212> TYPE: PRT
<213> ORGANISM: Homo sapiens

<400> SEQUENCE: 163

Tyr Met Asp Gly Thr Met Ser Gln Val
1               5

<210> SEQ ID NO 164
<211> LENGTH: 9
<212> TYPE: PRT
<213> ORGANISM: Homo sapiens

<400> SEQUENCE: 164

Arg Met Phe Pro Asn Ala Pro Tyr Leu
1               5

<210> SEQ ID NO 165
<211> LENGTH: 9
<212> TYPE: PRT
<213> ORGANISM: Homo sapiens

<400> SEQUENCE: 165

Val Leu Asp Phe Ala Pro Pro Gly Ala
1               5

<210> SEQ ID NO 166
<211> LENGTH: 9
<212> TYPE: PRT
<213> ORGANISM: Homo sapiens

<400> SEQUENCE: 166

Ser Leu Gly Glu Gln Gln Tyr Ser Val
1               5

<210> SEQ ID NO 167
<211> LENGTH: 9
<212> TYPE: PRT
<213> ORGANISM: Homo sapiens

<400> SEQUENCE: 167

Cys Leu Trp Cys Val Pro Gln Leu Arg
1               5

<210> SEQ ID NO 168
<211> LENGTH: 9
<212> TYPE: PRT
<213> ORGANISM: Homo sapiens

<400> SEQUENCE: 168

Gly Val Arg Gly Arg Val Glu Glu Ile
1               5

<210> SEQ ID NO 169
<211> LENGTH: 9
<212> TYPE: PRT
<213> ORGANISM: Homo sapiens

<400> SEQUENCE: 169

Arg Leu Met Asn Asp Met Thr Ala Val 1 5

<210> SEQ ID NO 170
<211> LENGTH: 10
<212> TYPE: PRT
<213> ORGANISM: Homo sapiens

<400> SEQUENCE: 170

Lys Leu Met Ser Ser Asn Ser Thr Asp Leu
1 5 10

<210> SEQ ID NO 171
<211> LENGTH: 9
<212> TYPE: PRT
<213> ORGANISM: Homo sapiens

<400> SEQUENCE: 171

Leu Leu Thr Ala Ala Leu Trp Tyr Val
1 5

<210> SEQ ID NO 172
<211> LENGTH: 9
<212> TYPE: PRT
<213> ORGANISM: Homo sapiens

<400> SEQUENCE: 172

Asp Tyr Leu Gln Tyr Val Leu Gln Ile
1 5

<210> SEQ ID NO 173
<211> LENGTH: 9
<212> TYPE: PRT
<213> ORGANISM: Homo sapiens

<400> SEQUENCE: 173

Gly Tyr Cys Thr Gln Ile Gly Ile Phe
1 5

<210> SEQ ID NO 174
<211> LENGTH: 9
<212> TYPE: PRT
<213> ORGANISM: Homo sapiens

<400> SEQUENCE: 174

Glu Tyr Arg Ala Leu Gln Leu His Leu
1 5

<210> SEQ ID NO 175
<211> LENGTH: 9
<212> TYPE: PRT
<213> ORGANISM: Homo sapiens

<400> SEQUENCE: 175

Glu Tyr Tyr Glu Leu Phe Val Asn Ile
1 5

<210> SEQ ID NO 176
<211> LENGTH: 9
<212> TYPE: PRT
<213> ORGANISM: Homo sapiens

<400> SEQUENCE: 176

Ile Tyr Thr Trp Ile Glu Asp His Phe
1 5

<210> SEQ ID NO 177
<211> LENGTH: 9
<212> TYPE: PRT
<213> ORGANISM: Homo sapiens

<400> SEQUENCE: 177

Glu Tyr Ile Leu Ser Leu Glu Glu Leu
1               5

<210> SEQ ID NO 178
<211> LENGTH: 9
<212> TYPE: PRT
<213> ORGANISM: Homo sapiens

<400> SEQUENCE: 178

Val Tyr Phe Phe Leu Pro Asp His Leu
1               5

<210> SEQ ID NO 179
<211> LENGTH: 9
<212> TYPE: PRT
<213> ORGANISM: Homo sapiens

<400> SEQUENCE: 179

Lys Trp Leu Ile Ser Pro Val Lys Ile
1               5

<210> SEQ ID NO 180
<211> LENGTH: 10
<212> TYPE: PRT
<213> ORGANISM: Homo sapiens

<400> SEQUENCE: 180

Lys Leu Arg Gly Glu Val Lys Gln Asn Leu
1               5                   10

<210> SEQ ID NO 181
<211> LENGTH: 9
<212> TYPE: PRT
<213> ORGANISM: Homo sapiens

<400> SEQUENCE: 181

Val Tyr Tyr Asn Trp Gln Tyr Leu Leu
1               5

<210> SEQ ID NO 182
<211> LENGTH: 10
<212> TYPE: PRT
<213> ORGANISM: Homo sapiens

<400> SEQUENCE: 182

Lys Tyr Tyr Leu Arg Val Arg Pro Leu Leu
1               5                   10

<210> SEQ ID NO 183
<211> LENGTH: 9
<212> TYPE: PRT
<213> ORGANISM: Homo sapiens

<400> SEQUENCE: 183

Val Tyr Leu Arg Val Arg Pro Leu Leu
1               5

<210> SEQ ID NO 184

<211> LENGTH: 10
<212> TYPE: PRT
<213> ORGANISM: Homo sapiens

<400> SEQUENCE: 184

Arg Tyr Cys Asn Leu Glu Gly Pro Pro Ile
1 5 10

<210> SEQ ID NO 185
<211> LENGTH: 9
<212> TYPE: PRT
<213> ORGANISM: Homo sapiens

<400> SEQUENCE: 185

Glu Tyr Cys Pro Gly Gly Asn Leu Phe
1 5

<210> SEQ ID NO 186
<211> LENGTH: 10
<212> TYPE: PRT
<213> ORGANISM: Homo sapiens

<400> SEQUENCE: 186

Arg Tyr Asn Ala Gln Cys Gln Glu Thr Ile
1 5 10

<210> SEQ ID NO 187
<211> LENGTH: 9
<212> TYPE: PRT
<213> ORGANISM: Homo sapiens

<400> SEQUENCE: 187

Val Tyr Gly Ile Arg Leu Glu His Phe
1 5

<210> SEQ ID NO 188
<211> LENGTH: 9
<212> TYPE: PRT
<213> ORGANISM: Homo sapiens

<400> SEQUENCE: 188

Leu Tyr Gln Trp Leu Gly Ala Pro Val
1 5

<210> SEQ ID NO 189
<211> LENGTH: 10
<212> TYPE: PRT
<213> ORGANISM: Homo sapiens

<400> SEQUENCE: 189

Asp Tyr Leu Asn Glu Trp Gly Ser Arg Phe
1 5 10

<210> SEQ ID NO 190
<211> LENGTH: 9
<212> TYPE: PRT
<213> ORGANISM: Homo sapiens

<400> SEQUENCE: 190

Cys Tyr Ala Ser Gly Trp Gly Ser Ile
1 5

<210> SEQ ID NO 191
<211> LENGTH: 9
<212> TYPE: PRT

<213> ORGANISM: Homo sapiens

<400> SEQUENCE: 191

Asn Tyr Gln Pro Val Trp Leu Cys Leu
1 5

<210> SEQ ID NO 192
<211> LENGTH: 9
<212> TYPE: PRT
<213> ORGANISM: Homo sapiens

<400> SEQUENCE: 192

Ala Tyr Ala Cys Asn Thr Ser Thr Leu
1 5

<210> SEQ ID NO 193
<211> LENGTH: 9
<212> TYPE: PRT
<213> ORGANISM: Homo sapiens

<400> SEQUENCE: 193

Ser Tyr Arg Asn Glu Ile Ala Tyr Leu
1 5

<210> SEQ ID NO 194
<211> LENGTH: 9
<212> TYPE: PRT
<213> ORGANISM: Homo sapiens

<400> SEQUENCE: 194

Ala Phe Leu Pro Trp His Arg Leu Phe
1 5

<210> SEQ ID NO 195
<211> LENGTH: 9
<212> TYPE: PRT
<213> ORGANISM: Homo sapiens

<400> SEQUENCE: 195

Cys Tyr Thr Trp Asn Gln Met Asn Leu
1 5

<210> SEQ ID NO 196
<211> LENGTH: 8
<212> TYPE: PRT
<213> ORGANISM: Gallus gallus domesticus

<400> SEQUENCE: 196

Ser Ile Ile Asn Phe Glu Lys Leu
1 5

<210> SEQ ID NO 197
<211> LENGTH: 9
<212> TYPE: PRT
<213> ORGANISM: Mus musculus

<400> SEQUENCE: 197

Glu Gly Ser Arg Asn Gln Asp Trp Leu
1 5

<210> SEQ ID NO 198
<211> LENGTH: 9
<212> TYPE: PRT
<213> ORGANISM: Homo sapiens

<400> SEQUENCE: 198

Lys Val Pro Arg Asn Gln Asp Trp Leu
1 5

<210> SEQ ID NO 199
<211> LENGTH: 9
<212> TYPE: PRT
<213> ORGANISM: Homo sapiens

<400> SEQUENCE: 199

Ser Pro Ser Tyr Val Tyr His Gln Phe
1 5

<210> SEQ ID NO 200
<211> LENGTH: 9
<212> TYPE: PRT
<213> ORGANISM: Influenza A virus

<400> SEQUENCE: 200

Ile Tyr Ser Thr Val Ala Ser Ser Leu
1 5

<210> SEQ ID NO 201
<211> LENGTH: 9
<212> TYPE: PRT
<213> ORGANISM: Influenza A virus

<400> SEQUENCE: 201

Ala Ser Asn Glu Asn Met Asp Thr Met
1 5

<210> SEQ ID NO 202
<211> LENGTH: 10
<212> TYPE: PRT
<213> ORGANISM: Influenza A virus

<400> SEQUENCE: 202

Ser Ser Leu Glu Asn Phe Arg Ala Tyr Val
1 5 10

<210> SEQ ID NO 203
<211> LENGTH: 8
<212> TYPE: PRT
<213> ORGANISM: Homo sapiens

<400> SEQUENCE: 203

Asp Ala Pro Ile Tyr Thr Asn Val
1 5

<210> SEQ ID NO 204
<211> LENGTH: 8
<212> TYPE: PRT
<213> ORGANISM: Mouse leukemogenic retrovirus

<400> SEQUENCE: 204

Lys Ser Pro Trp Phe Thr Thr Leu
1 5

<210> SEQ ID NO 205
<211> LENGTH: 9
<212> TYPE: PRT
<213> ORGANISM: Sendai virus

<400> SEQUENCE: 205

Phe Ala Pro Gly Asn Tyr Pro Ala Leu
1               5

<210> SEQ ID NO 206
<211> LENGTH: 9
<212> TYPE: PRT
<213> ORGANISM: Mouse cytomegalovirus 1

<400> SEQUENCE: 206

Tyr Pro His Phe Met Pro Thr Asn Leu
1               5

<210> SEQ ID NO 207
<211> LENGTH: 9
<212> TYPE: PRT
<213> ORGANISM: Lymphocytic choriomeningitis virus

<400> SEQUENCE: 207

Lys Ala Val Tyr Asn Phe Ala Thr Met
1               5

<210> SEQ ID NO 208
<211> LENGTH: 9
<212> TYPE: PRT
<213> ORGANISM: Lymphocytic choriomeningitis virus

<400> SEQUENCE: 208

Phe Gln Pro Gln Asn Gly Gln Phe Ile
1               5

<210> SEQ ID NO 209
<211> LENGTH: 9
<212> TYPE: PRT
<213> ORGANISM: Lymphocytic choriomeningitis virus

<400> SEQUENCE: 209

Arg Pro Gln Ala Ser Gly Val Tyr Met
1               5

<210> SEQ ID NO 210
<211> LENGTH: 9
<212> TYPE: PRT
<213> ORGANISM: Plasmodium malariae

<400> SEQUENCE: 210

Ser Tyr Ile Pro Ser Ala Glu Lys Ile
1               5

<210> SEQ ID NO 211
<211> LENGTH: 10
<212> TYPE: PRT
<213> ORGANISM: Human immunodeficiency virus

<400> SEQUENCE: 211

Arg Gly Pro Gly Arg Ala Phe Val Thr Ile
1               5                   10

<210> SEQ ID NO 212
<211> LENGTH: 9
<212> TYPE: PRT
<213> ORGANISM: Mycobacterium bovis

<400> SEQUENCE: 212

Gly Gly Pro His Ala Val Tyr Leu Leu
1               5

<210> SEQ ID NO 213
<211> LENGTH: 8
<212> TYPE: PRT
<213> ORGANISM: Homo sapiens

<400> SEQUENCE: 213

Glu Ala Gln Asn Thr Thr Tyr Leu
1               5

<210> SEQ ID NO 214
<211> LENGTH: 9
<212> TYPE: PRT
<213> ORGANISM: Mus musculus

<400> SEQUENCE: 214

Leu Pro Tyr Leu Gly Trp Leu Val Phe
1               5

<210> SEQ ID NO 215
<211> LENGTH: 12
<212> TYPE: PRT
<213> ORGANISM: Hepatitis B virus

<400> SEQUENCE: 215

Ile Pro Gln Ser Leu Asp Ser Trp Trp Thr Ser Leu
1               5                   10

<210> SEQ ID NO 216
<211> LENGTH: 8
<212> TYPE: PRT
<213> ORGANISM: herpes simplex virus 1

<400> SEQUENCE: 216

Ser Ser Ile Glu Phe Ala Arg Leu
1               5

<210> SEQ ID NO 217
<211> LENGTH: 9
<212> TYPE: PRT
<213> ORGANISM: Homo sapiens

<400> SEQUENCE: 217

Trp Met His His Asn Met Asp Leu Ile
1               5

<210> SEQ ID NO 218
<211> LENGTH: 9
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(9)
<223> OTHER INFORMATION: an epitope derived from enhanced green fluorescent protein

<400> SEQUENCE: 218

His Tyr Leu Ser Thr Gln Ser Ala Leu
1               5

<210> SEQ ID NO 219
<211> LENGTH: 9
<212> TYPE: PRT
<213> ORGANISM: Homo sapiens

<400> SEQUENCE: 219

Thr Tyr Leu Pro Thr Asn Ala Ser Leu
1               5

<210> SEQ ID NO 220
<211> LENGTH: 8
<212> TYPE: PRT
<213> ORGANISM: Vesicular stomatitis virus

<400> SEQUENCE: 220

Arg Gly Tyr Val Tyr Gln Gly Leu
1               5

<210> SEQ ID NO 221
<211> LENGTH: 9
<212> TYPE: PRT
<213> ORGANISM: Polyomavirus

<400> SEQUENCE: 221

Arg Arg Leu Gly Arg Thr Leu Leu Leu
1               5

<210> SEQ ID NO 222
<211> LENGTH: 20
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(20)
<223> OTHER INFORMATION: K3

<400> SEQUENCE: 222
atcgactctc gagcgttctc                                                20

<210> SEQ ID NO 223
<211> LENGTH: 20
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(20)
<223> OTHER INFORMATION: K3-20(b)

<400> SEQUENCE: 223
gagcgttctc gagcgttctc                                                20

<210> SEQ ID NO 224
<211> LENGTH: 21
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(21)
<223> OTHER INFORMATION: K3-21

<400> SEQUENCE: 224
cgagcgttct cgagcgttct c                                              21

<210> SEQ ID NO 225
<211> LENGTH: 24

<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(24)
<223> OTHER INFORMATION: K3-24

<400> SEQUENCE: 225
tctcgagcgt tctcgagcgt tctc 24

<210> SEQ ID NO 226
<211> LENGTH: 27
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(27)
<223> OTHER INFORMATION: K3-27

<400> SEQUENCE: 226
gactctcgag cgttctcgag cgttctc 27

<210> SEQ ID NO 227
<211> LENGTH: 30
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(30)
<223> OTHER INFORMATION: K3-30(a)

<400> SEQUENCE: 227
gagcgttctc atcgactctc gagcgttctc 30

<210> SEQ ID NO 228
<211> LENGTH: 30
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(30)
<223> OTHER INFORMATION: K3-30(b)

<400> SEQUENCE: 228
atcgactctc gagcgttctc gagcgttctc 30

<210> SEQ ID NO 229
<211> LENGTH: 40
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(40)
<223> OTHER INFORMATION: K3-40

<400> SEQUENCE: 229
atcgactctc gagcgttctc atcgactctc gagcgttctc 40

<210> SEQ ID NO 230

<211> LENGTH: 30
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(30)
<223> OTHER INFORMATION: K3-30(c)

<400> SEQUENCE: 230
ctcagcgttc tcagcgttct cagcgttctc 30

<210> SEQ ID NO 231
<211> LENGTH: 30
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(30)
<223> OTHER INFORMATION: K3-30(d)

<400> SEQUENCE: 231
tttagcgttt ttagcgtttt tagcgttttt 30

<210> SEQ ID NO 232
<211> LENGTH: 30
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(30)
<223> OTHER INFORMATION: K3-30(e)

<400> SEQUENCE: 232
ttagcgttta gcgtttagcg tttagcgttt 30

<210> SEQ ID NO 233
<211> LENGTH: 30
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(30)
<223> OTHER INFORMATION: K3-30(f)

<400> SEQUENCE: 233
ttagcgttta gcgtttagcg tttagcgttt 30

<210> SEQ ID NO 234
<211> LENGTH: 26
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(26)
<223> OTHER INFORMATION: K3-26(a)

<400> SEQUENCE: 234
tcagcgtttc agcgtttcag cgtttc 26

<210> SEQ ID NO 235
<211> LENGTH: 26
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(26)
<223> OTHER INFORMATION: K3-26(b)

<400> SEQUENCE: 235
ttagcgtttt agcgttttag cgtttt 26

<210> SEQ ID NO 236
<211> LENGTH: 20
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(20)
<223> OTHER INFORMATION: ODN1668

<400> SEQUENCE: 236
tccatgacgt tcctgatgct 20

<210> SEQ ID NO 237
<211> LENGTH: 30
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(30)
<223> OTHER INFORMATION: ODN1668-30

<400> SEQUENCE: 237
tgacgttcct tccatgacgt tcctgatgct 30

<210> SEQ ID NO 238
<211> LENGTH: 40
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(40)
<223> OTHER INFORMATION: ODN1668-40

<400> SEQUENCE: 238
tccatgacgt tcctgatgct tccatgacgt tcctgatgct 40

<210> SEQ ID NO 239
<211> LENGTH: 20
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(20)
<223> OTHER INFORMATION: ODN1826

<400> SEQUENCE: 239
tccatgacgt tcctgacgtt 20

<210> SEQ ID NO 240
<211> LENGTH: 30
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(30)
<223> OTHER INFORMATION: ODN1826-30

<400> SEQUENCE: 240
tgacgttcct tccatgacgt tcctgacgtt 30

<210> SEQ ID NO 241
<211> LENGTH: 40
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(40)
<223> OTHER INFORMATION: ODN1826-40

<400> SEQUENCE: 241
tccatgacgt tcctgacgtt tccatgacgt tcctgacgtt 40

<210> SEQ ID NO 242
<211> LENGTH: 24
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(24)
<223> OTHER INFORMATION: ODN2006

<400> SEQUENCE: 242
tcgtcgtttt gtcgttttgt cgtt 24

<210> SEQ ID NO 243
<211> LENGTH: 30
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(30)
<223> OTHER INFORMATION: ODN2006-30

<400> SEQUENCE: 243
gtcgtttcgt cgttttgtcg ttttgtcgtt 30

<210> SEQ ID NO 244
<211> LENGTH: 40
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(40)
<223> OTHER INFORMATION: ODN2006-40

<400> SEQUENCE: 244
tcgtcgtttt gtcgtttcgt cgttttgtcg ttttgtcgtt 40

<210> SEQ ID NO 245
<211> LENGTH: 23
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(23)
<223> OTHER INFORMATION: ODN684

<400> SEQUENCE: 245
tcgacgttcg tcgttcgtcg ttc 23

<210> SEQ ID NO 246
<211> LENGTH: 30
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(30)
<223> OTHER INFORMATION: ODN684-30

<400> SEQUENCE: 246
tcgtcgttcg acgttcgtcg ttcgtcgttc 30

<210> SEQ ID NO 247
<211> LENGTH: 40
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(40)
<223> OTHER INFORMATION: ODN684-40

<400> SEQUENCE: 247
gttcgtcgtt tcgtcgttcg acgttcgtcg ttcgtcgttc 40

<210> SEQ ID NO 248
<211> LENGTH: 26
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(26)
<223> OTHER INFORMATION: ODN D-SL01

<400> SEQUENCE: 248
tcgcgacgtt cgcccgacgt tcggta 26

<210> SEQ ID NO 249
<211> LENGTH: 35
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(35)
<223> OTHER INFORMATION: ODN D-SL01-35

<400> SEQUENCE: 249

-continued tcgcgacgtt cgcgacgttc gcccgacgtt cggta 35

<210> SEQ ID NO 250
<211> LENGTH: 9
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(9)
<223> OTHER INFORMATION: OVApep9

<400> SEQUENCE: 250

Cys Ser Ile Ile Asn Phe Glu Lys Leu
1 5

<210> SEQ ID NO 251
<211> LENGTH: 18
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(18)
<223> OTHER INFORMATION: OVApep18

<400> SEQUENCE: 251

Cys Glu Val Ser Gly Leu Glu Gln Leu Glu Ser Ile Ile Asn Phe Glu
1 5 10 15

Lys Leu

<210> SEQ ID NO 252
<211> LENGTH: 27
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(27)
<223> OTHER INFORMATION: OVApep27

<400> SEQUENCE: 252

Cys Met Ser Met Leu Val Leu Leu Pro Asp Glu Val Ser Gly Leu Glu
1 5 10 15

Gln Leu Glu Ser Ile Ile Asn Phe Glu Lys Leu
20 25